US005763427A

United States Patent [19]
Weitz et al.

[11] Patent Number: 5,763,427
[45] Date of Patent: *Jun. 9, 1998

[54] COMPOSITIONS AND METHODS FOR INHIBITING THROMBOGENESIS

[75] Inventors: Jeffrey I. Weitz, Ancaster; Jack Hirsh, Hamilton; Edward Young, Oakville, all of Canada

[73] Assignee: Hamilton Civic Hospitals Research Development Inc., Canada

[*] Notice: The term of this patent shall not extend beyond the expiration date of Pat. No. 5,744,527.

[21] Appl. No.: 624,327

[22] Filed: Mar. 29, 1996

Related U.S. Application Data

[63] Continuation-in-part of Ser. No. 540,324, Oct. 6, 1995, Pat. No. 5,744,457, which is a continuation-in-part of Ser. No. 412,332, Mar. 31, 1995, abandoned.

[51] Int. Cl.$^6$ .................... A61K 31/725; C08B 37/10
[52] U.S. Cl. .................... 514/56; 536/21; 536/122; 536/123.1; 536/124; 514/54; 514/56; 514/921
[58] Field of Search .................... 536/21, 122, 123.1, 536/124; 514/54, 56, 921

[56] References Cited

U.S. PATENT DOCUMENTS

| | | | |
|---|---|---|---|
| 4,281,108 | 7/1981 | Fussi | 536/21 |
| 4,351,938 | 9/1982 | Barnett | 536/21 |
| 4,496,550 | 1/1985 | Lindahl et al. | 514/54 |
| 4,500,519 | 2/1985 | Lormeau et al. | 514/56 |
| 4,629,699 | 12/1986 | Bianchini | 435/101 |
| 4,687,765 | 8/1987 | Vairel et al. | 514/56 |
| 4,791,195 | 12/1988 | Bianchini | 536/21 |
| 4,847,338 | 7/1989 | Linhardt et al. | 536/54 |
| 4,916,219 | 4/1990 | Linhardt et al. | 536/21 |
| 4,933,326 | 6/1990 | Bianchini et al. | 514/56 |
| 4,942,156 | 7/1990 | Foley et al. | 514/56 |
| 4,981,955 | 1/1991 | Lopez | 536/21 |
| 4,990,502 | 2/1991 | Lormeau et al. | 536/55.3 |
| 5,010,063 | 4/1991 | Piani et al. | 514/56 |
| 5,013,724 | 5/1991 | Petitou et al. | 514/54 |
| 5,019,649 | 5/1991 | Lormeau et al. | 536/21 |
| 5,039,529 | 8/1991 | Bergendahl et al. | 424/630 |
| 5,084,564 | 1/1992 | Vila et al. | 536/21 |
| 5,106,734 | 4/1992 | Nielsen | 435/84 |
| 5,236,910 | 8/1993 | Egidio et al. | 514/56 |
| 5,547,944 | 8/1996 | Mascellani et al. | 514/54 |

FOREIGN PATENT DOCUMENTS

| | | |
|---|---|---|
| 101 141 | 2/1984 | European Pat. Off. . |
| 121 067 | 4/1987 | European Pat. Off. . |
| 244 235 | 11/1987 | European Pat. Off. . |
| 048 231 | 6/1988 | European Pat. Off. . |
| 337 327 | 10/1989 | European Pat. Off. . |
| 214 879 | 11/1990 | European Pat. Off. . |
| 496 233 | 7/1992 | European Pat. Off. . |
| 511 075 | 10/1992 | European Pat. Off. . |
| 513 513 | 11/1992 | European Pat. Off. . |
| 355 905 | 1/1993 | European Pat. Off. . |
| 293 539 | 6/1994 | European Pat. Off. . |
| 287 477 | 11/1994 | European Pat. Off. . |
| 623 629 | 11/1994 | European Pat. Off. . |
| WO 82/01005 | 4/1982 | WIPO . |
| WO 82/03627 | 10/1982 | WIPO . |
| WO 90/01501 | 2/1990 | WIPO . |
| WO 90/04607 | 5/1990 | WIPO . |
| WO 90/04970 | 5/1990 | WIPO . |
| WO 91/15217 | 10/1991 | WIPO . |
| WO 92/02232 | 2/1992 | WIPO . |
| WO 92/11294 | 7/1992 | WIPO . |
| WO 92/17187 | 10/1992 | WIPO . |
| WO 92/17188 | 10/1992 | WIPO . |
| WO 92/17506 | 10/1992 | WIPO . |
| WO 92/18545 | 10/1992 | WIPO . |
| WO 93/05074 | 3/1993 | WIPO . |
| WO 93/16112 | 8/1993 | WIPO . |
| WO 93/19737 | 10/1993 | WIPO . |
| WO 94/12618 | 6/1994 | WIPO . |
| WO 95/12403 | 5/1995 | WIPO . |

OTHER PUBLICATIONS

Alhenc–Gelas, et al., "Laboratory Control of Low–Molecular–Weight Heparins: Needs and Possibilities," *Fundamental and Clinical Cardiology*, 19:43–54 (1994).

Atha, et al., "Physicochemical Characterization of Low Molecular Weight Heparin," *J. Pharm. Sciences*, 84(3):360–364 (Mar. 1995).

Barzu, et al., "O–Acylated heparin derivatives with low anticoagulant activity decrease proliferation and increase α–smooth muscle active expression in cultured arterial smooth muscle cells," *Euro. J. Pharm.*, 219:225–233 (1992).

Barzu, et al., "Preparation and Anti–HIV Activity of O–Acylated Heparin and Dermatan Sulfate Derivatives with Low Anticoagulant Effect," *J. Med. Chem.*, 36:3546–3555 (1993).

Cifonelli, et al., "The Distribution of 2–Acetamido–2–Deoxy–D–glucose residues in Mammalian Heparins," *Charbo. Res.*, 21:173–186 (1972).

Doctor, et al., "Anticoagulant Properties of Semisynthetic Polysaccharide Sulfates," *Thrombosis Research*, 64:413–425 (1991).

(List continued on next page.)

*Primary Examiner*—Kathleen K. Fonda
*Attorney, Agent, or Firm*—Townsend & Townsend & Crew LLP

[57] ABSTRACT

The present invention provides compositions and methods for inactivating thrombin bound to fibrin within a thrombus or clot, whereby the ability of clot-bound thrombin to catalytically promote further clot accretion is substantially diminished or eliminated. The compositions and methods of the present invention are particularly useful for preventing thrombosis in the circuit of cardiac bypass apparatus and in patients undergoing renal dialysis, and for treating patients suffering from or at risk of suffering from thrombus-related cardiovascular conditions, such as unstable angina, acute myocardial infarction (heart attack), cerebrovascular accidents (stroke), pulmonary embolism, deep vein thrombosis, arterial thrombosis, etc.

56 Claims, 35 Drawing Sheets

OTHER PUBLICATIONS

Horton, et al., The Nitrous Acid Deamination of Glycosides and Acetates of 2–Amino–2–Deoxy–D–Glucose, *Charbo. Res.*, 30:367–374 (1973).

Jordan, et al., "The Kinetics of Hemostatic Enzyme–Antithrombin Interactions in the Presence of Low Molecular Weight Heparin," *J. of Biol. Chem.*, 255(21):10081–10090 (1980).

Lagunoff, et al., "Determination of 2–Deopxy–2–Sulfoaminohexose Content of Mucopolysaccharides," *Archives of Biochem. and Biophys.*, 99:396–400 (1962).

Lindhardt, et al., "Oligosaccharide Mapping of Low Molecular Weight Heparins: Structure and Activity Differences," *J. Med. Chem.*, 33:1639–1645 (1990).

Mascellani, et al., Active Sites of Dermatan Sulfate for Heparin Cofactor II. Isolation of a Nonasaccharide Fragment Containing Four Disaccharide Sequences [α–L–Iduronic Acid 2–0–Sulfate (1,3)–β–D–N–Acetylgalactosamine 4–Sulfate], *J. Carbohydrate Chem.*, 14(8):1165–1177 (1995).

Mattsson, et al., "Antithrombotic Effects of Heparin Oligosaccharides," *Annals of the N.Y. Acad. Sci.*, 556:323–332 (1989).

Nagase, et al., "Depolymerized Holothurian Glycosaminoglycan With Novel Anticoagulant Actions: Antithrombin III–and Heparin Cofactor II–Independent Inhibition of Factor X Activation by Factor IXa–Factor VIIIa Complex and Heparin Cofactor II–Dependent Inhibition of Thrombin," *Blood*, 85(6):1527–1534 (1995).

Schoen, et al., "The Effect of Sulfation of the Anticoagulant and Antithrombin III–Binding Properties of a Heparin Fraction with Low Affinity for Antithrombin III," *Thrombosis Research*, 57:415–423 (1990).

Shimotori, et al., "Comparative Studies of Heparin Cofactor Activity Toward Antithrombin III and Heparin Cofactor II, and Antithrombin III Affinity Between Low Molecular Weight heparin and Unfractionated Heparin," *Seminars in Thrombosis and Hemostasis*, 16 (supp.):71–76 (1990).

Shively, et al., "Formation of Anhydrosugars in the Chemical Depolymerization of Heparin," *Biochemistry*, 15(18):3932–3942 (1976).

Shively, et al., "Nearest Neighbor Analysis of Heparin: Identification and Quantitation of the Products Formed by Selective Depolymerization Procedures," *Biochemistry*, 15(18):3943–3950 (1976).

Shively, et al., "Stoichiometry of the Nitrous Acid Deaminative Cleavage of Model Amino Sugar Glycosides and Glycosaminoglycuronans," *Biochemistry*, 9(1):33–43 (1970).

Svahn, et al., "Inhibition of angiogenesis by heparin fragments in the presence of hydrocortisone," *Carbohydrate Polymers*, 18:9–16 (1992).

Tollefsen, et al., "Effect of Low Molecular Weight Heparin Preparations on the Inhibition of Thrombin by Heparin Cofactor II," *Seminars in Thrombosis and Hemostasis*, 16 (supp.):66–70 (1990).

Weitz, et al., "New Anticoagulant Strategies," *J. Lab. Clin. Med.*, 122(4):364–373 (1993).

Cade, et al., "A Comparison of the Antithrombotic and Haemorrhagic Effects of Low Molecular Weight Heparin Fractions: The Influence of the Method of Preparation," *Thrombosis Research*, 35:613–625 (1984).

The Merck Index, Twelfth Edition; S. Budavari et al., eds.; Merck & Co., Inc., 1996, Whitehouse Station, New Jersey; monograph 4685.

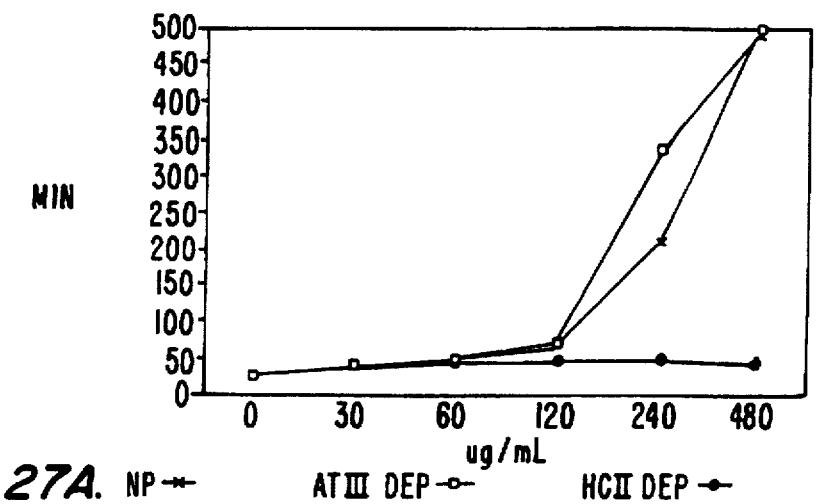
FIG. 27A.  NP -x-   ATIII DEP -o-   HCII DEP -•-
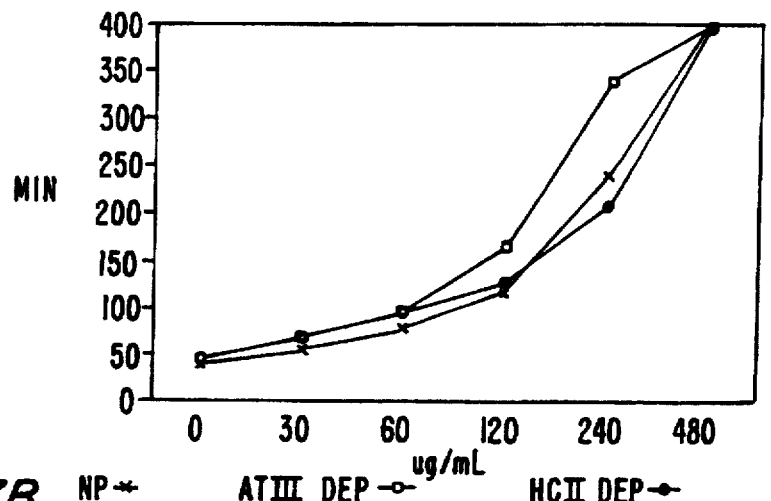
FIG. 27B.  NP -x-   ATIII DEP -o-   HCII DEP -•-
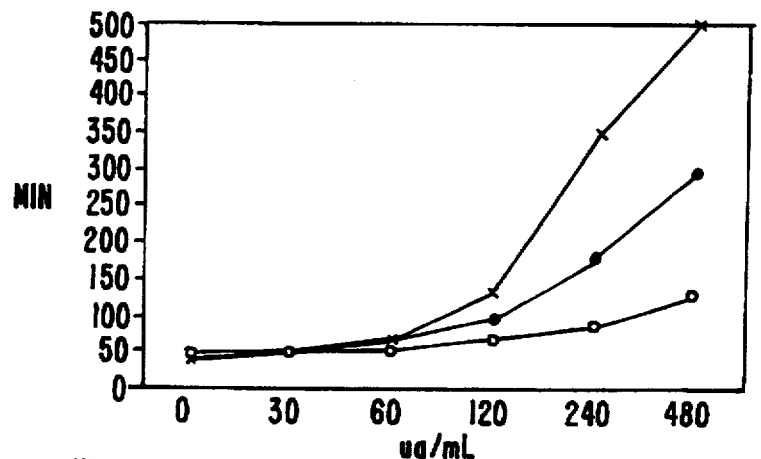
FIG. 27C.  NP -x-   ATIII DEP -o-   HCII DEP -•-

| L-18 | FBG | +AT III | +HCoF II |
|---|---|---|---|
| 0 | 24.6 | 25.6 | 27.8 |
| 120 | 27.4 | 29.9 | 56.2 |
| 240 | 29.7 | 33.1 | 83.9 |
| 480 | 30.1 | 36 | >500 |
| 960 | 30.9 | 36.3 | >500 |

| CONC. | 2.0 u/L | 2.5 uM | 1 uM |
|---|---|---|---|
| DS | FBG ONLY | +AT III | +HCoF II |
| 0 | 23.1 | 29.9 | 28.4 |
| 15 | 25.4 | 30.9 | 113.5 |
| 30 | 24 | 31.6 | >800 |
| 60 | 25.5 | 32.3 | >800 |
| 120 | 25.4 | 30.8 | >800 |
| 240 | 25.7 | 37.8 | >800 |
| 480 | 25.4 | 36.7 | >800 |

| SH | FBG | +AT III | +HCoF II |
|---|---|---|---|
| 0 | 24.6 | 25.6 | 27.8 |
| 0.2 | 28.3 | >500 | 62.8 |
| 0.4 | 31.9 | >500 | >500 |
| 0.6 | 33 | >500 | >500 |
| 0.8 | 29.4 | >500 | >500 |

| STD HEP | IXa CLOT | Xa CLOT | XIa CLOT |
|---|---|---|---|
| 0 | 40.8 | 45.6 | 50.7 |
| 0.03 | 54.8 | 62 | 57.1 |
| 0.06 | 175.6 | 106.1 | 68.1 |
| 0.1 | >600 | 224.9 | 92.6 |
| 0.2 | >600 | >600 | 181.8 |

| LMWH | IXa CLOT | Xa CLOT | XIa CLOT |
|---|---|---|---|
| 0 | 45.5 | 45.5 | 49.4 |
| 0.03 | 65.5 | 62.5 | 54.5 |
| 0.06 | 156.3 | 109.8 | 65.4 |
| 0.1 | 418.6 | 211.5 | 76.4 |
| 0.2 | >650 | 614.1 | 121.2 |
| 0.4 | >650 | >650 | 326.4 |

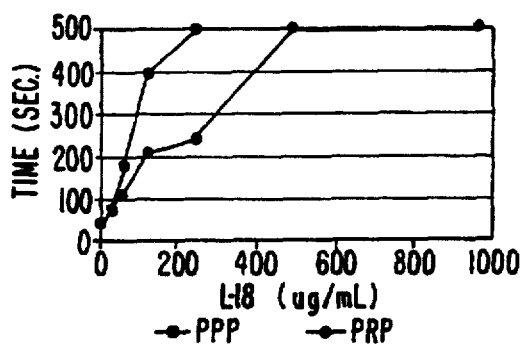
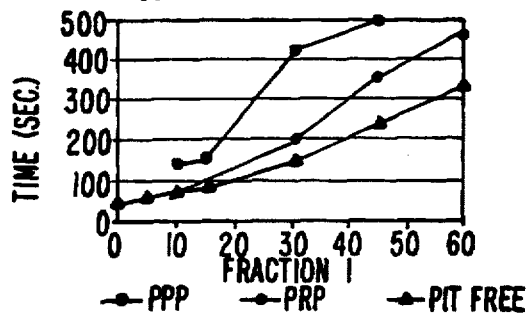
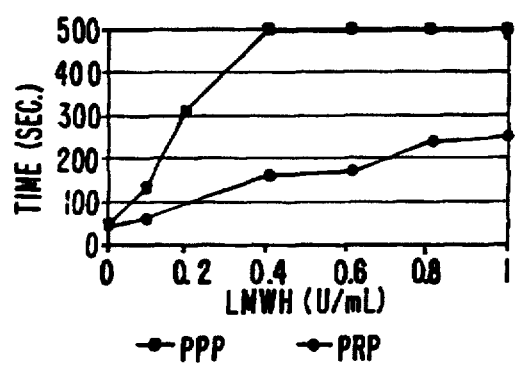
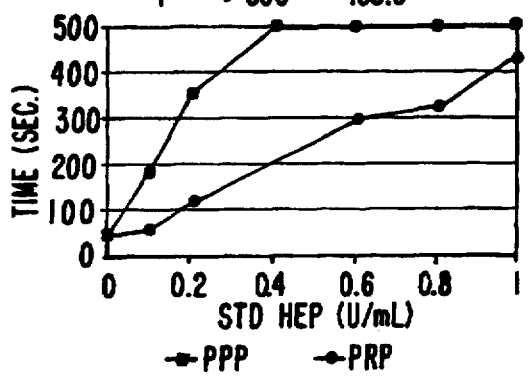
FIG. 45.

| FRACTION I | PPP | PRP | PIT FREE |
|---|---|---|---|
| 0 | 5 | 3.3 | 4.45 |
| 30 | 7 | 5.15 | 5.4 |
| 60 | 9.2 | 5.3 | 9.15 |
| 120 | 15.15 | 9.2 | 11.2 |
| 240 | 46 | 14 | 21.3 |
| 480 | 131 | 24.45 | >180 |

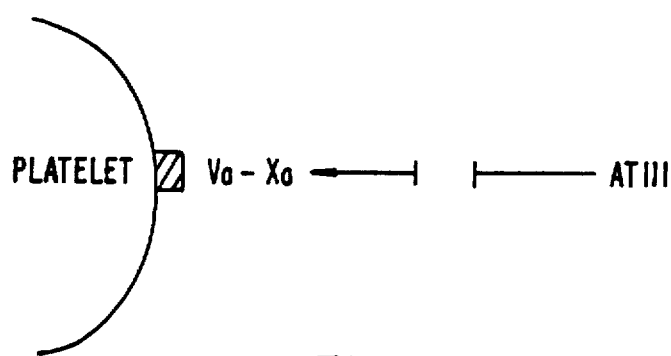
FIG. 48.
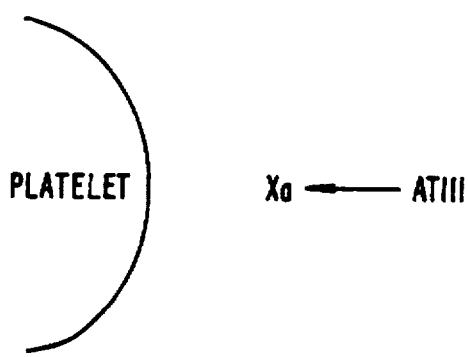
FIG. 49.
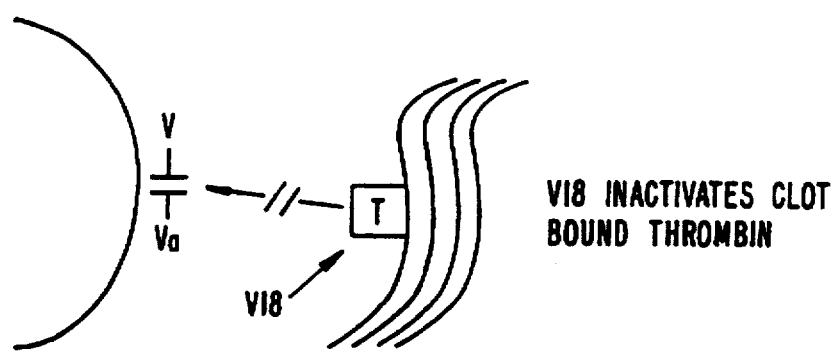
VI8 INACTIVATES CLOT BOUND THROMBIN
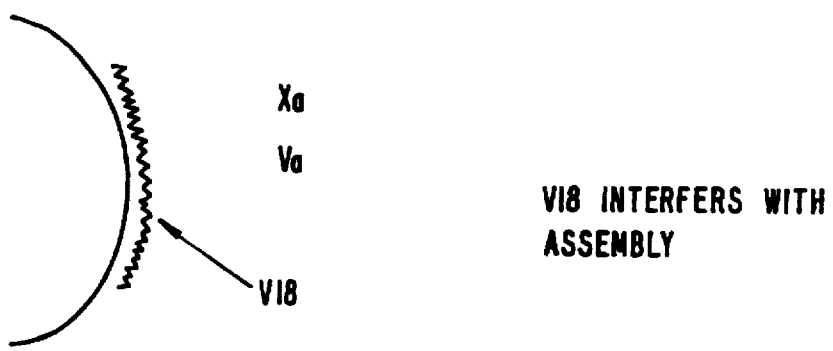
VI8 INTERFERS WITH ASSEMBLY
FIG. 50.

COMPOSITIONS AND METHODS FOR INHIBITING THROMBOGENESIS

This application is a continuation-in-part of Ser. No. 08/540,324, filed Oct. 6, 1995, now U.S. Pat. No. 5,744,457, which is a continuation-in-part of Ser. No. 08/412,332, filed Mar. 31, 1995, now abandoned, the teachings of which are incorporated herein by reference.

FIELD OF THE INVENTION

The present invention relates generally to compositions and methods for the treatment of cardiovascular disease. More particularly, the present invention relates to modifying thrombus formation and growth by administering an agent capable of selectively inactivating thrombin which is bound either to fibrin in a clot or to some other surface, but which has only minimal inhibitory activity against free thrombin, i.e., fluid-phase thrombin. The invention also relates to heparin cofactor II-specific (HCII) catalytic agents which, inter alia, activate HCII mediated inhibition of thrombin. The activity of the HCII-specific catalytic agents of the present invention allows them to inactivate fibrin-bound thrombin in a patient at concentrations which produce minimal inactivation of free thrombin, thereby diminishing the risk of bleeding. This is a surprising property of the HCII-specific catalytic agents of the present invention since other anticoagulants typically have either a reduced ability to inactivate fibrin-bound thrombin compared to free thrombin (e.g., heparin, dermatan sulfate and low molecular weight heparins), or a substantially equal ability to inactivate fibrin-bound thrombin and free thrombin (e.g., hirudin and its derivatives, and inhibitors of the active site thrombin inhibitors).

BACKGROUND OF THE INVENTION

Thrombosis is a pathological manifestation of the clotting cascade in blood vessels. The clotting cascade is a complex biological process which results in the formation of a clot or thrombus composed of platelets and fibrin. Thrombin is bound to fibrin in the clot where it is catalytically active and able to amplify its production over 1000-fold by activating clotting factors in the surrounding blood. The ability of blood to generate thrombin is fundamental to the prevention of excessive bleeding at wound sites (hemostasis). Thrombin is important in hemostasis because it stimulates platelet aggregation and fibrin formation when a blood vessel is severed. Therefore, an ideal anti-thrombin would be an agent which can pacify the clot by inactivating fibrin-bound thrombin at concentrations which do not produce abnormal bleeding resulting from inhibition of thrombin production in the general circulation.

Thrombosis, which can complicate atherosclerosis, can cause partial or total occlusion of the affected blood vessel, thereby leading to a number of important cardiovascular complications, including unstable angina, acute myocardial infarction (heart attack), cerebral vascular accidents (stroke), pulmonary embolism, deep vein thrombosis and arterial thrombosis. Such diseases are a major cause of disability and mortality throughout the world, but particularly in Western societies. Moreover, thrombin and, in particular, surface-bound thrombin play a role in thrombus formation in cardiac bypass circuits, after angioplasty and during and after thrombolytic therapy for acute myocardial infarction. Therefore, patients undergoing these procedures must be treated with very high doses of heparin to prevent thrombosis. Although these high doses of heparin may effectively prevent clotting, they can give rise to serious bleeding complications.

The clot or thrombus, which forms as a result of activation of the clotting cascade, contains fibrin, platelets and numerous other blood components. Thrombin bound to fibrin remains active and causes growth of the clot by continued cleavage of fibrinogen and activation of platelets and other coagulation factors, such as factor V and factor VIII. Moreover, unlike free thrombin which is readily inactivated by naturally occurring anti-thrombins (e.g., antithrombin III (ATIII)), clot-bound thrombin is protected from inactivation. As a result, the clot acts as a reservoir for active thrombin which triggers further clot growth. In addition, thrombin also induces smooth cell proliferation and, thus, may be involved in proliferative responses, such as graft-induced atherosclerosis and restenosis after angioplasty or atherectomy.

Because thrombin is critical to thrombus formation, the use of thrombin inhibitors for treating thrombosis and thrombotic complications has long been proposed. A number of partially effective inhibitors have been in use for years. Heparin, for example, can be used as an anticoagulant and anti-thrombin agent to inhibit fibrin formation, platelet aggregation and thrombus formation. Heparin, however, has a number of limitations. For example, it has biophysical limitations because it acts as an anticoagulant by activating ATIII and, thus, it is relatively ineffective at inactivating fibrin-bound thrombin at safe doses, thereby allowing the continued growth of thrombus mediated by thrombin bound to fibrin in the pre-existing thrombus. In addition, the doses required to produce an anti-thrombotic effect are quite unpredictable and, therefore, the dosage must be monitored closely. Low molecular weight heparins (LMWH) can also be used as anticoagulants and anti-thrombin agents to inhibit fibrin formation, platelet aggregation and thrombus formation. LMWHs act by activating ATIII and, as such, have the same biophysical limitations as heparin. However, LMWHs produce a more predictable anticoagulant effect than heparin. Thus, both heparin and LMWH have the limitation of not readily inactivating surface-bound thrombin. The consequences of this are (a) high concentrations are needed to achieve an anti-thrombin effect which can lead to excessive bleeding, and (b) once the agents are cleared from the circulation, the surface-bound thrombin can reactivate clotting.

Inactivation of clot-bound thrombin may be achieved with another set of compounds known as the direct thrombin inhibitors. Such inhibitors include hirudin and its derivatives, and inhibitors of the active site of thrombin, such as argatroban and PPACK (D-phenylalanyl-L-propyl-L-arginyl chloromethyl ketone). Hirudin is an anti-thrombin substance extracted from the salivary glands of leeches. Related compounds include hirulog which is a small, synthetic analog of hirudin. While these drugs are able to inhibit clot-bound thrombin, they have the following limitations. First, they do not typically inactivate clot-bound thrombin selectively, but do so at the same concentrations which are required to inhibit free thrombin. Secondly, the inactivation of thrombin is generally stoichiometric and, thus, unless very high concentrations are used, the inhibitory effect can be overcome by the large amounts of thrombin that are generated at sites where surface-bound thrombin accumulates (e.g., on bypass circuits, or at sites of arterial or venous thrombosis). As a result of the above two limitations, high concentrations of direct thrombin inhibitors (e.g., hirudin) must typically be administered to interact with and inhibit the free thrombin generated by clot-bound thrombin. Such high inhibitor concentrations can, however, cause unwanted bleeding. Moreover, direct thrombin inhibitors (e.g., hirudin, its analogs and LMW active site thrombin inhibitors, such as argatroban) are generally reversible and, thus, the inhibitory effect is lost when the drugs are cleared from the blood. Unfortunately, this reversible inhibition can lead to rebound activation of coagulation.

In addition, inactivation of clot-bound thrombin may be achieved with a third class of compounds which bind reversibly or irreversibly to the active, i.e., catalytic, site of thrombin. PPACK is an example of an irreversible active site inhibitor. Such inhibitors, however, generally lack sufficient specificity for thrombin and, thus, have questionable safety. Moreover, such inhibitors have the same limitation as hirudin in that they typically have equal activity against clot-bound and free thrombin. This is problematic because evidence indicates that total inhibition of free thrombin using irreversible active site inhibitors may lead to excessive bleeding.

For the foregoing reasons, there is a need for improved compositions and methods that are useful, for example, for inhibiting thrombogenesis associated with cardiovascular disease. In particular, it would be desirable to provide compositions and methods capable of reducing or eliminating fibrin-bound thrombin activity from existing thrombi within the vascular system. Such elimination or reduction of clot-bound thrombin should be essentially irreversible so that clot accretion will not substantially resume after administration of the treating agent is stopped. As such, compositions and methods are needed which are able to inactivate thrombin within the clot or thrombus with an agent that does not strongly inactivate free thrombin, since such an agent would not adversely affect bleeding control (hemostasis). The present invention fulfills these and other needs.

Hirudin derivatives for blocking the active site of thrombin are described in U.S. Pat. Nos. 5,240,913 and 5,196,404. A bifunctional anti-thrombotic composition which includes both a glycoprotein IIb/IIIa inhibitory domain and a thrombin inhibitory domain is described in WO 92/10575. Peptide analogs of glycoprotein IIIa for thrombogenesis inhibition are described in WO 90/00178. Inhibitors of factor X and/or Xa are described in U.S. Pat. Nos. 5,239,058 and 5,189,019, and PCT publications WO 93/09803, WO 92/04378 and WO 92/01464. Inhibitors of factors VII and/or VIII are described in U.S. Pat. Nos. 5,223,427 and 5,023,236 and WO 92/06711. Platelet anti-adhesives and related antibodies are described in WO 92/08472. For a review of the structure and function of thrombin, see, Stubbs and Bode, *Thrombosis Research* 69:1–58 (1993). For a review of the limitations of heparin and the potential advantages of new anticoagulants as anti-thrombotics, see, Hirsh, *Circ.* 88:I-C (1993).

In addition, numerous modified heparin compositions, as well as other glycosaminoglycans and their derivatives, have been developed. For example, U.S. Pat. Nos. 5,296,471, 5,280,016 and 5,314,876 describe the desulfation of heparin, periodate oxidation of heparin/heparan sulfates followed by reduction of resulting aldehyde groups, and high molecular mass N,O-sulfated heparosans, respectively. Low molecular weight heparin fractions have been used for several years (see, Boneu, et al., *Thrombosis Research* 40:81–89 (1985)). More recently, various dermatan sulfates have been developed and their interactions with heparin cofactor II studied (see, Mascellani, et al., *Thrombosis Research* 74:605–615 (1994), and Sheehan, et al., *J. Biol. Chem.* 289:32747–32751 (1994)).

SUMMARY OF THE INVENTION

The present invention provides compositions and methods for the treatment of cardiovascular diseases. The invention relates to, inter alia, agents capable of selectively inactivating clot-bound thrombin. More particularly, in one aspect, the present invention provides heparin cofactor II-specific (HCII) catalytic agents capable of selectively inactivating thrombin which is bound either to fibrin in a clot or to some other surface, but which has only minimal inhibitory activity against free thrombin. The selective activity of the HCII-specific catalytic agents of the present invention allows them to inactivate fibrin-bound thrombin in a patient at concentrations which produce minimal inactivation of free thrombin, thereby diminishing the risk of bleeding. Preferably, the inactivation of fibrin- or surface-bound thrombin is essentially irreversible so that clot accretion will not substantially resume after such HCII-specific catalytic agents (i.e., activating agents which activate, catalyze or induce HCII mediated inactivation of fibrin-bound thrombin) are cleared from the blood.

In one embodiment, the agents of the present invention are low molecular weight heparin (LMWH) preparations that have been modified so that they contain less than about 5% and, more preferably, less than about 3% of the anti-thrombin III (ATIII) catalyzing activity or, interchangeably, activating activity of unmodified LMWH or standard heparin, but more ATIII activating activity than dermatan sulfate. Moreover, because of their reduced chain length compared to standard heparin, the agents of the present invention have much less activity as catalysts of HCII-mediated inactivation of free thrombin than either standard heparin or dermatan sulfate. As such, the agents of the present invention have very weak activity when assayed against free thrombin in a thrombin clotting time assay and would not have been predicted to be effective anti-thrombotic agents. Quite surprisingly, however, the agents of the present invention are able to effectively catalyze HCII-mediated inactivation of surface-bound thrombin, e.g., fibrin-bound thrombin or, interchangeably, clot-bound thrombin.

Surface-bound thrombin is typically inactivated through the formation of a covalent, irreversible thrombin-HCII complex. Thus, in contrast to typical anti-thrombins and other anticoagulants (e.g., dermatan sulfate, heparin, low molecular weight heparins (LMWHs), hirudin and other direct thrombin inhibitors), the HCII-specific catalytic agents of the present invention have the ability to selectively and, preferably, irreversibly inactivate fibrin-bound thrombin without having major inhibitory effects against fluid-phase thrombin. Without being bound to a given theory, this ability is explained by the observation that the agents of the present invention produce a conformational change in HCII which enables it to bind thrombin effectively when the enzyme is immobilized on a surface, but which lacks the size to bind thrombin effectively when it is free in the fluid phase.

The agents of the present invention can be used in various methods, for example, to modify thrombus formation in a patient without inducing a clinically unsafe increase in systemic bleeding. Such methods generally comprise administering to a patient a pharmacologically acceptable dose of an agent capable of inactivating clot-bound thrombin with only minimal inactivation of free thrombin. The agents are preferably characterized by a specific anti-factor IIa activity mediated by heparin cofactor II of about 2 to about 5 units/mg in an anti-factor IIa assay, an antithrombin III catalyst specific activity of about 0.2 to about 1.5 units/mg in an anti-factor Xa assay, and a solubility in aqueous media ranging from about 150 to about 1,000 mg/ml. Moreover, such agents have an anticoagulant effect which is contributed to by both an HCII- and ATIII-mediated mechanism, and by a mechanism which is independent of both HCII and ATIII. In addition, the agents are preferably polyanionic carbohydrates of less than about 24 monosaccharide units, typically being heparin preparations having molecular weights of between about 3,000 and 8,000 Daltons (±1,000 Daltons).

The present invention includes heparin preparations which can be prepared from heparin using a variety of techniques. In one embodiment, heparin, i.e., standard, unfractionated heparin, is first reduced in molecular size by chemical depolymerization and the fractions with molecular weights ranging from 3,000 to 8,000 Daltons (±1,000 Daltons) are isolated and pooled. In a presently preferred embodiment, heparin is depolymerized using nitrous acid. Therafter, the resulting low molecular weight heparin is chemically modified to reduce its affinity for antithrombin III. This can be accomplished chemically or, alternatively, through the use of an antithrombin III affinity column. In a presently preferred embodiment, this is accomplished chemically by an oxidation reaction followed by a reduction reaction. In this preferred embodiment, the resulting low affinity, low molecular weight heparin is a mixture of heparin molecules having a native sugar (e.g., a uronic acid residue) as the nonreducing terminal and a 2,5-anhydromannitol residue as the reducing terminal, and having molecular weights ranging from about 3,000 to about 8,000 Daltons. In this embodiment, it is believed that the reduction in molecular size together with the reduction in ATIII activating activity endows the agents of the present invention with their ability to selectively inactivate clot-bound thrombin with only minimal inactivation of free thrombin.

As an alternative to being heparin preparations, the agents of the present invention can be, for example, negatively charged polysaccharides other than heparin, negatively charged polyanions, electronegative organic molecules with an affinity for HCII, and the like. Such substances will typically bind to HCII with an affinity of at least $10^{-6}$M, preferably at least about $10^{-8}$M or stronger, but with weak affinity for thrombin, preferably weaker than about $10^{-6}$M.

As desired, and depending on the use, pharmaceutical compositions useful for inhibiting thrombogenesis without substantially inhibiting normal coagulation in a patient can be prepared, the compositions comprising:

i) about 90 to about 99.9 weight percent of an agent which is capable of selectively inhibiting clot-bound thrombin, especially an HCII-specific catalytic agent, that has minimal affinity for, or is essentially devoid of, ATIII binding affinity and is capable of displacing and inactivating fibrin-bound thrombin; and ii) about 0.1 to about 10 weight percent of an ATIII catalytic agent or, interchangeably, an ATIII activating agent, such as heparin or low molecular weight heparin (LMWH), capable of inactivating fluid phase thrombin.

In a presently preferred embodiment, the HCII catalytic activity or, interchangeably, the HCII activating activity of the, optionally blended, composition is about 2 to 5 units/mg and, more preferably, about 3 to 4 units/mg.

In another embodiment, the present invention provides a method for inhibiting clot-bound thrombin and fluid-phase thrombin in a patient without inducing a clinically unsafe increase in systemic bleeding, the method comprising the step of administering to the patient a pharmacologically acceptable dose of (i) an HCII-specific catalytic agent capable of inactivating clot-bound thrombin, the HCII-specific catalytic agent having minimal affinity for anti-thrombin III (ATIII) and a heparin cofactor II specific activity against heparin cofactor II of about 2 to about 5 units/mg in an anti-factor IIa assay; and (ii) an ATIII catalytic, i.e., activating, agent capable of inactivating fluid-phase thrombin. ATIII activating agents suitable for use in this method include, but are not limited to, heparin and low molecular weight heparin. In this method, the HCII-specific catalytic agent and the ATIII catalytic agent, i.e., ATIII activating agent, can be administered to the patient either simultaneously or sequentially. When administered to the patient simultaneously, the HCII-specific catalytic agent and the ATIII catalytic agent can be administered as a single solution or compound or, alternatively, as two different solutions or compounds.

In another embodiment, the present invention provides a product comprising (i) an agent of the invention capable of inactivating clot-bound thrombin; and (ii) an ATIII catalytic agent capable of inactivating fluid-phase thrombin as a combined preparation for simultaneous, separate or sequential use for inhibiting clot-bound thrombin and fluid-phase thrombin in a patient, preferably without inducing a clinically unsafe increase in systemic bleeding. ATIII catalytic agents suitable for use in this product include, but are not limited to, heparin and low molecular weight heparin. In this product, the thrombin inactivating agent and the ATIII catalytic agent can be for administration to the patient simultaneously. When administered to the patient simultaneously, the thrombin inactivating agent and the ATIII catalytic agent can be administered as a single solution or compound or, alternatively, as two different solutions or compounds.

Preferred agents of the invention are obtainable from heparin. One class of products included in the invention comprises such preferred agents and, as a separate sub-class, the heparin preparations of the present invention, which products in both sub-classes have non-sulfated uronic acid residues in open-ring form and are substantially free of aldehyde groups. Exemplary members of the class have about 30% of their uronic acid residues in open ring form. Another class of such preferred agents and heparin preparations comprises products having a native sugar (e.g., a uronic acid residue) as the nonreducing terminal and a 2,5-anhydromannitol residue as the reducing terminal. Some particularly preferred products belong to both the aforesaid classes.

Another aspect of the invention resides in a polyanionic carbohydrate capable of selectively inactivating clot-bound thrombin in favor of free thrombin obtainable from heparin, having its non-sulfated uronic acid residues in open-ring form, and substantially free of aldehyde groups.

Also provided by the invention is a product capable of selectively inhibiting clot-bound thrombin, an HCII-specific catalytic agent obtainable by:

(i) depolymerizing standard unfractionated heparin by nitrous acid depolymerization;

(ii) oxidizing the depolymerized heparin with sodium periodate in an aqueous medium for 24 hour at 4° C., and stopping the oxidation reaction by the addition of excess ethylene glycol followed by extensive dialysis against distilled water using dialysis tubing with a 500 MW cut off.

(iii) reducing the oxidized product by the addition of sodium borohydride and, after allowing the reaction mixture to stand for 25 hours at 23° C., adjusting the pH of the reaction mixture to 3.0 with HCl to destroy excess borohydride then quickly increasing the pH to 7.0 by the addition of NaOH;

(iv) dialyzing the resultant produce extensively against distilled water; and (v) recovering the product by lyophilization; and optionally (vi) passing the produce over an anti-thrombin III affinity column, the product obtained having the following properties:
molecular weight of from 3,000 to 8,000 (±1,000)
specific activity of about 2 to about 5 anti-Factor IIa units/mg
specific activity of les than about 1.5 antiThrombin IIa units/mg.

In a further aspect, there is provided a process for preparing an HCII-specific catalytic agent having a native non-reducing sugar as one end group and a 2,5-anhydromannitol non-reducing sugar as the other end group, said process comprising:

(i) depolymerizing unfractionated heparin;

(ii) oxidizing the resultant low molecular weight heparin; and (iii) reducing the oxidized, low molecular weight heparin; wherein the process optionally includes additional purification or other procedures to obtain said HCII-specific catalytic agent.

The products and agents of the invention are preferably for pharmaceutical use. The invention therefore includes the use for the manufacture of a medicament for the treatment of a cardiovascular disease of any of the products or agents of the invention, such as, for example, an agent for activating HCII mediated inhibition of thrombin to the exclusion of significant ATIII mediated inhibition of thrombin. Other products and agents of the invention which may be so used include the HCII-specific catalytic agents, LMWH preparations, polyanionic carbohydrates and products obtainable as aforesaid and product V18 described in the Examples (or a substantially similar product to V18), as well as substances having substantially the same characteristics or inhibitory or pharmacological properties as the aforesaid products and agents.

The invention further includes the use for the manufacture of a medicament for the treatment of thrombosis by prophylaxis or therapy of a heparin derivative having its non-sulfated uronic acid residues in open-ring form and substantially free of aldehyde groups.

In addition to the foregoing, pharmaceutical compositions are provided comprising an agent or product which binds to HCII and allows it to interact with a non-fibrin-binding site on thrombin. The present invention further provides pharmaceutical compositions comprising an HCII-specific catalytic agent and an ATIII catalytic agent, i.e., and ATIII activating agent, and compositions comprising an agent for selectively inactivating surface-bound or clot-bound thrombin and an inhibitor of thrombin in the fluid phase. Such pharmaceutical compositions, which may be in the form of blends, are useful for treating numerous cardiovascular conditions. In addition, such compositions are useful in conjunction with conventional thrombolytic treatments, such as the administration of tissue plasminogen activator (tPA), streptokinase, and the like, as well as with intravascular intervention, such as angioplasty, atherectomy, and the like.

A further understanding of the nature and advantages of the invention will become apparent by reference to the remaining portions of the specification and drawings.

BRIEF DESCRIPTION OF THE DRAWINGS

FIG. 27 illustrates the effects of Fraction 2 on the TCT (A), the APTT (B), and the factor Xa clotting time (Xa clot time) (C) in normal plasma (-+-), ATIII-deficient plasma (-⊟-) and HCII-deficient plasma (-■-).

FIG. 45 illustrates the effect of platelets on the anticoagulant activity of V18 (A), Fraction 1 of V18 (B), LMWH (C) and SH (D).

FIG. 48 illustrates the assembly of Factor Xa on phospholipid surface.

FIG. 49 illustrates the consequences of impaired assembly.

FIG. 50 illustrates the mechanism of impaired assembly.

DETAILED DESCRIPTION OF THE INVENTION AND PREFERRED EMBODIMENTS

Figure 1:
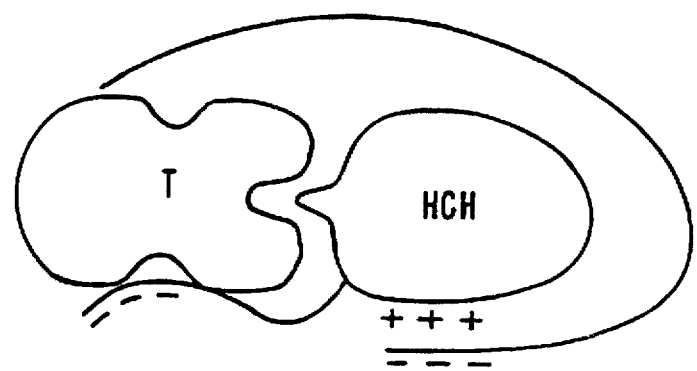
FIG. 1 illustrates the proposed mechanism by which heparin binds to HCII and facilitates approximation between HCII and thrombin so that an irreversible covalent bond can form between the catalytic center of thrombin and a Leu-Ser bond on HCII.

The present invention provides compositions and methods for inactivating thrombin bound to fibrin within a thrombus or clot, whereby the ability of clot-bound thrombin to catalytically promote further clot accretion is substantially diminished or eliminated. The compositions and methods of the present invention are particularly useful for preventing thrombosis in the circuit of cardiac bypass apparatus and in patients undergoing renal dialysis, and for treating patients suffering from or at risk of suffering from thrombus-related cardiovascular conditions, such as unstable angina, acute myocardial infarction (heart attack), cerebrovascular accidents (stroke), pulmonary embolism, deep vein thrombosis, arterial thrombosis, etc. The present invention is not limited to such uses, however, and the compositions and methods described herein may find use in other in vitro and in vivo situations whenever it is desirable to inhibit clot or thrombus accretion, or to promote clot or thrombus solubilization. For example, the compositions of the present invention may be used as an anti-coagulant for inhibiting thrombin-induced clotting in various in vitro studies, assays and the like.

"Proteoglycan," as used herein, includes reference to a protein to which is attached one or more glycosaminoglycan chains. Proteoglycans are polyanionic compounds that have properties that reflect both the protein and the glycosaminoglycan chains.

"Glycosaminoglycan," as used herein, includes reference to a polysaccharide composed of repeating disaccharide units. The disaccharides always contain an amino sugar (i.e., glucosamine or galactosamine) and one other monosaccharide, which may be a uronic acid (i.e., glucuronic acid or iduronic acid) as in hyaluronic acid, heparin, heparan sulfate, chondroitin sulfate or dermatan sulfate—or a galactose as in keratan sulfate. The glycosaminoglycan chain may be sulfated on either moiety of the repeating disaccharide. With the exception of hyaluronic acid, all glycosaminoglycans are covalently attached to a "core protein," i.e., they occur as proteoglycans.

"Heparin" (or, interchangeably, "standard heparin" (SH) or "unmodified heparin"), as used herein, includes reference to a mixture of polysaccharide chains composed of repeating disaccharides made up of a uronic acid residue (D-glucuronic acid or L-iduronic acid) and a D-glucosamine and residue. Many of these disaccharides are sulfated on the uronic acid residues and/or the glucosamine residue. Generally, heparin has a molecular weight ranging from about 6,000 Daltons to 20,000 Daltons, depending on the source of the heparin and the methods used to isolate it. The structural formula of the repeating disaccharide units of heparin is generally as follows:

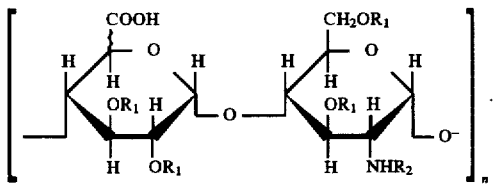

In the above formula, the "squiggle" bond at C5–C6 of the uronic acid indicates that the uronic acid may be either D-glucuronic acid (carboxyl up) or L-iduronic acid (carboxyl down). In addition, $R_1$ may be either H or $SO_3$, and $R_2$ may be H, Ac (acetyl) or $SO_3$.

"Low Molecular Weight Heparin" (LMWH), as used herein, includes reference to a heparin preparation having a molecular weight of about 3,000 Daltons to about 8,000 Daltons.

"Low Affinity Heparin" (LAH) (or, interchangeably, "low affinity standard heparin" (LASH)), as used herein, includes reference to a heparin preparation which binds to antithrombin III (ATIII) with an affinity of about $10^6$M, preferably weaker than about $10^{-5}$M.

"Low Affinity-Low Molecular Weight Heparin" (LA-LMWH), as used herein, includes reference to a heparin preparation having a molecular weight of about 3,000 Daltons to about 8,000 Daltons and which binds to ATIII with an affinity of about $10^{-6}$M, preferably weaker than about $10^{-5}$M. The LA-LMWH preparation can be a mixture of heparin molecules having molecular weights ranging from 3,000 to 8,000 Daltons (±1,000 Daltons). This mixture of LA-LWMH molecules is generally referred to herein as V18 or, interchangeably, as L18. Alternatively, the mixture of heparin molecules can be separated into its various components using, for example, gel exclusion chromatography. The LA-LMWH mixture can be arbitrarily separated into three LA-LWMH fractions by gel exclusion chromatography. Fraction 1 has a mean molecular weight of about 8,000 Daltons, Fraction 2 has a mean molecular weight of about 5,000 Daltons and Fraction 3 has a mean molecular weight of about 3,000 Daltons.

A "heparin preparation," as used herein, includes reference to a preparation prepared from standard, unfractionated heparin. In a preferred embodiment, the HCII-specific catalytic agents of the present invention are modified heparins which have been prepared from standard, unfractionated heparin using the following chemical reactions: (1) nitrous acid depolymerization of unfractionated heparin to yield low molecular weight heparin (LMWH); (2) oxidation of the resulting LMWH to open the ring structures the unsulfated uronic acid moieties using, for example, sodium periodate; and (3) reduction of the oxidized LMWH to reduce the aldehydes (to alcohols) formed during the depolymerization and oxidation steps using, for example, sodium borohydride.

"Heparan Sulfate" (HS), as used herein, includes reference to a glycosaminoglycan which contains a disaccharide repeat unit similar to that of heparin, but which has more N-acetyl groups, fewer N-sulfate groups, and a lower degree of O-sulfate groups.

"Dermatan Sulfate" (DS), as used herein, includes reference to a heterogeneous glycosaminoglycan that contains disaccharide repeat units consisting of N-acetyl-D-galactosamine and D-glucuronic acid and disaccharide repeat units consisting of N-acetyl-D-galactosamine and L-iduronic acid. The uronic acids are present with variable degrees of sulfation.

"Hirudin," as used herein, includes reference to an antithrombin substance that is extracted from the salivary glands of leeches. "Hirulog," as used herein, includes reference to a small, synthetic analog of hirudin.

"Monosaccharide," as used herein, refers a polyhydroxy alcohol containing either an aldehyde or a ketone group, i.e., a simple sugar. Monosaccharide includes reference to naturally occurring simple sugars as well as simple sugars which have been chemically modified. Modified monosaccharides include, but are not limited to, monosaccharides that have increased or decreased sulfation or which have modified carboxyl, amino or hydroxyl groups. Monosaccharides may be chemically modified by: N-desulfation (see, e.g., Inoue, Y., et al., Carbohydrate Res. 46, pp. 87–95 (1976)); N-resulfation (see, e.g., Lloyd, A. G., et al., Biochem. Pharmacol. 20, pp. 637–648 (1971)), N-acetylation (see, e.g., Danishefsky, I., et al., Biophys. 90, pp. 114–121 (1970)); N-succinylation (see e.g., Nagasawa, K., et al., J. Biochem. 81, pp. 989–993 (1977)); N-deacetylation (see, e.g., Dimitriev, B. A., et al., Carbohydr. Res. 40, pp. 365–372 (1975)); O-desulfation (see, e.g., Jacobson, L, et al., J. Biol. Chem. 255, pp. 5084–5100 (1980); carboxy reduction; methylation of free hydroxyl or amino groups, etc.

"Polysaccharide," as used herein, refers a linear or branched polymer of more than 10 monosaccharides that are linked by means of glycosidic bonds.

"Polyanion," as used herein, refers a molecule that possesses a large number of negative charges. "Polyanionic carbohydrates," as used herein, includes reference to carbohydrates that possess a large number of negative charges.

A "heparin additive," as used herein, includes reference to heparin or a heparin-like compound which is mixed with an agent of the present invention prior to patient administration. In a presently preferred embodiment, the heparin additive is either unfractionated heparin or the lowest third molecular weight fraction isolated from unfractionated heparin.

"Vicinal alcohol groups," as used herein, includes reference to two hydroxyl groups on adjacent carbon atoms. More particularly, "vicinal alcohol groups" is used herein to refer to the two hydroxyl groups on the C2 and C3 carbon atoms of the heparin preparations of the present invention.

"Oxidizing agent" or, interchangeably, "oxidant," as used herein, includes reference to a substance that (1) yields oxygen readily, (2) removes hydrogen from a compound, or (3) attracts negative electrons. Suitable oxidizing reagents include, but are not limited to, sodium periodate and, under reaction conditions known to those of skill in the art, lead tetraacetate.

"Reducing agent" or, interchangeably, "reducer," as used herein, includes reference to a substance that is readily oxidized by reducing another substance. Suitable reducing agents include, but are not limited to, sodium borohydride, other metal hydrides and, under reaction conditions known to those of skill in the art, lithium aluminum hydride.

"Affinity," as used herein, is expressed in terms of the dissociation constant ($K_d$). As such, each time an affinity is mentioned, it is referring to the $K_d$, not the $K_a$.

"A clinically unsafe increase in systemic bleeding," as used herein, includes, in preferred embodiments, reference to an activated clotting time of less than 400 seconds and a thrombin clotting time of less than 100 seconds even when the agent is used at the highest effective concentrations.

The "anti-factor IIa assay," as used herein, is an HCII catalytic assay that is carried out as follows: a fixed amount of human thrombin is added to plasma containing a chromogenic synthetic thrombin substrate. After incubation with the compound of interest, the amount of residual thrombin is determined by measuring the absorbance at 405 nm.

The "anti-factor Xa assay," as used herein, is an ATIII catalytic assay that is carried out as follows: a fixed amount of factor Xa is added to plasma containing a chromogenic synthetic factor Xa substrate. After incubation with the compound of interest, the amount of residual factor Xa activity is determined by measuring the absorbance at 405 nm.

The "Hanging Clot Assay," as used herein, includes reference to an assay used to examine the inhibitory effect of agents against fluid-phase and clot-bound thrombin activity. Generally, to determine the inhibitory effect against fluid-phase thrombin activity, α-thrombin (0.2–4.0 nM) is incubated with citrated plasma for 60 min at 37° C. in the presence or absence of heparin at the concentrations indicated. At the end of the incubation period, the plasma levels of Fibrinopeptide A (FPA) are determined, and the percent inhibition of FPA generation is then calculated for each inhibitor concentration. To determine the inhibitory effect against clot-bound thrombin activity, washed fibrin clots are incubated in citrated plasma for 60 min at 37° C. in the presence or absence of varying concentrations of heparin. At the end of the incubation period, the plasma levels of FPA are determined, and the percent inhibition of clot-induced FPA generation is then calculated for each inhibitor concentration.

A "filter-containing plate assay" (or, interchangeably, "filtration based assay"), as used herein, includes reference to an assay used to test the ability of a compound to displace and inactivate thrombin bound to fibrin. This assay is carried out using the protocol set forth in the examples.

It has been demonstrated that the fibrin-binding site on thrombin (anion-binding exosite 2) is distinct from the fibrinogen-binding site on thrombin (anion-binding exosite 1). That is, when thrombin is bound to fibrin, as is the case in clot or thrombus matrices, the fibrin-binding site will be occupied, while the fibrinogen-binding site remains sterically available to bind fibrinogen and orient the bound fibrinogen for interaction with the thrombin catalytic site which promotes the conversion of fibrinogen to fibrin. The enzyme's active site and exosite 1 are available to bind and cleave other substrates as well, including factor V, factor VIII and the thrombin receptor on platelets.

Thus, it is possible to disrupt or interfere with binding between the fibrin-binding site on the thrombin and/or the thrombin-binding site on the fibrin in order to release thrombin from the clot or thrombus into a surrounding aqueous environment, usually into blood in the vascular environment. While fibrin-bound thrombin in the clot or thrombus is protected from inactivation by heparin and endogenous anti-proteinases, thrombin released from the clot or thrombus becomes susceptible to inactivation from endogenous anti-proteinases and/or appropriate drug therapies.

It is known that free thrombin, i.e., fluid-phase thrombin, is irreversibly inactivated by two plasma inhibitors, antithrombin III (ATIII) and heparin cofactor II (HCII), with ATIII being the primary inhibitor. Both of these inhibitors exhibit a markedly increased activity in the presence of certain classes of sulfated polysaccharides. It has been found that the activity of ATIII is catalyzed by heparin and by low molecular weight heparin (LMWH), whereas the activity of HCII is catalyzed by high concentrations of heparin and by dermatan sulfate. However, although heparin (but not LMWH) is a potent catalyst of HCII, the predominant effect of heparin at therapeutic concentrations is as a catalyst of ATIII, because heparin has a higher affinity for ATIII than HCII at such concentrations. Moreover, the plasma concentration of ATIII is more than twice that of HCII (2.4 μM and 1 μM, respectively) and, thus, heparin catalyzes both ATIII and HCII only when it is administered in very high concentrations.

HCII inactivates thrombin by acting as a pseudo-substrate for the enzyme. Thrombin cleaves HCII, resulting in the formation of a covalent enzyme-inhibitor complex. The formation of this complex is very slow in the absence of a catalyst. However, in the presence of dermatan sulfate or heparin, the rate of HCII-mediated inhibition of thrombin increases by about 2,000 fold (See, Tollefson, *Ann. NY Acad. Sci.* 714:21–31 (1994)).

A model for HCII catalysis by dermatan sulfate or heparin involves a two-step process. First, the sulfated polysaccharide binds to a positively charged region on HCII and causes unfolding of the N-terminal, negatively charged segment of the HCII molecule (FIG. 1). This electronegative N-terminal segment then interacts with the positively charged region on thrombin known as exosite 1. The interaction of the conformationally altered HCII with thrombin increases the rate of inhibition by approximately 50-fold. If the sulfated polysaccharide chain is sufficiently long, a second step occurs which markedly enhances the rate of HCII-mediated inactivation of thrombin. In this second step, the sulfated polysaccharide binds to the electropositive region on thrombin known as exosite 2. Sulfated polysaccharides that can bind to both the inhibitor and the enzyme effectively approximate HCII and thrombin, thereby increasing the rate of HCII-mediated inactivation of thrombin by about 2,000-fold.

The activity of the HCII-specific catalytic agents of the present invention is based, in part, on inactivating thrombin bound to fibrin without necessitating displacement. More particularly, the postulated mode of activity of the HCII-specific catalytic agents of the present invention is based, in part, on the following observations. First, because thrombin binds to fibrin via exosite 2, exosite 1 is available to interact with conformationally altered HCII. As a result, conformationally altered HCII can inactivate thrombin bound to fibrin without necessarily displacing it. Second, it has been discovered that certain sulfated polysaccharides, which are poor catalysts of HCII-mediated inactivation of thrombin in solution because they are of insufficient chain length to bind both HCII and thrombin, are still able to effectively catalyze the inactivation of fibrin-bound thrombin by HCII. Thus, the HCII-specific catalytic agents of the present invention are useful as selective inhibitors of clot-bound thrombin in vivo because they inactivate thrombin bound to fibrin without inducing a marked systemic anticoagulant state.

Without intending to be restricted to a particular theory, it is thought that this selective inhibition occurs because the requirements for catalysis, i.e., activation, of HCII-mediated inactivation of free thrombin are different from those needed for activation of HCII-mediated inactivation of fibrin-bound thrombin. Thus, in accordance with the present invention, polyanions have been identified that are more effective at inactivating fibrin-bound thrombin than free thrombin. These polyanions are unable to catalyze fully HCII-mediated inactivation of free thrombin either because they are of insufficient chain length, or because they lack the necessary negative charge to bind to both HCII and thrombin. Such agents, however, are able to inactivate fibrin-bound thrombin because, in theory, bridging (i.e., binding to both HCII and thrombin) is not a prerequisite for efficient HCII-mediated inactivation of thrombin when the enzyme is immobilized on the fibrin surface. Instead, conformational alteration of HCII by, for example, sulfated polyanions is sufficient to promote the inactivation.

Figure 2:
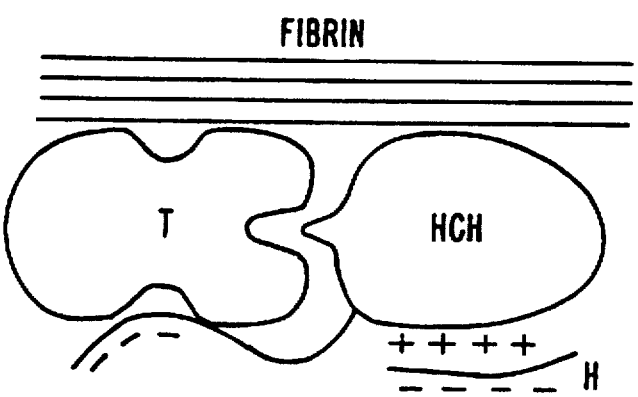
FIGS. 2 and 3 illustrate the proposed mechanism by which the HCII-specific catalytic agents of the present invention are able to have selective activity against surface-bound thrombin.
Figure 3:
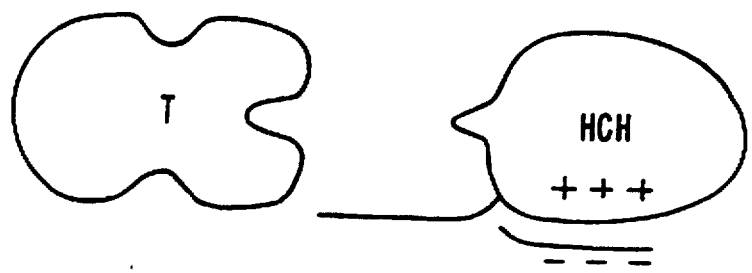

The ability of sulfated polysaccharides to bind to both HCII and thrombin is size dependent. Sulfated polysaccharides which contain less than about 24 monosaccharide units are typically of insufficient length to bind to thrombin and, hence, do not dramatically increase the rate of HCII-mediated thrombin inhibition. However, because these agents can still bind to HCII and induce a conformational change, they will increase the rate of thrombin inhibition to a modest extent. Moreover, when thrombin is bound to fibrin at exosite 2 and immobilized, the polysaccharide is not required to bind to thrombin and, thus, the clot-bound thrombin can be readily inactivated by HCII provided that the inhibitor has been modified by the low molecular weight polysaccharide (FIGS. 2 and 3). This is thought to be a possible mechanistic explanation for the selectivity of the HCII-specific catalytic agents of the present invention against clot-bound thrombin.

The compositions and methods of the present invention can provide for complete or near-complete inactivation of clot-bound or thrombus-bound thrombin, whereby thrombin-mediated amplification of coagulation is substantially inhibited or prevented. Usually, at least about 60% inhibition of clot- or thrombus-bound thrombin can be achieved, preferably at least about 90% inhibition, and more preferably at least about 95% inhibition (by "inhibition," in this context, it is meant that the thrombin activity is substantially, irreversibly inactivated so that the thrombin molecule cannot promote clot or thrombus formation or accretion; more generally, inhibition refers to a reduction in activity).

Several HCII catalyst assays or, interchangeably, HCII activating assays are well known to those of skill in the art. An example of such an HCII activating assay is the anti-factor IIa assay (see, Ofoso, *Blood* 64:742–747 (1984)). Other HCII activating assays include those described in U.S. patent application Ser. No. 08/175,211 (filed Dec. 27, 1993). Similarly, several ATIII catalyst assays or, interchangeably, ATIII activating assays are well known to those of skill in the art. An example of such an ATIII activating assay is the anti-factor Xa assay (see, Teien, et al., *Thromb. Res.* 8:413–416 (1976)). In addition, several anticoagulant assays are known to those of skill in the art, such as thrombin clotting time, factor Xa clotting time, partial thromboplastin time and activated clotting time. The foregoing assays are generally described in, e.g., *Low-Molecular-Weight Heparin in Prophylaxis and Therapy of Thromboembolic Diseases* (H. Bounameaux (ed.); Marcel Dekker, Inc.; New York. New York (1994)), the teachings of which are incorporated herein by reference for all purposes.

The products and agents of the invention will now be described in more detail, by way of example only, with illustrative reference to the HCII-specific catalytic agents of the present invention. The preferred properties described below in relation to such HCII-specific catalytic agents are applicable also to the agents and products of other aspects of the invention.

The HCII-specific catalytic agents of the present invention will preferably exhibit one or more of the following characteristics:

i) an HCII catalyst specific activity or, interchangeably, an HCII activating specific activity of about 2 to 5 units/mg in a chromogenic anti-factor IIa assay and, more preferably, about 3 to 4 units/mg;

ii) an ATIII catalyst specific activity or, interchangeably, an ATIII activating specific activity of about 0.2 to 1.5 units/mg in a chromogenic anti-factor Xa assay, preferably about 0.5 to about 1.3 units/mg and, more preferably, about 1 unit/mg;

iii) a solubility in aqueous media ranging from about 150 to about 1,000 mg/ml, preferably from about 200 to about 750 mg/ml and, more preferably, from about 400 to about 500 mg/ml;

iv) at concentrations which exert an anti-thrombic effect in vivo, an anticoagulant activity in plasma as measured by thrombin clotting time from 20 to 80 seconds (with a control of 20 seconds), preferably 25 to 45 seconds, and more preferably 30 seconds; and v) an anticoagulant effect which is contributed to by both an HCII- and ATIII-mediated mechanism, and by a mechanism which is independent of both HCII and ATIII.

The HCII-specific catalytic agents of the present invention are preferably glycosaminoglycans. More particularly, the HCII-specific catalytic agents are preferably polyanionic carbohydrates of about 10 to about 24 monosaccharide units and, more preferably, polyanionic carbohydrates of about 14 to about 20 monosaccharide units. Typically, the HCII-specific catalytic agents are heparin preparations having molecular weights ranging from about 3,000 to 8,000 Daltons (±1,000 Daltons). As such, in one embodiment, heparin is a preferred source of the HCII-specific catalytic agents of the present invention. Heparin, as previously explained, is a highly sulfated dextrorotary mucopolysaccharide comprised of D-glucosamine and D-glucuronic acid or L-iduronic residues. Generally, heparin has a molecular weight ranging from about 6,000 Daltons to 20,000 Daltons, depending on the source of the heparin and the methods used to isolate it. In a preferred embodiment, the HCII-specific catalytic agents of the present invention are heparin preparations which have been prepared from heparin using the following chemical reactions: (1) depolymerization of unfractionated heparin to yield LMWH; (2) oxidation of the resulting LMWH; and (3) reduction of the oxidized LMWH. It will be readily apparent to those of skill in the art that the order of these steps can be modified, e.g., unfractionated heparin can be oxidized, depolymerized and reduced or, alternatively, oxidized, reduced, depolymerized and reduced, provided the final step is a reduction step.

In addition to being heparin preparations, however, the HCII-specific catalytic agents of the present invention can be, for example, negatively charged polysaccharides other than heparin, negatively charged polyanions, electronegative organic molecules with an affinity for HCII, and the like. Such substances will typically bind to HCII with an affinity of at least $10^{-6}$M, preferably at least about $10^{-8}$M or stronger, but with weak affinity for thrombin, preferably weaker than about $10^{-6}$M.

In one embodiment, the HCII-specific catalytic agents of the present invention can have the following formula:

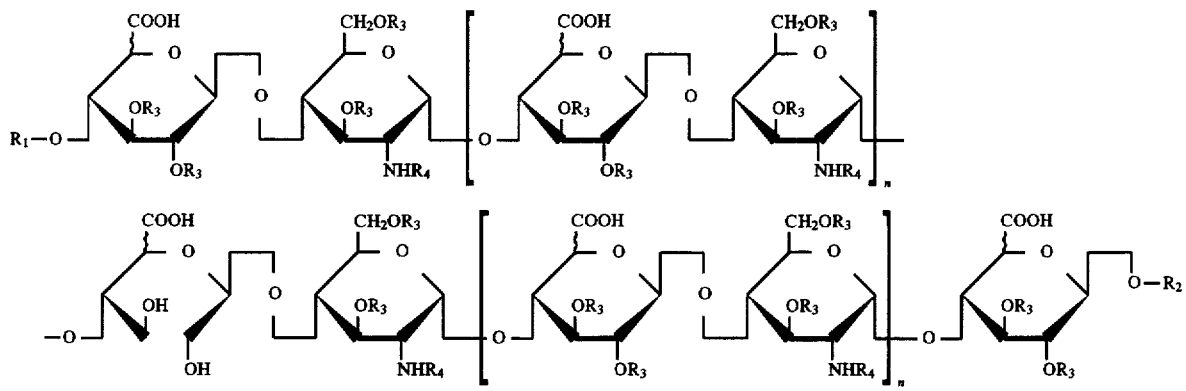

In the above formula, $R_1$ is a member selected from the group consisting of H, D-glucosamine acid residue, D-glucuronic acid residue and L-iduronic acid residue. $R_2$ is a member selected from the group consisting of H, D-glucosamine acid residue, D-glucuronic acid residue, L-iduronic acid residue and anhydromannitol. $R_3$, in the above formula, is a member selected from the group consisting of H and $SO_3^-$. Finally, $R_4$ is a member selected from the group consisting of H, $SO_3^-$ and $CH_3CO^-$. In the above formula, indexes "n" are independently selected and can have values ranging from 0 to about 14. The values of "n" are selected such that the HCII-specific catalytic agents of the present invention will have molecular weights ranging from about 3,000 Daltons to about 8,000 Daltons (±1,000 Daltons).

In another embodiment, the heparin-derived HCII catalytic agents of the present invention can have the following formula:

residue, D-glucuronic acid residue and L-iduronic acid residue. $R_3$, in the above formula, is a member selected from the group consisting of H and $SO_3^-$. Finally, $R_4$ is a member selected from the group consisting of H, $SO_3^-$ and $CH_3CO^-$. In the above structure, sequences having the heparin pentasaccharide sequence for ATIII have been substantially removed by ATIII affinity chromatography. As mentioned, the HCII catalytic agents of the present invention will typically have molecular weights ranging from about 3,000 Daltons to about 8,000 Daltons (±1,000 Daltons).

The HCII-specific catalytic agents, i.e., catalytic agents which selectively catalyze HCII-mediated inactivation of fibrin-bound thrombin, obtained from heparin preparations can be prepared using a number of different methods. As noted above, in a preferred embodiment, the HCII-specific catalytic agents of the present invention are heparin preparations which have been prepared from heparin using the following chemical reactions: (1) depolymerization of unfractionated heparin to yield LMWH; (2) oxidation of the resulting LMWH to open the ring structures the unsulfated uronic acid moieties; and (3) reduction of the oxidized LMWH to reduce the aldehydes (to alcohols) formed during the depolymerization and oxidation steps. In a further preferred embodiment, the HCII-specific catalytic agents of the present invention are prepared from heparin using the following chemical reactions: (1) depolymerization of unfractionated heparin to yield LMWH using nitrous acid; (2) oxidation of the resulting LMWH using sodium periodate; and (3) reduction of the oxidized LMWH using sodium borohydride. In this preferred embodiment, the resulting low

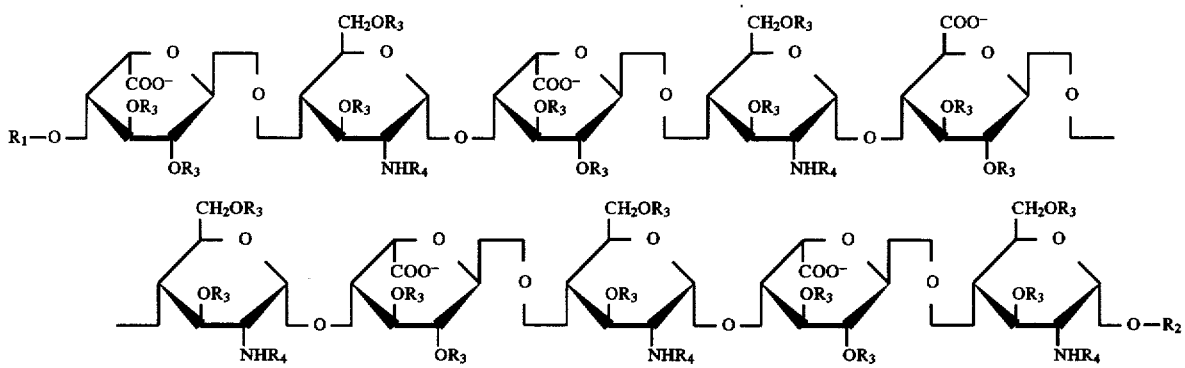

In the above formula, $R_1$ and $R_2$ are members independently selected from the group consisting of H, D-glucosamine acid affinity, low molecular weight heparin is a mixture of heparin molecules having a native sugar (e.g., a uronic acid residue) as the nonreducing terminal and a 2,5-anhydromannitol residue as the reducing terminal, and having molecular weights ranging from about 3,000 to about 8,000 Daltons.

More particularly, heparin with low affinity for ATIII is prepared from standard unfractionated heparin (specific activity 150 to 160 anti-factor Xa and anti-factor IIa units/mg) or low molecular weight heparin either chemically by an oxidation reaction followed by a reduction reaction or, alternatively, by ATIII affinity chromatography. In a preferred embodiment, heparin with low affinity for ATIII is prepared chemically. Such chemical modifications involve treating the vicinal alcohol groups present in the heparin preparation with an oxidizing agent followed by a reducing agent in accordance with the protocol set forth in the Example Section. Suitable oxidizing agents include, but are not limited to, sodium periodate and, under cetain reaction conditions known to those of skill in the art, lead tetraacetate. Suitable reducing agents include, but are not limited to, sodium borohydride, other metal hydrides and, under certain reaction conditions known to those of skill in the art, lithium aluminum hydride. These reactions cleave the vicinal, i.e., C2–C3, bond of a critical non-sulfated glucuronic acid residue found within the heparin pentasaccharide sequence for ATIII. Cleavage of this bond markedly reduces the affinity of heparin for ATIII. Alternatively, ATIII affinity chromatography can be used to select those heparin chains with little or no affinity for ATIII. When prepared by either technique, the resultant low affinity heparin (LAH) has the following characteristics:

a) It is essentially devoid of ATIII-catalyzing, i.e., ATIII-activating, activity (with $\leq 1.5$ anti-factor Xa units/mg), but retains anti-factor IIa activity (of about 2 to about 5 units/mg) because of its ability to catalyze, i.e., activate, HCII.

b) Compared to the starting material, the LAH or LA-LMWH has reduced anticoagulant activity in plasma (as measured by either the activated partial thromboplastin time or the thrombin clotting time), but it retains its ability to catalyze the inactivation of thrombin in buffer containing physiological concentrations of HCII (see, Table 1).

TABLE 1

Figure 6A:
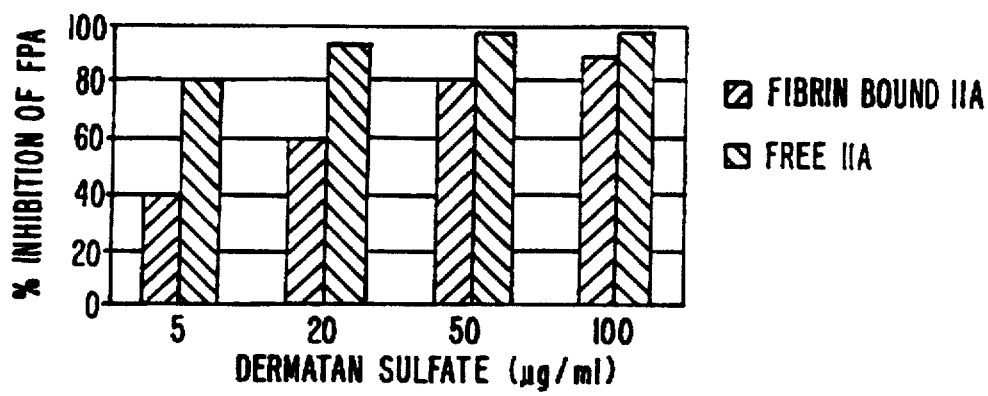
FIGS. 6A and 6B illustrate the ability of dermatan sulfate and a LA-LMWH HCII-specific catalyst of the present invention, i.e., V18, respectively, to inactivate free and fibrin-bound thrombin using the "hanging clot" assay.
Figure 6B:
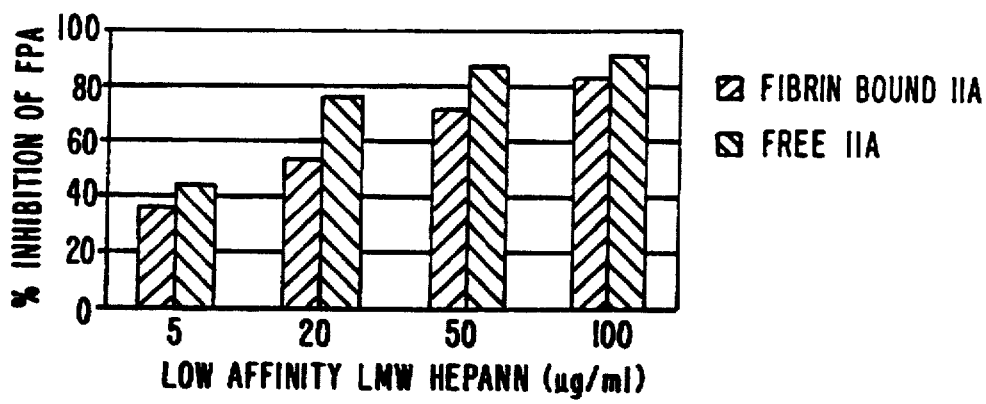

| | TCT (seconds) |
|---|---|
| Baseline | 19.2 |
| V18 120 µg/mL | 26.5 |
| V18 240 µg/mL | 31.5 |
| V18 480 µg/mL | 37.2 |
| V18 960 µg/mL | 43.6 |
| DS 120 µg/mL | 75.9 |
| DS 240 µg/mL | 445 |
| DS 480 µg/mL | 577 |
| DS 960 µg/mL | 841 |
| LAH 120 µg/mL | 556 |
| LAH 240 µg/mL | 717 |
| LAH 480 µg/mL | 1065 |
| LAH 960 µg/mL | 3403 |
| Hirudin 10 U/mL | >500 |
| Hirudin 20 U/ml | >500 | c) In filter-containing plate assays, the LAH is as effective as standard heparin at promoting HCII-mediated displacement (FIG. 4) and inactivation (FIG. 5) of fibrin-bound thrombin. Both standard heparin and LAH inhibit fibrin-bound thrombin to a greater extent than LAH displaces it, consistent with the concept that HCII is able to bind and inactivate thrombin that remains bound to fibrin via exosite 2.

d) Most of the thrombin displaced by either standard heparin or LAH is covalently complexed to HCII as determined by SDS-PAGE analysis (data not shown).

e) Based on the extent of inhibition of clot-induced fibrinopeptide A (FPA) generation in plasma, LAH is as effective as standard, unfractionated heparin at inactivating fibrin-bound thrombin (FIGS. 6A and 6B). In a hanging clot assay, both agents produce only minimal thrombin displacement because the thrombin is bound to fibrin via exosite 2, leaving exosite 1 and the active site free to interact with HCII.

A low molecular weight heparin (LMWH) fraction can be prepared using a variety of techniques, including chemical depolymerization using nitrous acid, enzymatic degradation with heparinase and gel filtration. In a preferred embodiment, LWMH is prepared from standard, unfractionated heparin using nitrous acid depolymerization. The resulting LMWH is typically a mixture of heparin molecules having molecular weights ranging from about 3,000 Daltons to about 8,000 Daltons ($\pm 1,000$ Daltons). This mixture of materials can be used directly or, alternatively, it can be separated into its various components using, for example, gel exclusion chromatography. For instance, the LMWH mixture can be arbitrarily separated into three fractions by gel exclusion chromatography. Fraction 1 has a mean molecular weight of about 8,000 Daltons. Fraction 2 has a mean molecular weight of about 5,000 Daltons and Fraction 3 has a mean molecular weight of about 3,000 Daltons. As illustrated by the examples set forth herein, these three fractions have properties which are distinct from each other as well as from the mixture of materials, i.e., the mixture of heparin molecules having molecular weights ranging from about 3,000 Daltons to about 8,000 Daltons. Thus, depending on whether the mixture of materials, Fraction 1, Fraction 2, Fraction 3 or various combinations of these materials are used, one can take advantage of different properties.

Figure 4:
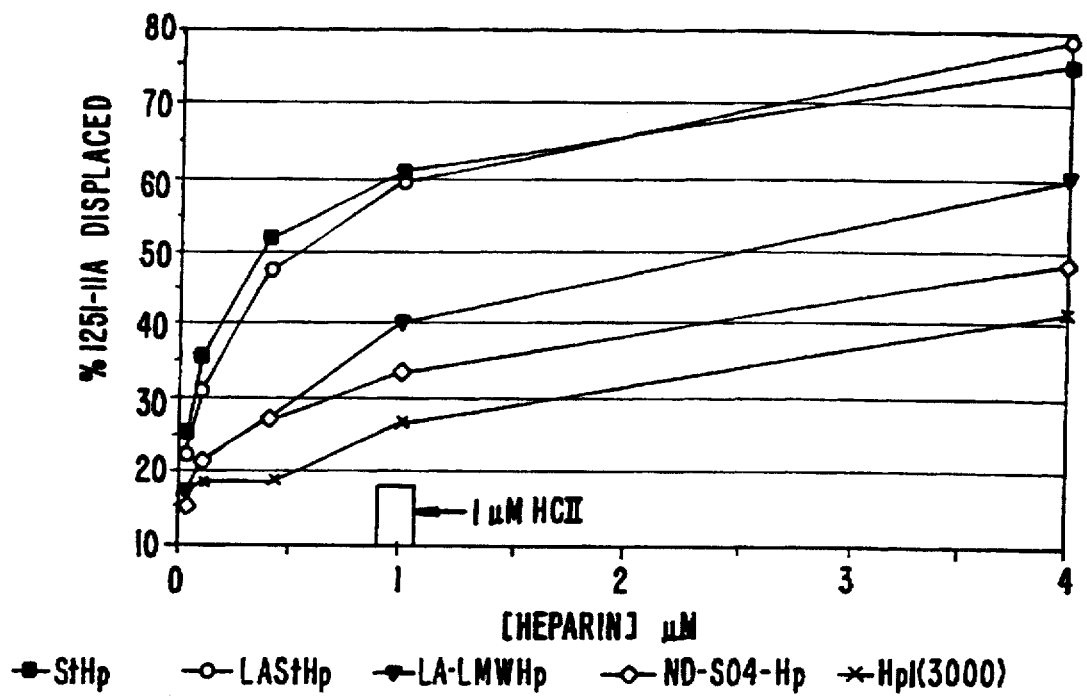
FIGS. 4 and 5 show the mean results of a series of experiments comparing the relative ability of various heparins and a LA-LMWH HCII-specific catalytic agent, i.e., V18, to inhibit and displace thrombin from fibrin using a filter-containing plate assay. There is a dose response for both displacement and inactivation with 85% inactivation and about 60% displacement at 4 μM. Analysis of gels performed on the displaced thrombin and the residual inactivated fibrin-bound thrombin indicates that HCII is covalently bound to the thrombin, indicating that the thrombin is permanently inactivated.
Figure 5:
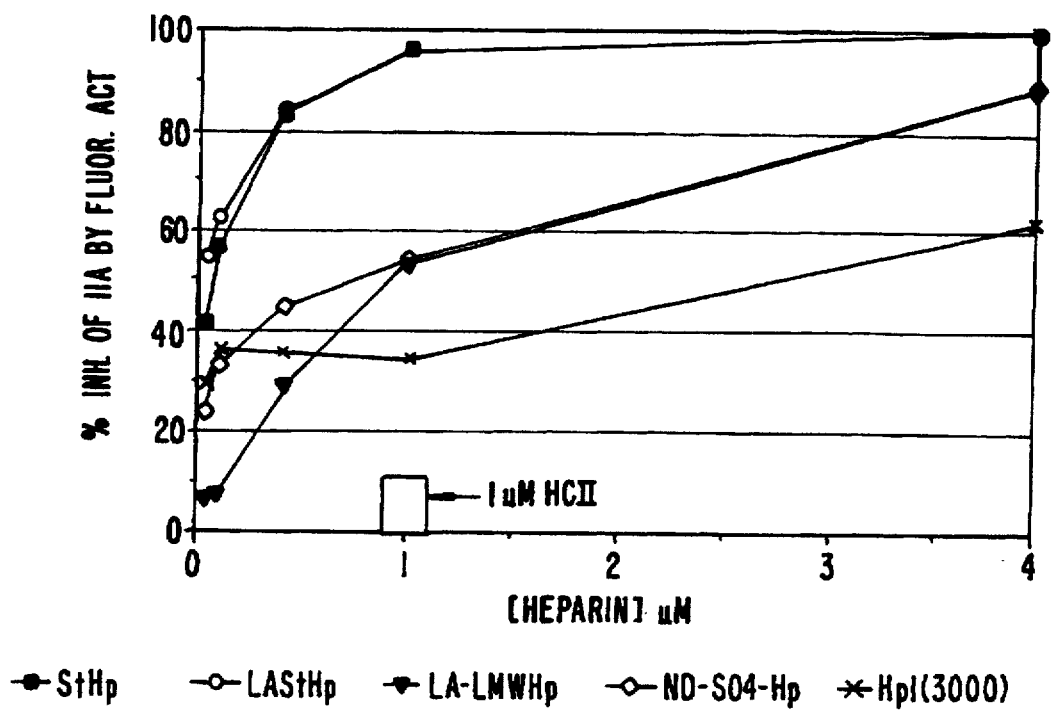

Although LA-LMWH, e.g., V18, is less effective than standard heparin at displacing thrombin from the fibrin-coated filter (FIG. 4), it effectively inhibits the bound thrombin (FIG. 5). For example, 4 µM of V18, a HCII-specific catalytic agent which is a mixture of LA-LMWH molecules having molecular weights ranging from about 3,000 to about 8,000 Daltons, only displaces 60% of the bound thrombin, but produces greater than 85% inhibition of the activity of the bound enzyme. However, V18 causes less inhibition of fluid-phase thrombin because 4 µM of V18 produces a thrombin clotting time of only 50s, whereas 4 µM of standard heparin produces an unmeasurable thrombin clotting time.

The LA-LMWH of the present invention has the following characteristics:

a) Its specific activity is about 0.2 to about 1.5 anti-factor Xa units/mg and about 2 to about 5 anti-factor IIa units/mg.

b) Compared to both standard unfractionated heparin and LAH, LA-LMWH has reduced anticoagulant activity in plasma (as measured by the thrombin clotting time) and produces less catalysis, i.e., activation, of HCII-mediated thrombin inactivation in buffer containing physiological concentrations of HCII (see, Table 1, supra).

c) In filter-containing plate assays, LA-LMWH is less effective than standard heparin or LAH at promoting HCII-mediated displacement of fibrin-bound thrombin, but it is able to promote the inactivation of the bound thrombin to a similar extent (FIGS. 5 and 6).

d) Based on its ability to inhibit clot-induced fibrinopeptide A (FPA) generation in plasma (FIGS. 6A and 6B), LA-LMWH is substantially as effective as standard, unfractionated heparin and LAH at inactivating fibrin-bound thrombin. In contrast, the LA-LMWH is less than about one-tenth as effective as heparin and LAH at inactivating free thrombin in a thrombin clotting time assay. Thus, compared to standard, unfractionated heparin and LAH, the LA-LMWH selectively promotes the inactivation of fibrin-bound thrombin.

e) The LA-LMHH of the present invention has an anticoagulant effect which is contributed to by both an HCII- and ATIII-mediated mechanism, and by a mechanism which is independent of both HCII and ATIII.

Thus, the products and HCII-specific catalytic agents of the present invention preferably have one or more of the following characteristics. In one embodiment, the present invention preferably provides heparin preparations that have been chemically modified in two ways. First, they are chemically depolymerized using, e.g., nitrous acid and, thus, reduced in size to about one-third of the size of the heparin parent molecule and, thus, they typically have molecular weights ranging from about 3,000 to about 8,000 Daltons (±1,000 Daltons). This modification results in a marked loss of their ability to catalyze the activity of heparin co-factor II (HCII) against free thrombin, while retaining their ability to catalyze the activity of HCII against surface-bound thrombin. Second, they are subjected to oxidation and reduction reactions which result in a loss of about 95 to about 99% of their antithrombin III-binding activity. More particularly, they have weak ATIII catalytic activity or, interchangeably, ATIII activating activity as evidenced by an anti-factor Xa level of approximately 0.2 to about 1.5 units per ml, which represents about a 95 to about 99% reduction in activity compared to the unmodified low molecular weight heparin. Thus, the resulting HCII-specific catalytic agents of the present invention have weak activity against free thrombin, as evidenced by their inability to prolong the thrombin clotting time more than five-fold at concentrations which effectively inactivate surface-bound thrombin. These two properties, namely, a relatively greater ability than other HCII catalysts or, interchangeably, HCII activators (such as dermatan sulfate) to inactivate surface-bound than free thrombin and some, albeit markedly reduced, ATIII-dependent anti-factor Xa activity, are responsible for their improved anti-thrombic effects compared to heparin, dermatan sulfate and hirudin in a bypass circuit, which is a measure of surface-bound thrombin, at concentrations which have a lesser effect than these other anticoagulants on the inactivation of free thrombin as measured by the prolongation of the thrombin clotting time. Moreover, and quite surprisingly, such agents have an anticoagulant effect which is contributed to by both an HCII- and ATIII-mediated mechanism, and by a mechanism which is independent of both HCII and ATIII.

As a result of the foregoing properties, the products and HCII-specific catalytic agents of the present invention, i.e., catalysts which are capable of displacing and/or inactivating clot-bound thrombin, can be used for preventing thrombus formation and/or for blocking thrombus growth in a patient without producing excessive bleeding, i.e., without producing a clinically unsafe increase in systemic bleeding. More particularly, the HCII-specific catalytic agents of the present invention can be administered in' doses which inactivate surface-bound thrombin, but which have only small effects at inhibiting free thrombin. As such, in another embodiment, the present invention provides a method for inhibiting thrombus formation in a patient, preferably without inducing a clinically unsafe increase in systemic bleeding, the method comprising the step of administering to the patient a pharmacologically acceptable dose of a heparin cofactor II-specific catalytic agent capable of inactivating clot-bound thrombin, the HCII-specific catalytic agent characterized by: (i) a heparin cofactor II specific activity against heparin cofactor II of about 2 to about 5 units/mg in an anti-factor IIa assay; (ii) an antithrombin III (ATIII) specific activity against factor Xa of about 0.2 to about 1.5 units/mg in an anti-factor Xa assay; and (iii) a solubility in aqueous media ranging from about 150 to about 1,000 mg/ml.

The HCII-specific catalytic agents (and other thrombin-inactivators) of the present invention are effective when used alone or, alternatively, when used with low doses of heparin or low molecular weight heparin which are required to inactivate free thrombin. In heparin-resistant conditions (i.e., disorders requiring very high doses of heparin), for example, the HCII-specific catalytic agents of the present invention can be used as a heparin-sparing agent. As such, in another embodiment, the present invention provides combinations and, preferably, blends of an HCII-specific catalytic agent and an ATIII catalytic agent, i.e., and ATIII activating agent. Such blends are useful for inhibiting thrombogenesis in a patient without substantially inhibiting normal coagulation. Thus, the compositions or blends of the present invention are useful for inhibiting thrombus formation in a patient without inducing a clinically unsafe increase in systemic bleeding. In addition, such compositions or blends are useful for prophylaxis, for the treatment of venous or arterial thrombosis and for the prevention of clotting in extracorporeal circuits.

The blends of the present invention will typically be from about 90 to about 99.9 percent by weight of an HCII-specific catalytic agent and, more preferably, from about 95 to about 98.5 percent by weight; and from about 0.1 to about 10 percent by weight of an ATIII catalytic agent, i.e., an ATIII activating, and, more preferably, from about 0.5 to about 5 percent by weight. Typically, the overall HCII catalyst activity of the blends will be about 2 to about 5 units/mg and, more preferably, about 2 to about 4 units/mg. ATIII catalytic or activating agents suitable for use in the blends of the present invention include, but are not limited to, heparin and LMWH. In addition, other agents can be added as desired to modify the blend, including, for example, LMWH (0.1 to 5 wt %), heparin (0.1 to 5 wt %), direct thrombin inhibitors, direct inhibitors of activated factor X, etc.

In another embodiment, the present invention provides a method for inhibiting clot-bound thrombin and fluid-phase thrombin in a patient, preferably without inducing a clinically unsafe increase in systemic bleeding, the method comprising the step of administering to the patient a pharmacologically acceptable dose of (i) an HCII-specific catalytic agent capable of inactivating clot-bound thrombin, the HCII-specific catalytic agent having minimal affinity for antithrombin III (ATIII) and a heparin cofactor II specific activity of about 2 to about 5 units/mg in an anti-factor IIa assay; and (ii) an ATIII catalytic agent capable of inactivating fluid-phase thrombin. Suitable ATIII catalytic agents, i.e., ATIII activating agents, include, but are not limited to, heparin, low molecular weight heparin, direct thrombin inhibitors and direct inhibitors of activated factor X. Moreover, in this method, the HCII-specific catalytic agent and the ATIII catalytic agent, i.e., the ATIII activating agent, can be administered to the patient simultaneously, separately or sequentially. When administered to the patient simultaneously, the HCII-specific catalytic agent and the ATIII catalytic agent can be administered together as a single solution or compound or, alternatively, they can be administered separately as two different solutions or compounds.

The HCII-specific catalytic agents and blends of the present invention can be incorporated as components in pharmaceutical compositions which are useful for treating the cardiovascular conditions described above. Such compositions will also be useful in conjunction with conventional thrombolytic treatments, such as the administration of tissue plasminogen activator (tPA), streptokinase, and the like, as well as with intravascular intervention, such as angioplasty, atherectomy, and the like.

Suitable pharmaceutical compositions will contain a therapeutically effective dose of one or more active products of the invention, e.g.,a HCII-specific catalytic agent of the present invention, in a pharmaceutically acceptable carrier. Other suitable pharmaceutical compositions will contain a therapeutically effective dose of a blend of an active product of the present invention (e.g., a HCII-specific catalytic agent) and an ATIII-specific catalytic agent. By a "therapeutically effective dose" or, interchangeably, "pharmacologically acceptable dose," it is meant that a sufficient amount of the product or HCII-specific catalytic agent or, alternatively, a combination or blend of, for example, a HCII-specific catalytic agent and an ATIII-specific catalytic agent will be present in order to inactivate clot-bound thrombin and/or to inhibit thrombus accretion when treating a thrombus-related cardiovascular condition, such as those described above.

Typically, the active product or HCII-specific catalytic agent will be present in the pharmaceutical composition at a concentration ranging from about 200 mg per dose to 2 g per dose and, more preferably, at a concentration ranging from about 500 mg per dose to 1 g per dose. Daily dosages can vary widely, depending on the activity of the particular HCII-specific catalytic agent employed, but will usually be present at a concentration ranging from about 30 µg per kg of body weight per day to about 500 µg per kg of body weight per day and, more preferably, at a concentration ranging from about 50 µg per kg of body weight per day to about 200 µg per kg of body weight per day.

With respect to the combined or blended pharmaceutical compositions, the active product or HCII-specific catalytic agent will be present at a concentration ranging from about 3 mg/kg per dose to about 30 mg/kg per dose and, more preferably, at a concentration ranging from about 3 mg/kg per dose to 10 mg/kg per dose, and the ATIII catalytic agent, i.e., the ATIII activating agent, will be present at a concentration ranging from about 10 U/kg per dose to 500 U/kg per dose and, more preferably, at a concentration ranging from about 15 U/kg per dose to 100 U/kg per dose. Daily dosages can vary widely, depending on the activity of the particular HCII-specific and ATIII catalytic or, alternatively, activating agents employed. Typically, the HCII-specific catalytic agent will usually be present at a concentration ranging from about 3 mg per kg of body weight per day to about 30 mg per kg of body weight per day and, more preferably, at a concentration ranging from about 3 mg per kg of body weight per day to about 10 mg per kg of body weight per day, whereas the ATIII catalytic agent will usually be present at a concentration ranging from about 10 U per kg of body weight per day to about 500 U per kg of body weight per day and, more preferably, at a concentration ranging from about 15 U per kg of body weight per day to about 100 U per kg of body weight per day.

The pharmaceutically acceptable carrier can be any compatible, non-toxic substance suitable to deliver the HCII catalytic agent or the blend of a HCII-specific catalytic agent and an ATIII-specific catalytic agent to the patient. Sterile water, alcohol, fats, waxes, and inert solids can be used as the carrier. Pharmaceutically acceptable adjuvants, buffering agents, dispersing agents, and the like can also be incorporated into the pharmaceutical compositions. Such compositions will be suitable for oral, nasal, respiratory or parenteral administration, preferably being suitable for parenteral administration, i.e., subcutaneous, vascular and intravenous administration. It may also be preferred to deliver the substances provided by the present invention via transdermal administration.

In view of the foregoing, it is readily apparent to those of skill in the art that the HCII-specific catalytic agents or active products of the present invention can effectively be used to selectively inhibit clot- or fibrin-bound thrombin without inducing a clinically unsafe increase in systemic bleeding. In addition, the HCII-specific catalytic agents of the present invention can effectively be used in combination with other ATIII catalytic, i.e., activating, agents (e.g., heparin or LMWH) to inhibit both clot-bound thrombin and fluid-phase thrombin without inducing a clinically unsafe increase in systemic bleeding. As such, the HCII-specific catalytic agents of the present invention can be used alone, or in combination with other ATIII catalytic, i.e., activating, agents to treat a number of important cardiovascular complications, including unstable angina, acute myocardial infarction (heart attack), cerebral vascular accidents (stroke), pulmonary embolism, deep vein thrombosis, arterial thrombosis, etc.

In addition to being useful in pharmaceutical compositions for the treatment of the cardiovascular conditions described above, one of skill in the art will readily appreciate that the active products or HCII-specific catalytic agents and combinations of the present invention can be used as reagents for elucidating the mechanism of blood coagulation in vitro.

Having produced heparin fractions or derivatives thereof having the desired properties described above, other thrombin inactivators or HCII-specific catalytic agents having similar catalytic specificity and/or affinity can be produced by a variety of methods well-known to those of skill in the art. For example, Fodor, et al., U.S. Pat. No. 5,143,854 describe a technique termed "VLSIPS," in which a diverse collection of short peptides are formed at selected positions on a solid substrate. Such peptides are then screened for the ability to conformationally alter HCII, such screening optionally in competition with the heparin fractions. Libraries of short peptides can also be produced and screened using phage-display technology (see, e.g., Devlin, WO 91/18980). Optionally, these polypeptides or variants produced by other methods, can be variegated to achieve improved binding affinity for HCII (see, e.g., Ladner, U.S. Pat. No. 5,223,409, which is incorporated by reference in its entirety for all purposes).

Peptidic analogs of the HCII activators can be prepared by conventional solid phase synthesis or recombinant techniques, both of which are well described in the art. Suitable solid phase synthesis techniques are based on the sequential addition of amino acids to a growing chain on a solid-phase substrate, as first described in Merriefield, *J. Am. Chem. Soc.* 85:2149–2156 (1963). Commercial systems for automated solid-phase synthesis are now widely available from suppliers, such as Applied Biosystems, Inc., Foster City, Calif. Moreover, recombinant polypeptide production techniques are widely described in the technical and scientific literature. See, for example, *Molecular Cloning: A Laboratory Manual*, Sambrook, et al., Eds., Cold Spring Harbor Laboratory Press, Cold Spring Harbor, New York (1989), Vols. 1–3.

Small molecule mimetics of the HCII-specific catalytic agents of the present invention can be achieved through the use of techniques known to those working in the area of drug design. Such methods include, but are not limited to, self-consistent field (SEF) analysis, configuration interaction (CI) analysis, and normal mode dynamics computer programs, all of which are now readily available. See, Rein, et al., *Computer-Assisted Modeling of Receptor-Ligand Interactions*, Alan Liss, New York (1989) and Navia and Marcko, "Use of Structural Information in Drug Design," in *Current Opinion in Structural Biology*, Vol. 2, No. 2, pages 202–210, 1992. The preparation of compounds identified by these techniques will depend on their structure and other characteristics and may normally be achieved by standard chemical synthesis methods as described in available texts, such as Furniss, et al., *Vogel's Textbook of Practical Organic Chemistry*, John Wiley & Sons, New York 1992 and Larock, *Comprehensive Organic Transformations*, VCH Publishers, Inc., New York 1989.

The invention will be described in greater detail by way of specific examples. The following examples are offered for illustrative purposes, and are intended neither to limit or define the invention in any manner. In the Examples, the thrombin inactivators are illustrated by heparin-derived HCII-specific catalytic agents, but the invention is not limited to such agents.

EXAMPLES

A. Preparation of Material

Heparin is a glycosaminoglycan (GAG) isolated from natural sources (usually pig gut mucosa). One aspect of the present invention is to prepare a low molecular weight heparin fraction that is essentially devoid of antithrombin III activating activity, yet retains the ability to catalyze heparin cofactor II. As a consequence of its ability to catalyze heparin cofactor II, this modified GAG can inactivate thrombin bound to fibrin.

Generally, low molecular weight heparin is prepared from standard unfractionated heparin by benzylation followed by alkaline depolymerization; nitrous acid depolymerization; enzymatic depolymerization with heparinase; or peroxidative depolymerization. In a presently preferred embodiment, low molecular weight heparin is prepared from standard heparin using nitrous acid depolymerization. The low molecular weight heparin is then further modified to reduce its affinity for antithrombin III. This can be accomplished chemically or, alternatively, through the use of an antithrombin III affinity column. In a presently preferred embodiment, this is accomplished chemically by an oxidation reaction followed by a reduction reaction. The resulting low affinity, low molecular weight heparin is typically a mixture of heparin molecules having molecular weights ranging from about 3,000 to about 8,000 Daltons. This range corresponds to about 10 to about 24 monosaccharide units. The specific activity of this material is about 2 to about 5 antithrombin units/mg and less than about 1.5 (starting, 100 anti-Xa) anti-Xa units/mg.

Figure 7:
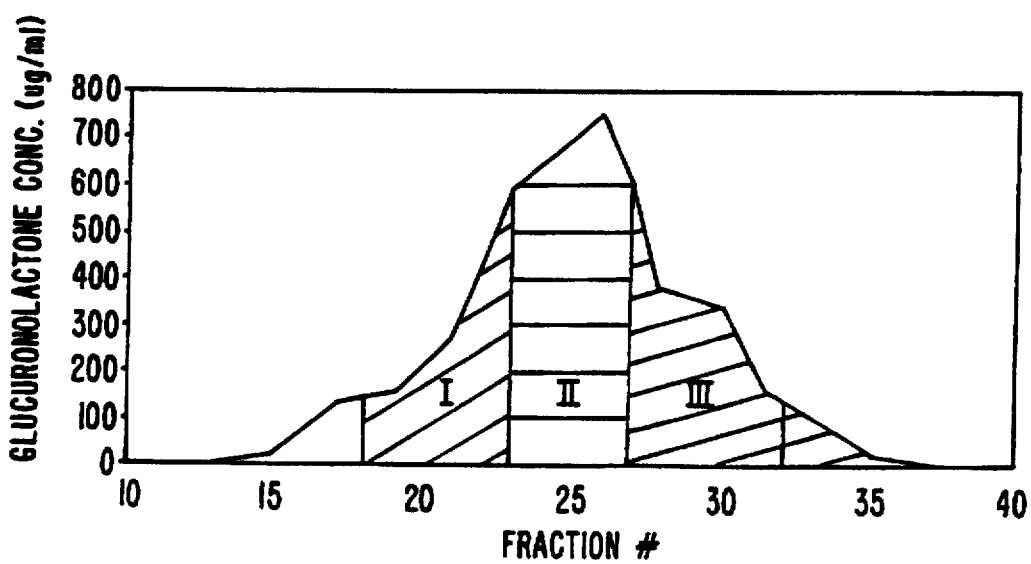
FIG. 7 illustrates the elution profile of V18 on a G-50 Sephadex column.

The LA-LMWH mixture of materials can be used directly or, alternatively, it can be separated into its various components using, for example, gel exclusion chromatography. The LA-LMWH fraction generally yields three LA-LWMH fractions when separated by gel exclusion chromatography. Fraction 1 has a mean molecular weight of about 8,000 Daltons, Fraction 2 has a mean molecular weight of about 5,000 Daltons and Fraction 3 has a mean molecular weight of about 3,000 Daltons. FIG. 7 illustrates the elution profile of the LA-LMWH mixture of materials using a G-50 SEPHADEX column and various concentrations of glucuronolactone. As with the LA-LMWH mixture of materials, the specific activity of each of these three LA-LMWH fractions is about 2 to about 5 antithrombin units/mg and less than about 1.5 (starting, 100 anti-Xa) anti-Xa units/mg.

The following examples illustrate experimental protocols which can be used to prepare the HCII-specific catalytic agents of the present invention. As noted above, in a presently preferred embodiment, the chemical reactions leading to the preparation of the HCII-specific catalytic agents of the present invention are: (1) nitrous acid depolymerization of heparin to yield low molecular weight heparin; (2) periodate oxidation of low molecular weight heparin to open the ring structures of unsulfated uronic acid moieties; and (3) borohydride reduction of aldehydes (to alcohols) formed during the nitrous acid and periodate steps.

1. Example 1: Preparation of V-18, Lot #7-1 a. Step 1: Isolation of LMW-heparin, Lot #7

Porcine intestinal heparin (250 grams) was dissolved in 5 liters of purified water (5% solution). Sodium nitrite (3.45 grams) was added and dissolved into the solution to give a 10 mM concentration. The solution temperature was between 18 and 24 degrees Celsius. Over the course of about 2 minutes, 30 mls of 37% HCl were added and the pH adjusted from an initial value of 6.32 to a final pH of 3.00. The resultant solution was then stirred for 2 hours at ambient temperature to allow depolymerization to occur. At the end of the 2 hour incubation, the pH was adjusted upwards to a value of 6.75 by slow addition of about 18 mls of 50% NaOH solution.

The sample was then diluted to a volume of 12.5 liters and ultrafiltered against 10 volumes of purified water using a Millipore Pellicon ultrafiltration device equipped with 10,000 molecular weight cut-off membranes (1.5 m$^2$). The permeate from the ultrafiltration was then concentrated and dialyzed using a Millipore Pellicon ultrafiltration unit equipped with 3,000 molecular weight cut-off membranes (1.5 m$^2$). Once the 125 liters of permeate was concentrated to about 6 liters, it was then dialyzed against 3-volumes of purified water. The retentate was then freeze-dried to give LMW-heparin, Lot#7. Yield=106 grams (42%)

Molecular weight characteristics of LMW-heparin intermediate #7 (above) were determined by high performance size exclusion chromatography in conjunction with multi-angle laser light scattering (HPSEC-MALLS) and are compiled in Table 2.

TABLE 2

| HPSEC-MALLS Results for LMW-Heparin Intermediate & V18 Product | | | | | | | |
|---|---|---|---|---|---|---|---|
| Lot: | #7 | #7-1 | #9 | #9-1 | #9-2 | #20 | #20-1 |
| >2,000 | 100 | 100 | 99.8 | 100 | 100 | 99.2 | 100 |
| >3,000 | 100 | 100 | 80.4 | 100 | 100 | 76.4 | 77.1 |
| >4,000 | 57.5 | 61.8 | 50.1 | 63.6 | 63.9 | 52.1 | 51.8 |
| >5,000 | 35.0 | 39.9 | 29.9 | 36.2 | 36.4 | 35.5 | 34.2 |
| >6,000 | 22.2 | 25.0 | 18.2 | 20.6 | 20.6 | 24.4 | 22.9 |
| >7,000 | 14.0 | 16.3 | 10.8 | 12 | 11.8 | 16.5 | 15.8 |
| >8,000 | 9.2 | 10.5 | 6.4 | 6.5 | 6.5 | 11.6 | 10.9 |
| >9,000 | 5.8 | 7.1 | 3.6 | 3.6 | 3.6 | 7.7 | 7.6 |
| Mw[ii] | 4,989 | 5,228 | 4,583 | 5,022 | 5,024 | 4,920 | 4,876 |
| Mn[iii] | 4,421 | 4,602 | 4,031 | 4,582 | 4,603 | 4,067 | 4,006 |
| Mw/Mn[iv] | 1.129 | 1.136 | 1.137 | 1.096 | 1.091 | 1.210 | 1.217 |

[i]Weight fraction above a given molecular weight, expressed in percent.
[ii]Weight-average molecular weight.
[iii]Number-average molecular weight.
[iv]Polydispersity.

b. Steps 2 and 3: Oxidation and Reduction of LMW-heparin, Lot #7

LMW-heparin, Lot #7 (100 grams) was dissolved in 1 liter of purified water at 4–10 degrees Celsius. One liter (1 liter) of 200 mM sodium acetate, pH 5.0 was added to the dissolved sample. Two liters (2 liters) of 200 mM sodium periodate was added to the buffered LMW-heparin solution. The resultant solution was incubated in the dark at 4–10 degrees C. for 48 hours with gentle stirring.

After 48 hours, excess sodium periodate was destroyed by addition of glycerol (70 mls). The pH of the resultant reaction mixture was raised to neutrality with ~10 mls of 50% NaOH solution and the resultant solution diluted to about 5.5 liters. This solution was then dialyzed (ultrafiltered) using the Millipore Pellicon system equipped with 3,000 MWCO membranes (as in Step 1 above). After ~7 volumes of permeate were collected, the oxidized LMW-heparin intermediate solution was concentrated to a volume of ~3 liters.

Reduction of the oxidized intermediate was carried out as follow: Sodium bicarbonate (63 grams) was added and mixed into the above 3 liter solution to give ~0.25M $NaHCO_3$ solution. This solution was kept cold (4°–10° C.) while a solution (1.2 liters) containing 22.8 grams of $NaBH_4$ (also 4°–10° C.) was slowly added with stirring. Once all the $NaBH_4$ solution was added, the reaction was kept at 4°–10° C. for 3.5 hours. The reaction pH was then adjusted to 4.0 with 6M HCl (~230 mls), mixed for ~30 minutes, then adjusted upwards in pH to 6.2 with 50% NaOH addition. This sample was then ultrafiltered again against the 3,000 MWCO membranes using the Millipore Pellicon system (7 volumes) and finally sterile filtered through a 0.2µ Sterivex (Millipore) filter. The resultant solution was freeze-dried to give V-18, Lot#71. Yield=76.6 grams.

Molecular weight characteristics of the product were determined by HPSEC-MALLS and are compiled in Table 2, supra.

2. Example 2: Preparation of V-18, Lots #9-1 and 9-2 a. Step 1: Isolation of LMW-Heparin, Lot#9

Porcine intestinal heparin (250 grams) was dissolved in 5 liters of purified water (5% solution). Sodium nitrite (8.62 grams) was added and dissolved into the solution to give a 25 mM concentration. The solution temperature was between 18 and 24 degrees Celsius. Over the course of about 2 minutes, 33 mls of 37% HCl were added and the pH adjusted from an initial value of 6.32 to a final pH of 3.01. The resultant solution was then stirred for 2 hours at ambient temperature to allow depolymerization to occur. At the end of the 2 hour incubation, the pH was adjusted upwards to a value of 6.28 by slow addition of 50% NaOH solution.

The sample was then diluted to a volume of 10 liters and ultrafiltered against 7 volumes of purified water using a Millipore Pellicon ultrafiltration device equipped with 3,000 MWCO membranes (1.5 m²). The sample was then concentrated to ~3.5 liters and freeze-dried to give LMW-heparin Lot#9. Yield=120.4 grams (48%)

Molecular weight characteristics of LMW-heparin intermediate #9 were determined by HPSEC-MALLS and are compiled in Table 2, supra.

b. Steps 2 and 3: Oxidation and Reduction of V-18, Lots 9-1 and 9-2

Two identical but separate fifty gram (50 gm) samples of LMW-heparin, Lot #9, were treated as follows: LMW-heparin (50 gm) was dissolved in 500 ml of purified water (4°–10° C.). Sodium acetate buffer (500 mls of 200 mM, pH 5.0) was added to each identical sample. Sodium periodate (1,000 mls of 200 mM solution) was then added to each reaction and the resultant solutions were each incubated in the dark and cold for 72 hours. After the 72 hr. incubation, glycerol (40 mls) was added to each sample to destroy excess periodate. The reaction pH was then raised to ~6.5 for each sample and each ultrafiltered against 7 volumes of purified water using the Pellicon system equipped with 3,000 MWCO membranes.

Reduction of each of the resultant oxidized LMW-intermediates and all other steps in the workup were exactly as indicated for sample 7-1 in Example 1 (above). Yields of V-18, Lots #9-1 and 9-2 were: 37.4 gms and 36.7 gms, respectively.

Molecular weight characteristics of V-18, Lots #9-1 and 9-2 were determined by HPSEC-MALLS and are compiled in Table 2, supra.

3. Example 3: Preparation of V-18, Lot #20-1 a. Step 1: Isolation of LMW-Heparin, Lot #20

Porcine intestinal heparin (500 grams) was dissolved in 10 liters of purified water (5% solution). Sodium nitrate (9.0 grams) was added and dissolved into the solution to give a 12.8 mM concentration. The solution temperature between 18 and 24 degrees Celsius. Over the course of about 2 minutes, 59 mls of 37% HCl were added and the pH adjusted from an initial value of 6.27 to a final pH of 3.00. The resultant solution was then stirred for 2 hours at ambient temperature to allow depolymerization to occur. At the end of the 2 hour incubation, the pH was adjusted upwards to a value of 6.57 by slow addition of about 38 mls of 50% NaOH solution.

The sample was then diluted to a volume of 17 liters and ultrafiltered against 10 volumes of purified water using a Millipore Pellicon 11 ultrafiltration device equipped with 8,000 molecular weight cut-off membranes (1.5 m²). The permeate from the ultrafiltration was then concentrated and dialyzed using a Millipore Pellicon II ultrafiltration unit equipped with 3,000 molecular weight cut-off membranes (1.5 m²). Once the 170 liters of permeate was concentrated to about 8.5 liters, it was then dialyzed against 7-volumes of purified water. The retentate was then freeze-dried to give LMW-heparin, Lot #20. Yield=171.3 grams (34%).

Molecular weight characteristics of LMW-heparin intermediate #20 (above) were HPSEC-MALLS) and are compiled in Table 2, supra.

b. Steps 2 and 3: Oxidation and Reduction of V-18, Lot 20-1

LMW-heparin (170 gms. of Lot #20) was dissolved in 1700 mls of purified water (4°–10° C.). Sodium acetate buffer (1700 mls of 200 mH, pH 5.0) was added and mixed with the sample. Sodium periodate (3,400 mls of 200 mM solution) was then added to the mixture to initiate reaction and the resultant solution was incubated in the dark and cold for 72 hours. After the 72 hr. incubation, glycerol (115 mls) was added to destroy excess periodate. The reaction pH was then raised to –6.5 and the oxidized LMW-heparin ultrafiltered vs 7 volumes of purified water using the Pellicon II system equipped with 3,000 MWCO membranes.

Reduction of the resultant oxidized LMW-intermediate and all other steps in the workup were exactly as indicated for sample 7-1 in Example (above). Yield of V-18 lots #20-1 was 131 gms.

Molecular weight characteristic of V-18 lot #20-1 was determined by HPSEC-MALLS and is included in Table 2, supra.

B. Filtration-Based Assay

In addition to examining the ability of various heparin derivatives to catalyze HCII-mediated inactivation of fluid-phase thrombin, their ability to displace and inactivate thrombin bound to fibrin was also studied. In this system, a fibrin clot was formed on a filter-covered well of a 96 well plate by adding 25 µl of buffer containing 8 µM fibrinogen, 8 mM CaCl$_2$ and 8 nM $^{125}$I-labeled thrombin to each well. After incubation for 30 minutes at room temperature, the resultant clot was washed twice with 150 µl of buffer and the bound thrombin was quantified by counting the radioactivity. Varying concentrations of the different materials derived from heparin were added with and without HCII. In each case, these components were added in a 20 µl volume, incubated for 20 min and then aspirated through the filter plate. This step was repeated and the clot was then washed twice with 50 µl of buffer. The amount of thrombin displaced from the clot was determined by counting the wash buffer, whereas the amount of thrombin that remained bound to the fibrin was quantified by counting the filter. The enzymatic activity of the residual bound thrombin was determined by adding a synthetic thrombin substrate and monitoring changes in the fluorescent signal due to the reaction over a 3 minute interval. Finally, the wash buffers were collected and the filters were punched out and, after boiling in SDS-containing buffer, were subjected to SDS-PAGE followed by autoradiography to determine the extent to which thrombin was complexed to HCII.

As illustrated in FIG. 4, 1 µM HCII (which is the physiologic HCII concentration) displaces only small amounts of thrombin. SH, LASH, LMWH and a heparin fraction with a molecular weight of 3,000 Daltons do not displace thrombin without HCII. However, when used in conjunction with 1 µM HCII, these substances all displace thrombin (FIG. 4), with SH and LASH producing more displacement than LMWH (which has a mean molecular weight of about 5,500 Daltons). However, all of the agents inhibit the thrombin that remains bound to the fibrin (FIG. 5), with the SH and LASH producing almost complete inhibition at high concentrations and the LA-LMWH, i.e., V18, producing somewhat less inhibition. Gel electrophoresis analysis of the material that remains bound to the filter indicates that most of the thrombin is complexed to HCII, thereby explaining its lack of chromogenic activity. These findings suggest that the thrombin that remains bound to the fibrin is bound via exosite 2, thereby leaving exosite 1 and the active site available to interact with HCII.

C. Hanging Clot Assay

The Hanging Clot Assay is used to examine the inhibitory effect of agents against fluid-phase and clot-bound thrombin activity. To determine the inhibitory effect against fluid-phase thrombin activity, α-thrombin (0.2–4.0 nM) was incubated with citrated plasma for 60 min at 37° C. in the presence or absence of heparin at the concentrations indicated. At the end of the incubation period, the plasma levels of Fibrinopeptide A (FPA) were determined, and the percent inhibition of FPA generation was then calculated for each inhibitor concentration. To determine the inhibitory effect against clot-bound thrombin activity, washed fibrin clots were incubated in citrated plasma for 60 min at 37° C. in the presence or absence of varying concentrations of heparin. At the end of the incubation period, the plasma levels of FPA were determined, and the percent inhibition of clot-induced FPA generation was then calculated for each inhibitor concentration. Each bar represents the mean of three separate experiments (each done in duplicate), while the lines above the bars represent the SD.

FIGS. 6A and 6B illustrate studies comparing the relative ability of dermatan sulfate (the prototype HCII activator) and one of the LA-LMWH HCII-specific catalysts of the present invention, i.e., V18, to inactivate free and fibrin-bound thrombin using the hanging clot assay. At 5 µg/ml, LA-LMWH was much more selective than dermatan sulfate (dermatan sulfate was only half as effective at inactivating fibrin-bound thrombin, while LMWH was almost as effective at inactivating fibrin bound and free thrombin). At 20 µg/ml, the advantage of LA-LMWH was still apparent even though it was somewhat less obvious. At higher concentration, both are almost 90% as effective at inactivating fibrin-bound and free thrombin.

Other results from the Hanging Clot Assay also indicate that the LA-LMW HCII activators of the present invention bind to and inactivate clot- or thrombus-bound thrombin. In these experiments, a 250 µl clot containing labelled thrombin was suspended in 10 ml of solution containing either 150 mM NaCl or 2M NaCl. One of the following was added to the isotonic buffer: HCII 0.25 or 0.5 µM 100 µg of the LA-LMWH HCII-specific catalytic agent, or the combination of HCII and the LA-LMWH HCII-specific catalytic agent. The following measurements were made: (1) diffusion of thrombin out of the clot; (2) the catalytic activity of thrombin on the clot, which was assessed by measuring fibrinopeptide A production after removing the clot and adding it to a fibrinogen solution; and (3) the extent of thrombin/HCII complex formation, which was assessed by solubilizing the clot and performing SDS-PAGE and autoradiography.

Figure 8:
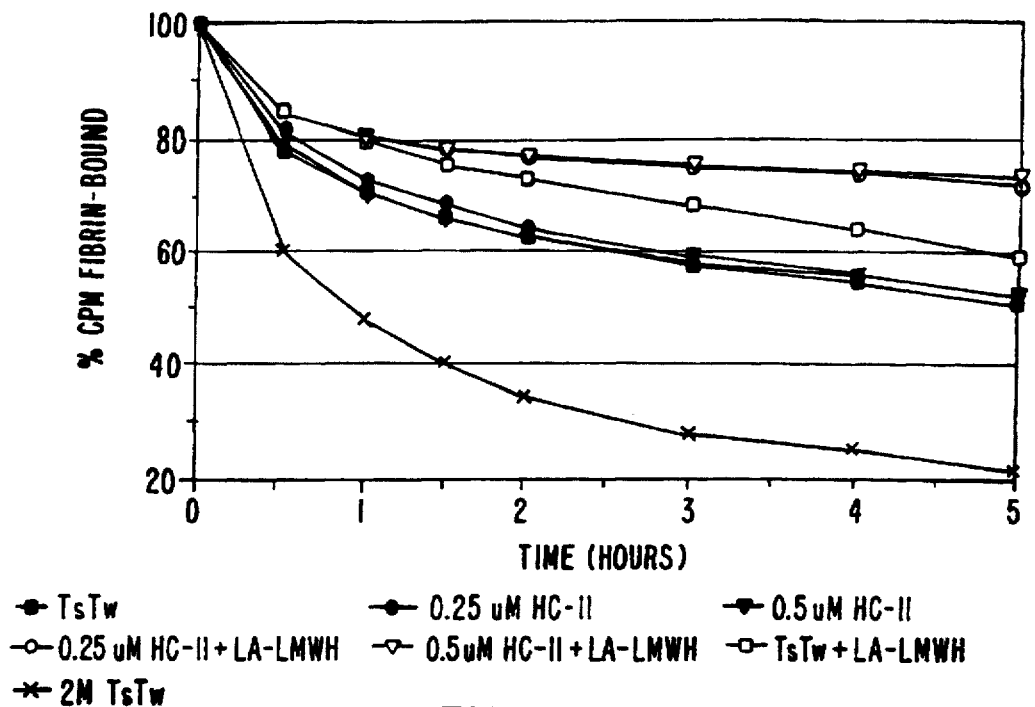
FIG. 8 illustrates the rate of diffusion of labelled thrombin from the fibrin clot.

FIG. 8 illustrates the rate of diffusion of labelled thrombin from the fibrin clot. After 5 hours, about 40% of the thrombin remained in the clot suspended in 150 mM NaCl. Neither the addition of HCII alone or in combination with the LA-LMWH HCII-specific catalytic agent, i.e., V18, influenced the rate of diffusion. In fact, the combination of HCII and the LA-LMWH HCII-specific catalytic agent actually reduced the diffusion rate to a small extend. In contrast, the diffusion rate of thrombin was markedly increased when the clot was suspended in 2M NaCl.

Figure 9:
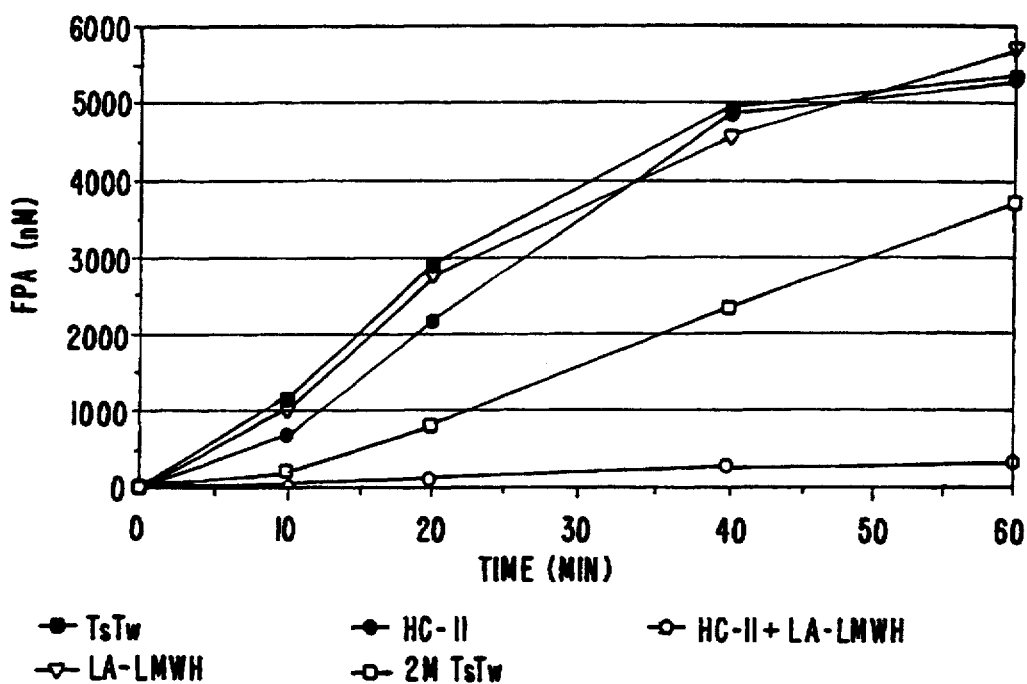
FIG. 9 illustrates the effect of 0.25 μM HCII, with and without 60 μg/ml of one of the HCII-specific catalytic agents of the present invention (i.e., V18), on the activity of fibrin-bound thrombin in purified fibrinogen.

FIG. 9 compares the catalytic activity of clot-bound thrombin measured by removing the clot after five hours of incubation with the initial solutions and suspending it in a fibrinogen solution. Clots that have been suspended in 150 nM NaCl in the presence or absence of HCII or the LA-LMWH HCII-specific catalytic agent, i.e., V18, alone generated about 6000 nM FPA. In contrast, FPA production by clots that had been suspended in 150 mM containing the combination of HCII and the LA-LMWH HCII-specific catalytic agent was suppressed by approximately 95 %. The clots that had been suspended in 2M NaCl generated about 4000 nM FPA, consistent with the fact that these contain about half the thrombin found in clots incubated in low salt buffer with or without HCII. These findings indicate that the LA-LMWH HCII-specific catalytic agent of the present invention, i.e., V18, inactivates clot-bound thrombin in the presence of HCII, but as illustrated in FIG. 8, it does this without displacing thrombin from the clot. This supports the concept that thrombin binds to fibrin via exosite 2, leaving exosite 1 available to interact with HCII (see, U.S. patent application Ser. No. 08/175,211 (filed Dec. 27, 1993), the teachings of which are hereby incorporated by reference).

Analysis of the gels indicates that a large percentage of the thrombin recovered from the clots that had been suspended in buffer containing the combination of HCII and the LA-LMWH HCII-specific catalytic agent, i.e., V18, was complexed to HCII. In contrast, predominately uncomplexed thrombin was recovered in clots suspended in buffer containing HCII alone or the LA-LMWH HCII-specific catalytic agent alone. These findings indicate that the LA-LMWH HCII-specific catalytic agent, i.e., V18, produces permanent inactivation of clot-bound thrombin by catalyzing covalent complex formation between thrombin and HCII.

D. Extracorporeal Recirculation Circuit

The selective ability to inactivate fibrin-bound thrombin was demonstrated by using an extracorporeal closed circuit containing human blood to measure the ability of various anticoagulants to inactivate surface-bound thrombin, and the thrombin clotting time was used to measure the ability of the various anticoagulants to inactivate fluid-phase thrombin. A LA-LMWH HCII-specific catalytic agent of the present invention, i.e., V18, was compared to the following anticoagulants: dermatan sulfate, low molecular weight heparin, unfractionated heparin and hirudin.

1. The Extracorporeal Closed Circuit

Figure 10:
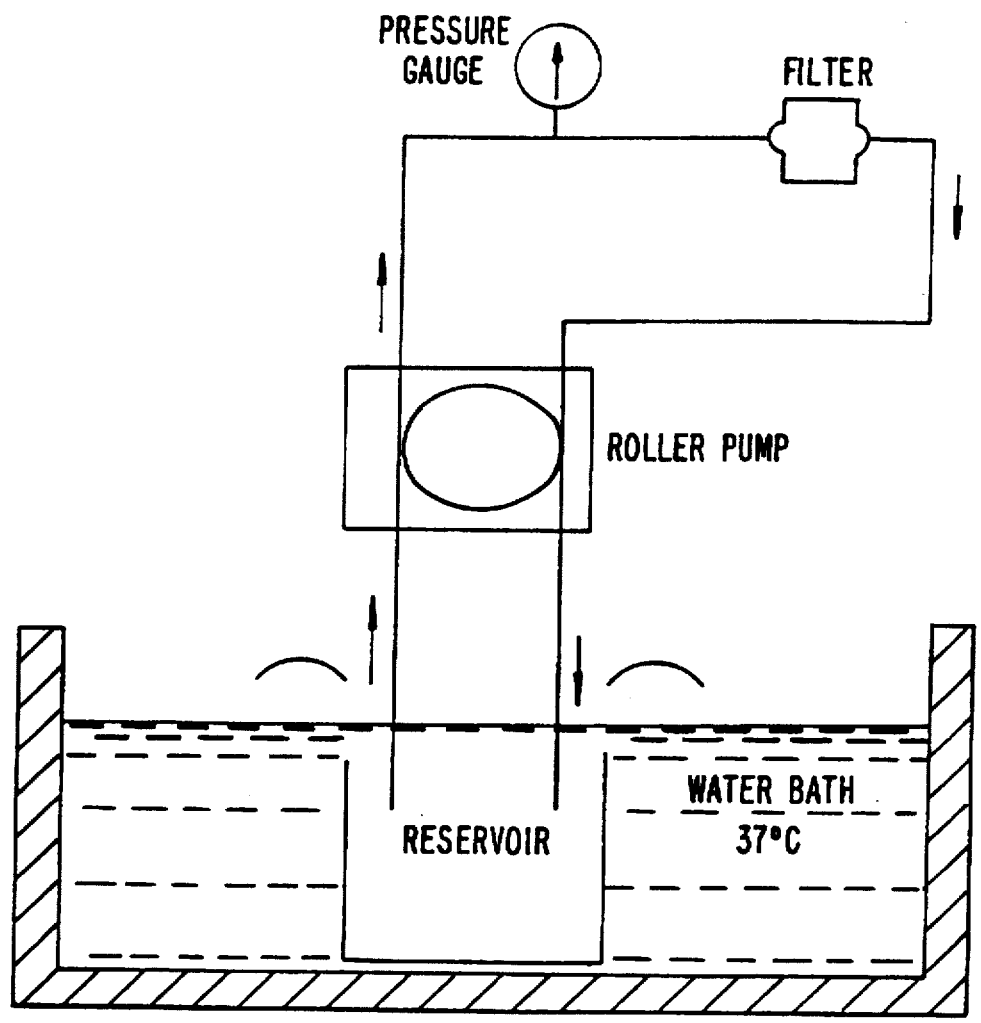
FIG. 10 illustrates the extracorporeal recirculation circuit used to examine the ability of an agent to inhibit clotting in a human whole blood system.

A diagram of the extracorporeal closed circuit is shown in FIG. 10. The circuit consists of Tygon tubing (3/16"×1/16") connected to a 40 micron transfusion filter (Pall SQ40S). The system includes 3-way stopcocks for blood sampling. A surgical pressure transducer connected to a pressure recorder (Hewlett-Packard) is connected in line with the filter so that clotting of the filter causes a steady increase in pressure. Citrated whole blood taken from normal, healthy volunteers is used. The circuit is filled with 50 ml of whole blood placed in a reservoir and kept in a waterbath maintained at 37° C. The anticoagulant to be tested is added to the circuit, clotting is initiated by recalcification (0.8 ml of 1.0M $CaCl_2$), and the blood is recirculated at a constant flow rate through the thrombogenic surface using a roller head pump (Cole-Parmer MFLX modular drive with a large F/6 roll head cartridge). Thrombosis of the filter is monitored by a change in pressure in a gauge inserted into the circuit, proximal to the filter. Progressive obstruction to flow occurs as fibrin forms on the surface of the filter and, in addition, as thrombin bound to the clot or thrombus promotes further clotting.

The inactivation of surface-bound thrombin and fluid-phase thrombin can be measured simultaneously using this system. More particularly, inactivation of surface-bound thrombin is quantified by recording the delay in clotting of the circuit. This delay is contributed to, albeit to a lesser extent, by the inactivating effect of the anticoagulant on fluid phase thrombin, whose generation is potentiated by the clot-bound thrombin. Inactivation of fluid phase thrombin is quantified by recording the thrombin clotting time of plasma prepared from blood removed from the circuit just before recalcification.

2. Results

Figure 15:
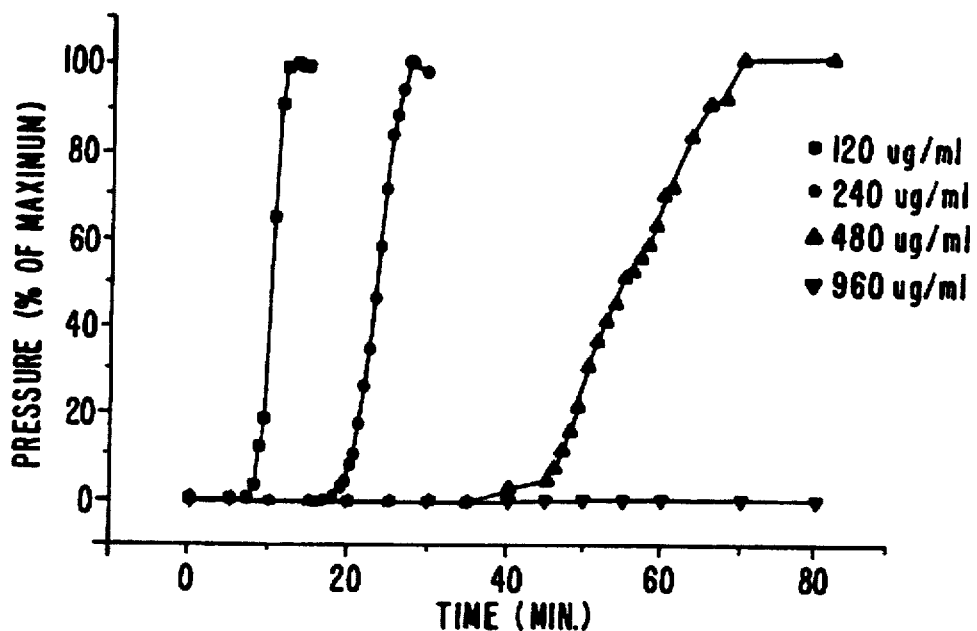
FIGS. 14 and 15 illustrate the comparative effects dermatan sulfate and one of the LA-LMWH HCII-specific catalytic agents of the present invention, i.e., V18, have on clotting in the extracorporeal recirculation circuit over a concentration range of 120 μg/ml to 960 μg/ml.
Figure 16:
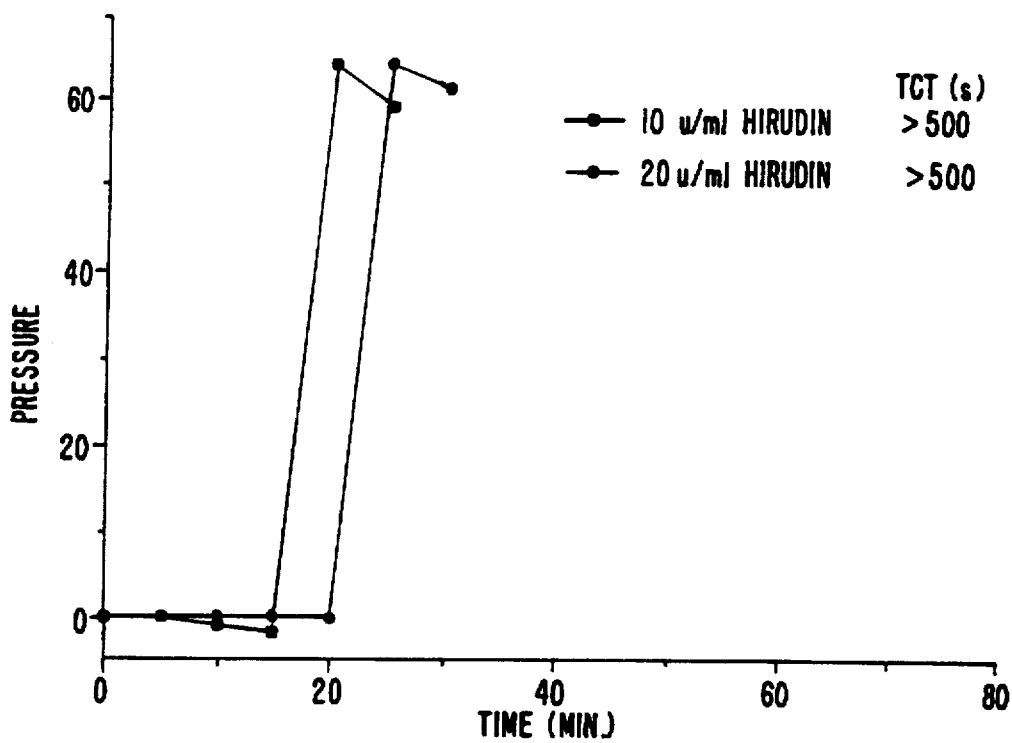
FIG. 16 illustrates the effects hirudin has on clotting in the extracorporeal recirculation circuit over a concentration range of 10 U/ml to 20 U/ml.

The following points summarize the results of experiments in which: a) one of the two HCII activators, i.e., the LA-LMWH HCII-specific catalytic agent (V18) or dermatan sulfate, was added to the blood alone (FIG. 11); b) the HCII activators were added in combination with a low concentration (less than 2% by weight) of an unmodified low molecular weight heparin (LMWH) (FIG. 12); c) the unmodified LMWH was added alone (FIG. 13); d) dermatan sulfate was added alone (FIG. 14); e) the LA-LMWH was added alone (FIG. 15); and f) hirudin was added alone (FIG. 16).

Figure 14:
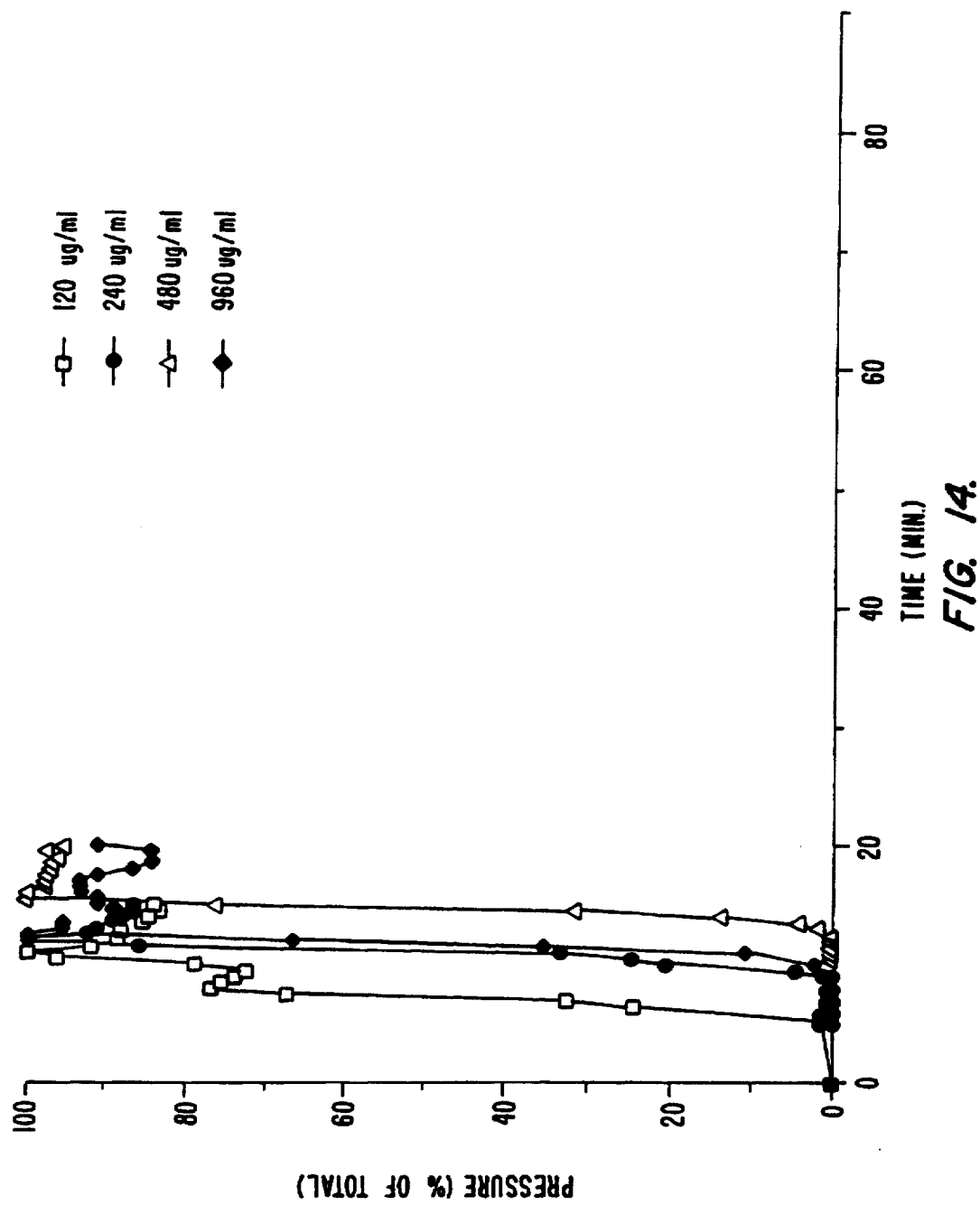

FIGS. 14 and 15 illustrate the comparative effects dermatan sulfate and the LA-LMWH HCII-specific catalytic agent of the present invention, i.e., V18, have on clotting in the circuit over a concentration range of 120 μg/ml to 960 μg/ml. As seen in FIG. 8, the LA-LMWH HCII-specific catalytic agent, i.e., V18, produces a dose-dependent inhibition of clotting in the circuit. More particularly, clotting occurs in the circuit in about 20 minutes with a LA-LMWH dose of 240 μg/ml, and is abolished with a LA-LMWH dose of 960 μg/ml. The corresponding thrombin clotting times are shown in Table 1, supra. Table 3, infra, shows the comparative effects of various concentrations of LMWH or blends of LA-LMWH with LMWH or dermatan sulfate. The thrombin clotting time was 26 seconds at a LA-LMWH concentration of 240 μg/ml, and 43.6 seconds for a LA-LMWH concentration of 960 μg/ml. In contrast, as shown in FIG. 15, clotting in the circuit occurred in less than 10 minutes with a dermatan sulfate dose of 240 μg/ml, even though the corresponding thrombin clotting time was over 500 seconds (see, Table 1, supra). Moreover, clotting in the circuit occurred in less than 20 minutes with a dermatan sulfate dose of 960 μg/ml, even though the corresponding thrombin clotting time was 841 seconds (see, Table 1, supra).

TABLE 3

THROMBIN CLOTTING TIME (2 unit)

| ADDITION | TCT (seconds) |
| --- | --- |
| Control | 21 |
| 0.5 unit/mL LMWH | 20 |
| 1.0 unit/mL LMWH | 37 |
| 2.0 unit/mL LMWH | 64 |
| 240 μg/mL LA-LMWH | 26 |
| 240 μg/mL DS | >500 |
| 0.5 unit/mL LMWH + 240 μg/mL LA-LMWH | 20 |
| 0.5 unit/mL LMWH + 240 μg/mL DS | >500 |
| 1 unit/mL LMWH + 240 μg/mL LA-LMWH | 38 |
| 1 unit/mL LMWH + 240 μg/mL DS | >500 |

Figure 11:
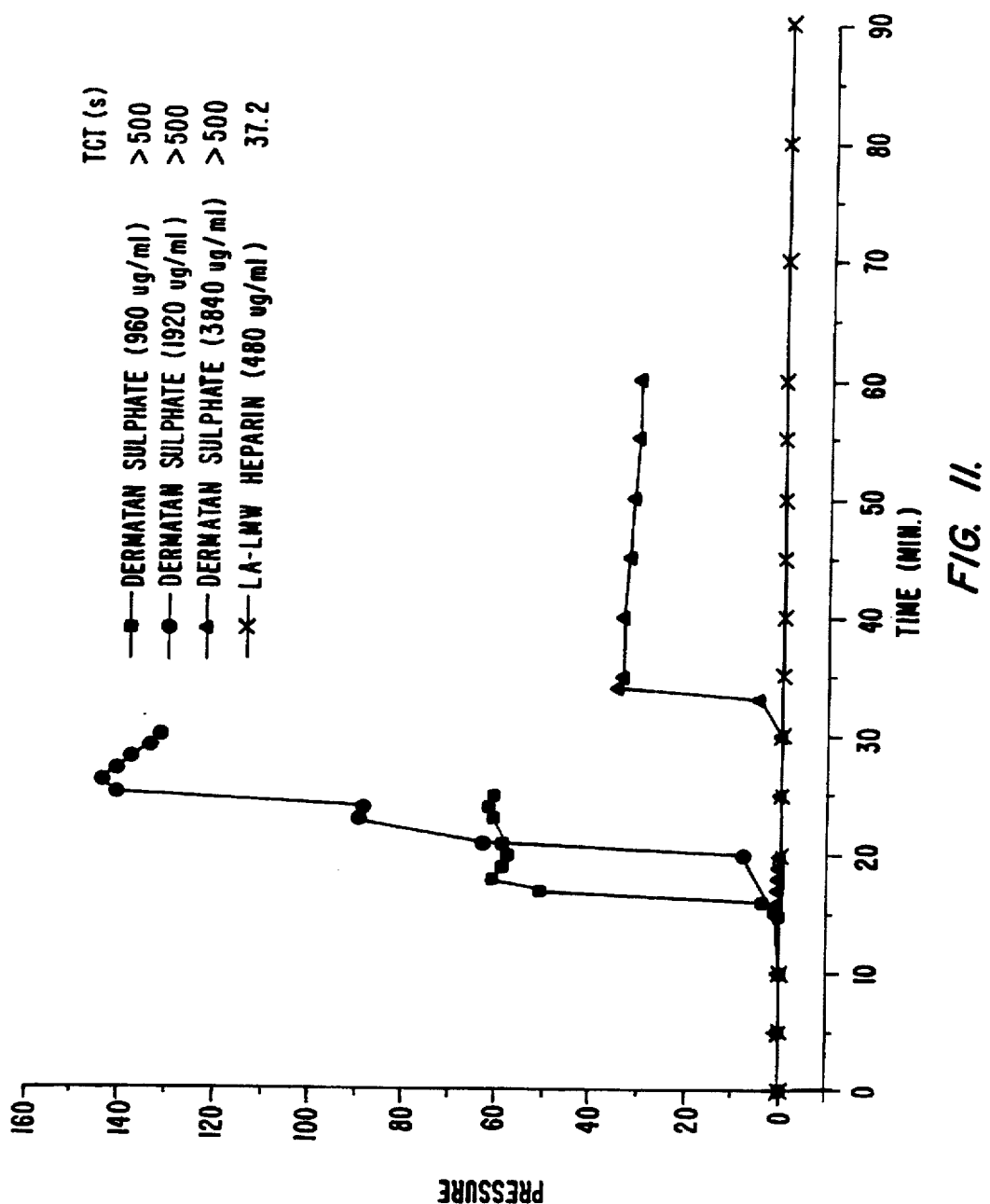
FIG. 11 illustrates the comparative effects dermatan sulfate and one of the LA-LMWH HCII-specific catalytic agents of the present invention (i.e., V18) have when aliquots of the same human blood sample were tested in the extracorporeal recirculation circuit.

LMWH-Low molecular weight heparin
LA-LMWH-Low affinity, low molecular weight heparin (V18)
DS-Dermatan sulfate In addition, the relative effects of the LA-LMWH HCII-specific catalytic agent, i.e., V18, and dermatan sulfate were compared when aliquots of the same human blood sample were tested in the model (FIG. 11). On a weight basis, the LA-LMWH HCII-specific catalytic agent is more effective than dermatan sulfate at preventing thrombosis of the circuit. Thus, 480 μg/ml of the LA-LMWH HCII-specific catalytic agent was able to completely prevent clotting for 90 minutes, whereas an 8-fold increase in the amount of dermatan sulfate could not totally prevent clotting in the circuit. In contrast, dermatan sulfate is a much more effective inhibitor of fluid phase thrombin (see, Table 1, supra). For example, in this experiment at 240 μg/ml, the thrombin clotting time for the LA-LMWH HCII-specific catalytic agent is about 26 seconds (control 21 seconds) compared to greater than 500 seconds for dermatan sulfate.

Figure 13:
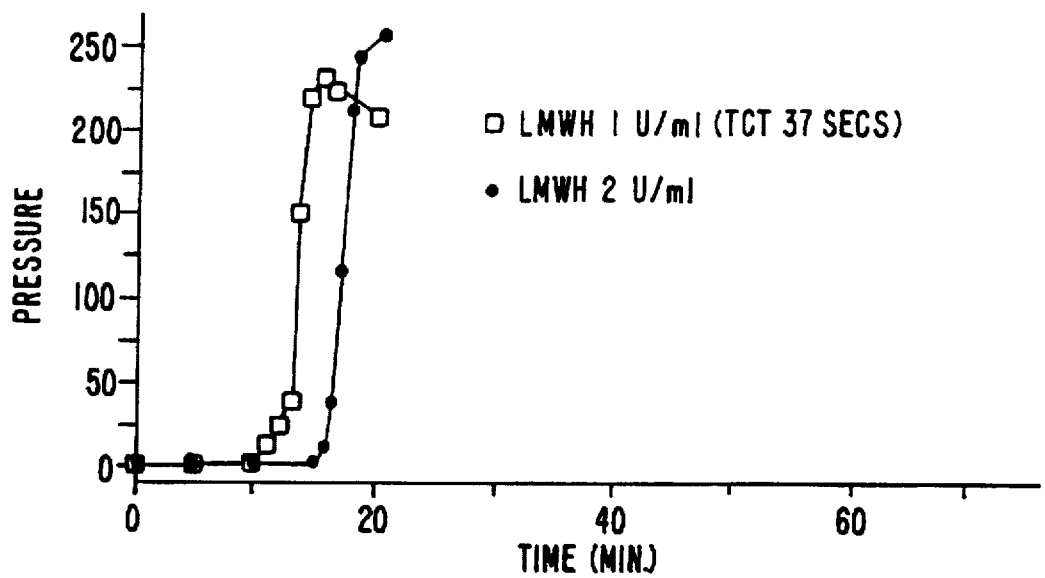
FIG. 13 illustrates the effects of 1 anti-Xa unit/ml and 2 anti-Xa units/ml of unmodified LMWH on clotting of the filter and on the thrombin clotting time (TCT).

FIG. 13 illustrates the effects of 1 anti-Xa unit/ml and 2 anti-Xa units/ml of unmodified LMWH on clotting of the filter and on the thrombin clotting time. At these concentrations, the LMWH has minimal effects on preventing shunt thrombosis even though the thrombin clotting time was prolonged to 37 and 64 seconds, respectively (see, Table 3, infra).

Figure 12:
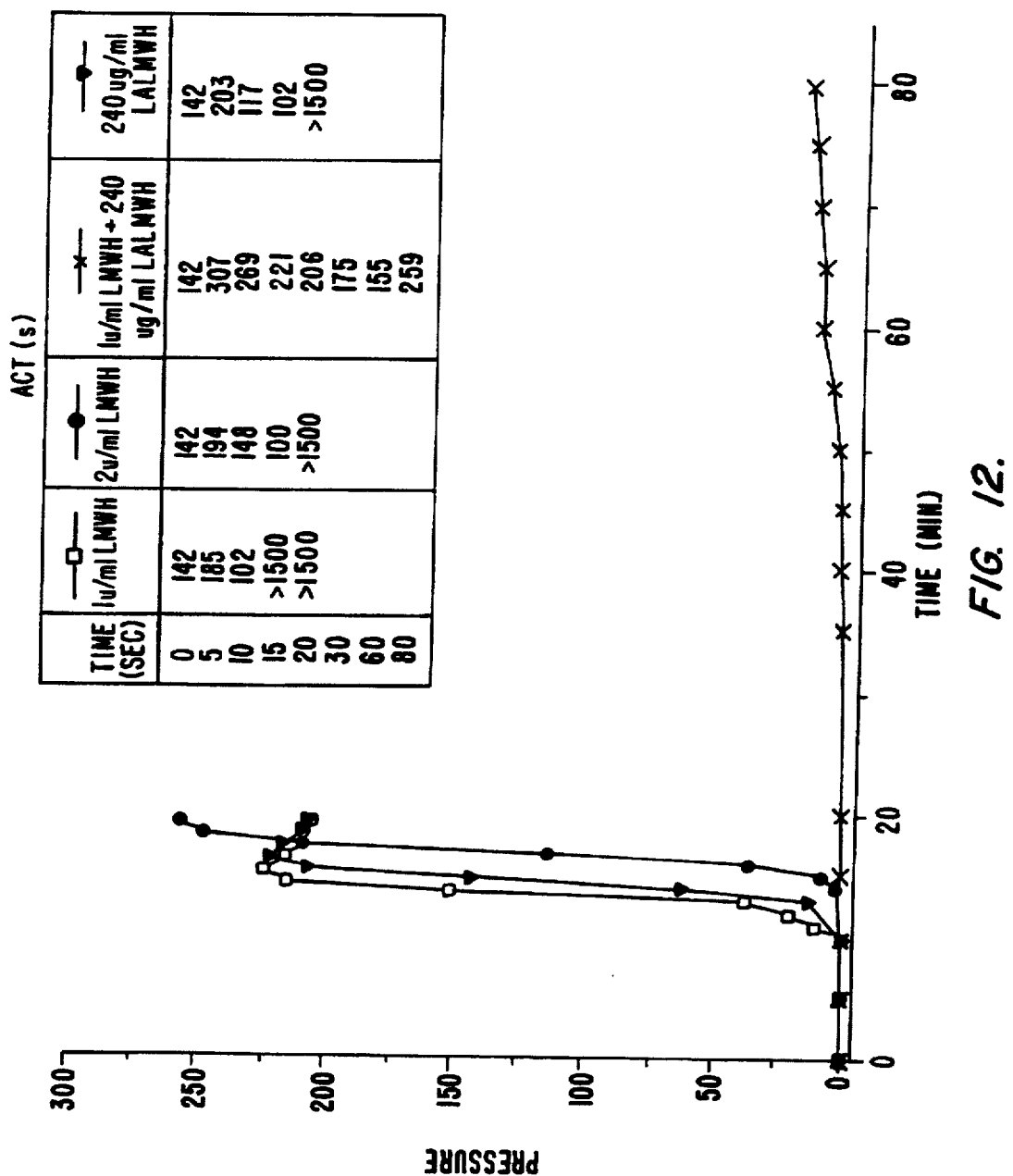
FIG. 12 illustrates the results of using a blend of a LA-LMWH HCII-specific catalytic agent, i.e., V18, and an ATIII catalytic agent (e.g., heparin).

FIG. 12 illustrates the results of using a blend of a HCII-specific catalyst, i.e., V18, and an efficient ATIII catalyst (e.g., LMWH). At concentrations of 0.5 anti-factor Xa units/ml of LMWH (which produced a thrombin clotting time of 20 seconds), unmodified LMWH was ineffective at preventing clotting of the filter, but when the same amount of LMWH was used in conjunction with 240 μg/ml of the LA-LMWH HCII-specific catalytic agent, i.e., V18, the blend was highly effective in inhibiting clotting of the filter. The blend of the LMWH and dermatan sulfate was also very effective. However, the corresponding thrombin clotting time for the LMWH/dermatan sulfate combination was greater than 500 seconds, whereas the corresponding thrombin clotting time for the blend of the LMWH/LA-LMWH HCII-specific catalytic agent was only 20 seconds (see, Table 3).

These findings clearly indicate that compared to dermatan sulfate, the LA-LMWH HCII-specific catalytic agent of the present invention, i.e., V18, has selective activity against fibrin-bound thrombin. Thus, it is more effective than dermatan sulfate at preventing filter clotting, but it produces much less prolongation of the thrombin clotting time because it has less inhibitory activity against fluid phase thrombin.

In contrast to the LA-LMWH HCII-specific catalytic agent, hirudin is much less effective at preventing thrombosis in the circuit at concentrations which prolong the thrombin clotting time to over 500 seconds, at concentrations which prolong the thrombin clotting time to less than 500 seconds (see, FIG. 16 and Table 1), and when a combination of the LA-LMWH HCII-specific catalytic agent and LMWH are used to prolong the thrombin clotting time to less than 30 seconds (see, FIG. 13 and Table 1).

Figure 17:
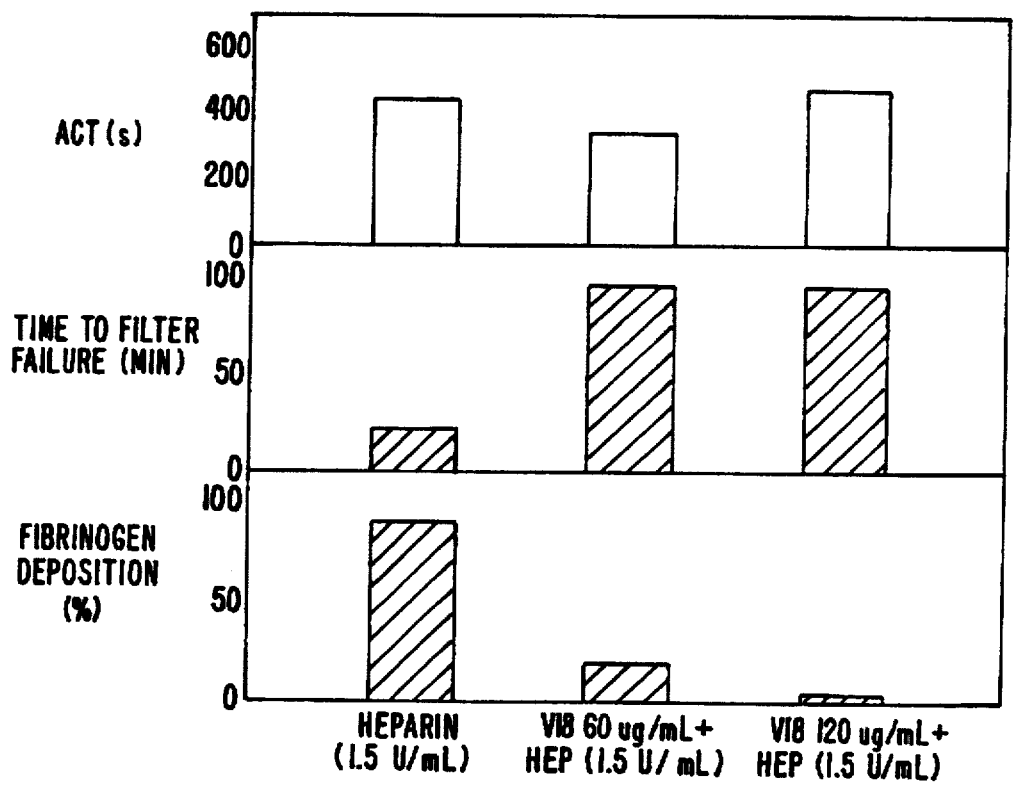
FIG. 17 illustrates the effect of heparin or heparin in combination with V18 in a bypass simulation model.

FIG. 17 illustrates the effect of heparin or heparin in combination with V18 in a bypass simulation model. In addition, Table 4 sets forth the relationship between ACT and fibrinogen deposition on a bypass filter. In Table 4, heparin alone is compared with heparin in combination with V18.

TABLE 4

RELATIONSHIP BETWEEN ACT AND FIBRINOGEN DEPOSITION ON BYPASS FILTER: COMPARISON OF HEPARIN ALONE WITH A COMBINATION OF HEPARIN AND V18

|  | ACT (s) | Fibrinogen Deposition (%) |
|---|---|---|
| Heparin (2.0 U/mL) | 651 | 36 |
| Heparin (1.5 U/mL) | 452 | 84 |
| Heparin (1.5 U/mL) and V18 (0.2 mg/mL) | 453 | 5 |

E. Animal Disease Models of Venous Thrombosis Prevention

Example I

1. Surgical Procedures

Studies were done in male New Zealand white rabbits weighing between three and four kilograms. The right and left jugular veins were exposed through a ventral incision in the neck. A 2 cm segment of each jugular vein was identified and side branches were ligated. After a venous blood sample was collected for coagulation studies, the animals were randomized to receive an intravenous bolus of either low affinity standard heparin, low affinity low molecular weight heparin, or saline. Four minutes after this treatment, a second blood sample was collected for coagulation studies. A 4 French balloon catheter was then introduced into the right jugular vein and the balloon was inflated and the endothelium within the 2 cm jugular vein segment was damaged by 15 passages of the inflated balloon. Stasis was then induced within the 2 cm segment by placing two tourniquets approximately 2 cm apart around the blood filled segment. As soon as this was done, an intravenous bolus of thromboplastin (7 mg/kg) was injected into the left jugular vein and stasis in this vein was induced by placing two tourniquets 2 cm apart around a blood filled segment. After 15 minutes of venous occlusion, a blood sample was taken for coagulation studies and the venous segments were then explanted and the clots contained therein were weighed.

2. Results

Figure 18:
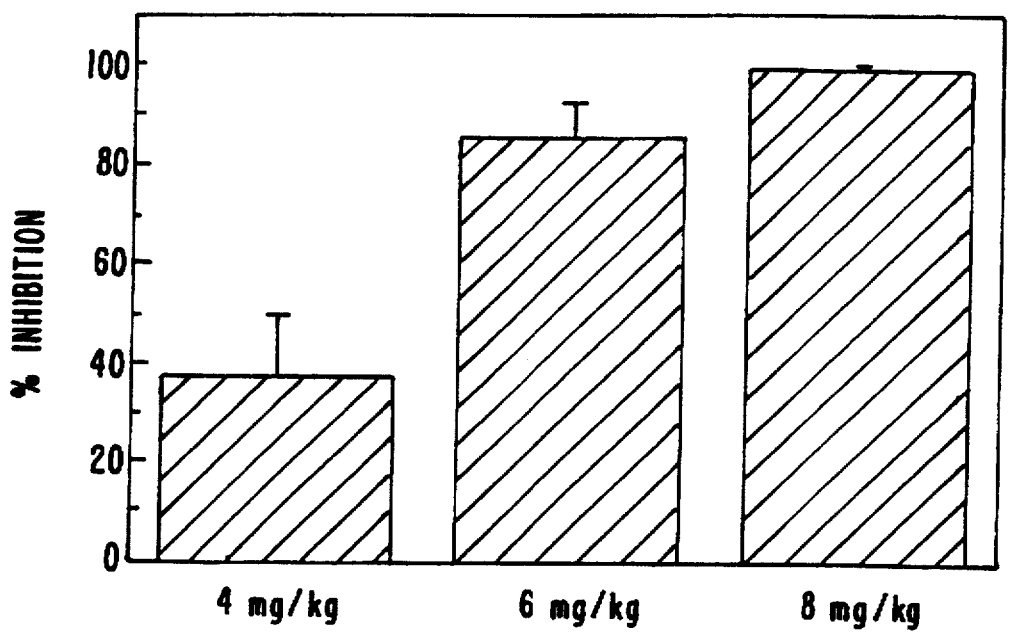
FIG. 18 illustrates the effect of one of the LA-LMWH HCII-specific catalytic agents of the present invention, i.e., V18, on clot weight after balloon injury.
Figure 19:
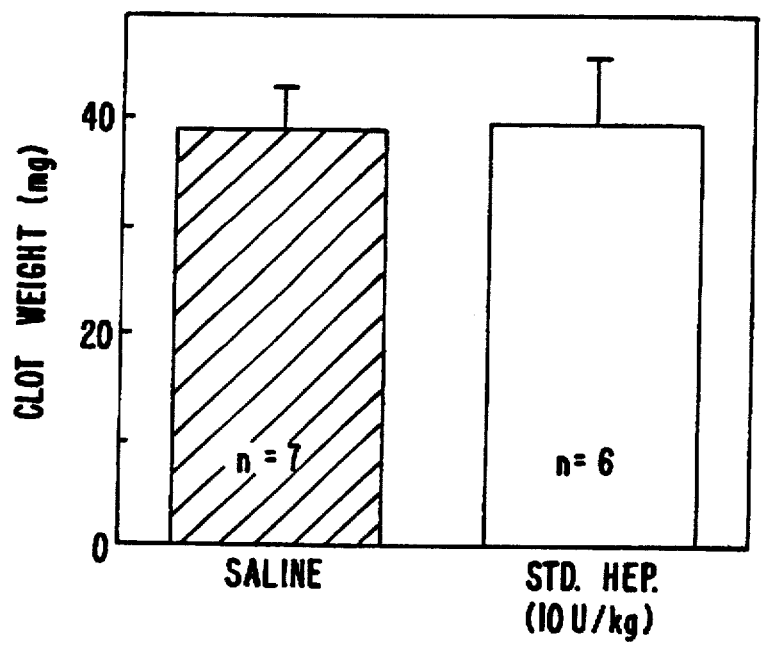
FIG. 19 illustrates the effect of standard heparin on clot weight after balloon injury.
Figure 20:
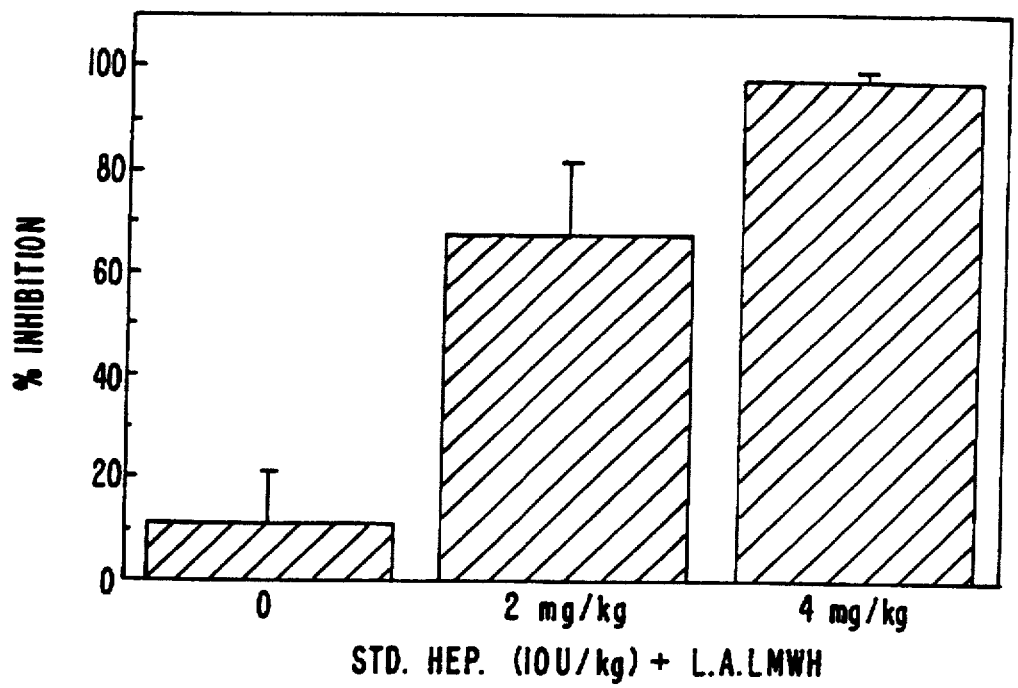
FIG. 20 illustrates the effect of standard heparin and one of the LA-LMWH HCII-specific catalytic agents of the present invention, i.e., V18, on clot weight after balloon injury.

The LA-LMWH HCII-specific catalytic agents of the present invention, e.g., V18, have been studied in a rabbit model simulating prophylaxis in high risk states. A dose response relationship was established. At 8 mg/kg (about 100 μg/ml which is about five times lower than that required to prevent thrombosis in the bypass circuit), there was complete inhibition of thrombosis (see, FIG. 18). To test the synergistic effect of combining the LA-LMWH HCII-specific catalytic agent of the present invention, i.e., V18, with an ATIII catalyst, the combination of heparin at a concentration of 10 U/kg (a concentration which has no effect on thrombus formation (see, FIG. 19)) and the LA-LMWH HCII-specific catalytic agent, i.e., V18, at a concentration of 2 mg/kg and 4 mg/kg was studied. Over 60% inhibition of thrombosis was seen when 2 mg/kg of the LA-LMWH HCII-specific catalytic agent was used (a dose which had virtually no effect when used alone), and 100% inhibition of thrombosis was seen when 4 mg/kg of the LA-LMWH HCII-specific catalytic agent was used (a dose which produced less than 40% inhibition when used alone) (see, FIG. 20). The thrombin clotting time was not increased when 8 mg/kg of the LA-LMWH was used alone, or when it was used in combination with 10 U/kg heparin, indicating that effectiveness is seen with minimal inhibitory effects on free thrombin.

SH and LMWH with low affinity for ATIII (LASH and LA-LMWH; respectively) were prepared from SH (specific activity, 160 anti-Xa and anti-IIa units/mg) and LMWH (specific activity, 100 anti-Xa U/mg), respectively, by periodate oxidation and subsequent reduction as described in Casu, B., et al., "Retention of antilipemic activity by periodate-oxidized non-anticoagulant heparins," *Arzneim-Forsch/Drug Res.* 36:637–42 (1986). The anticoagulant activities of the low affinity derivatives were then compared with those of the starting materials and dermatan sulfate (DS). As illustrated in Table 5, when compared in equivalent amounts by weight, LASH and LA-LMWH, i.e., V18, are essentially devoid of anti-Xa activity, indicating that they can no longer potentiate antithrombin III-mediated inactivation of factor Xa. In addition, these low affinity derivatives have less of an effect on the thrombin clotting times (TCT) than do the parent compounds. Thus, by abolishing their ability to catalyze ATIII, their anticoagulant activity has been reduced.

TABLE 5

| GAG (conc.) | Anti-Xa U/ml |
|---|---|
| SH (0.5 U/ml) | 0.3 |
| SH (2.0 U/ml) | 1.3 |
| SH (10.0 U/ml) | 6.0 |
| LASH (3 μg/ml) | 0.07 |
| LASH (11 μg/ml) | 0.06 |
| LASH (50 μg/ml) | 0.06 |
| LMWH (0.5 U/ml) | 0.6 |
| LMWH (2.0 U/ml) | 2.8 |
| LMWH (10.0 U/ml) | 11.0 |
| LA LMWH (5 μg/ml) (V18) | 0.04 |
| LA LMWH (20 μg/ml) (V18) | 0.05 |

TABLE 5-continued

| GAG (conc.) | Anti-Xa U/ml |
| --- | --- |
| LA LMWH (100 µg/ml) (V18) | 0.06 |
| DS (1 µg/ml) | 0.05 |
| DS (10 µg/ml) | 0.06 |
| DS (100 µg/ml) | 0.05 |

When the activity of heparin fractions of different molecular weights were compared, a 9,000 Daltons fraction had activity close to that of SH, whereas a 5,000 Daltons fraction had activity closer to that of LMWH. In contrast, a 3,000 Daltons fraction had much less activity (FIGS. 5 and 6). These findings again are consistent with the concept that maximal activation of HCII occurs with heparin chains containing 20 or more monosaccharide units, which corresponds to a molecular weight of 8,000 Daltons or higher.

Example II

1. Anesthesia

Specific pathogen-free, New Zealand white male rabbits were anesthetized with an intramuscular injection of ketamine (50 mg/kg) and xylazine (2 mg/kg). Once anesthetized, the ventral cervical area was shaved and prepped with alcohol and iodine solutions. 22-gauge catheters (Becton-Dickinson, Sandy, UT) were inserted into the left central auricular artery and the marginal auricular vein for blood sample collection and for intravenous administration of fluids and anticoagulants, respectively. Once these procedures were performed, rabbits were transferred into the operating room. After a brief exposure to a mixture of isoflurane (1 to 4%), oxygen (1 L/min) and nitrous oxide (0.5 L/min) by face mask, rabbits were intubated with a No. 2 Fr endothelial tube and maintained on the same mixture of inhalational anesthetics until the end of the procedure.

2. Clot Creation

The right external jugular and the facial vein were exposed through a ventral cervical skin incision. A segment of the facial vein was occluded with two No. 4-0 silk sutures placed 0.5 cm apart. All side branches of the jugular vein were ligated over a 2 cm length. After introducing a No. 3 Fr Fogarty thrombectomy catheter into the jugular vein through the occluded segment of the facial vein, the balloon was inflated and the endothelium lining the 2 cm segment of jugular vein was damaged by 15 passages of the catheter. Two No. 40 silk sutures were placed around the damaged vein 1.5 cm apart. The Fogarty catheter was removed and replaced with #60 polyethylene tubing passed into the isolated jugular vein segment. Blood was evacuated from the damaged vein and the segment was occluded with the sutures. The vein segment was flushed with 500 U of bovine thrombin diluted in 0.5 ml of saline for 5 minute taking care that the venous segment was totally occluded thereby preventing systemic delivery of thrombin. The thrombin solution was withdrawn and the segment was then flushed with saline.

Approximately 1 ml of arterial blood was rapidly drawn into a 1 ml syringe and mixed with approximately 1 µCi of $^{125}$I-labeled fibrinogen. 0.2 ml of this mixture was injected into the occluded jugular vein segment. The catheter was then removed, the facial vein was ligated and the thrombus was allowed to mature for 30 minute At the same time, two 0.2 ml aliquots of the same blood were allowed to clot in test tubes for 30 minute at 37° C. Since pilot studies demonstrated that thrombi formed ex vivo are equivalent in weight and radioactivity to those formed in situ in the jugular vein, the mean weight and radioactivity of the ex vivo clots were used as an index of the mass and radioactivity of the clots in situ.

Twenty minutes after thrombin injection into the jugular vein segment, animals were given either (a) heparin, 70 U/kg IV bolus and 280 U/kg s.c. 96 h X 2, (b) dermatan sulfate, 2 mg/kg IV bolus and 8 mg/kg s.c. q6h X 2, (c) V-18, 2 mg/kg IV bolus and 8 mg/kg s.c. q6h X 2, (d) a combination of heparin and dermatan sulfate in the same doses, or (e) a combination of heparin and V-18 in the same doses. Control animals were given equivalent volumes of saline at the same intervals. After 30 minutes of thrombus maturation, the tourniquets were removed and two 4-0 silk sutures were placed through the jugular vein wall into the thrombus to prevent its migration. The occluding tourniquets were then removed and blood flow through the jugular vein segment was restored. The cervical incision was flushed with 0.5 ml of penicillin and the skin was closed in a routine manner. Rabbits were left to recover breathing 100% oxygen. When they regained a gag reflex, the endotracheal tube was removed, and the animals were transferred into the recovery room.

Figure 21:
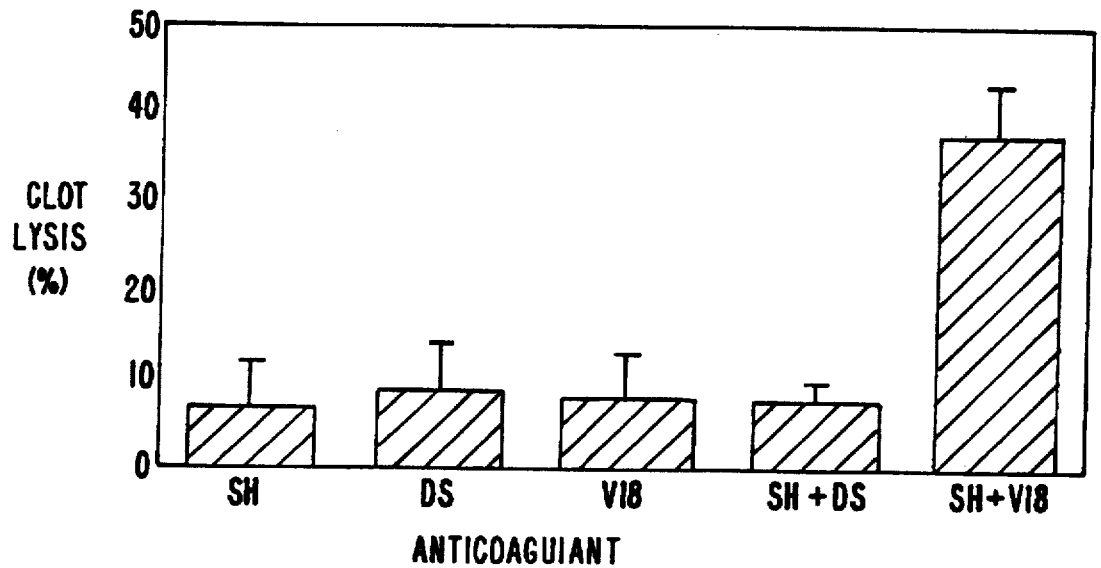
FIG. 21 illustrates the effect of various anticoagulants on clot lysis using the Rabbit Venous Thrombosis Treatment Model.
Figure 22:
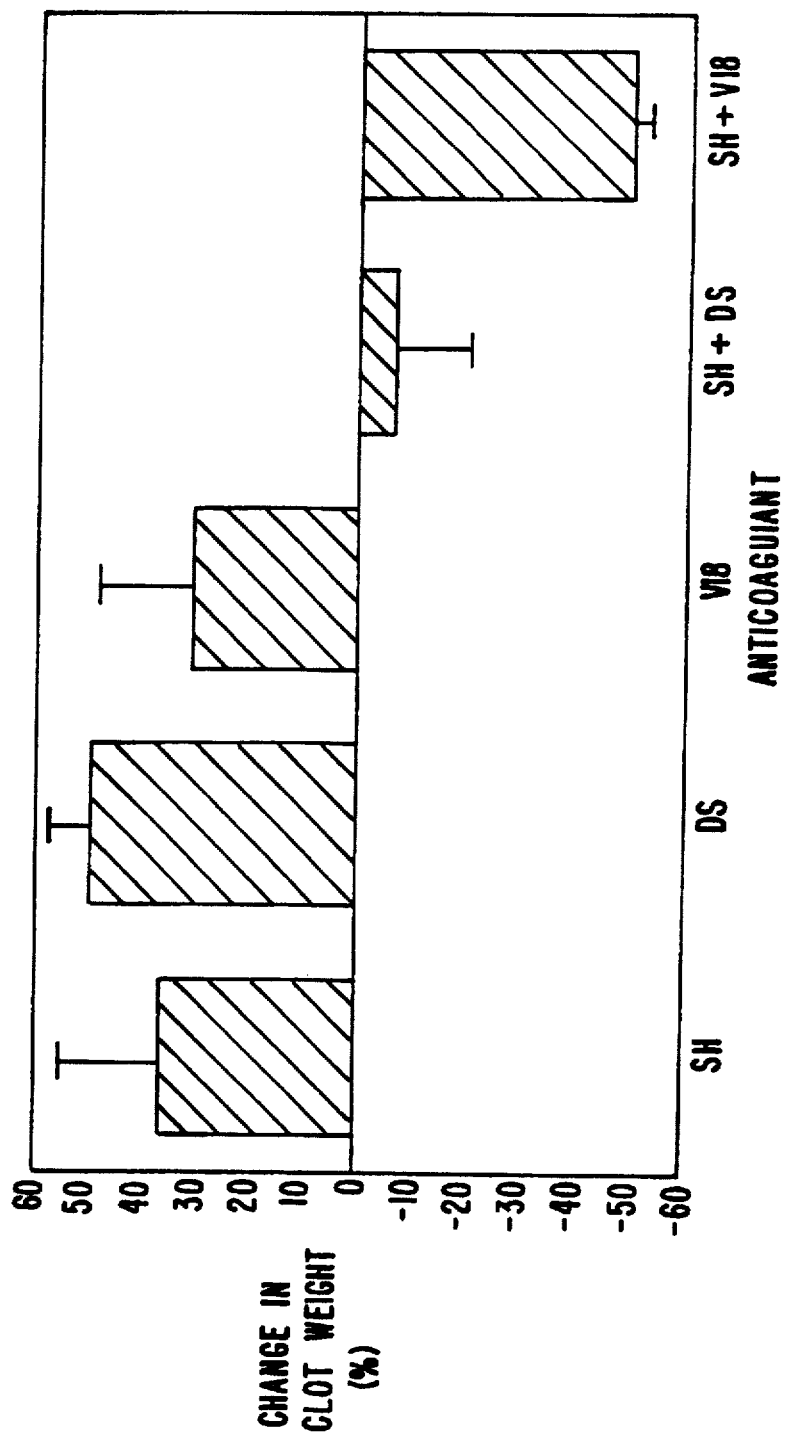
FIG. 22 illustrates the of various anticoagulants on clot accretion using the Rabbit Venous Thrombosis Treatment Model.

3. End-points 24-h after thrombus creation, the animals were euthanized and the jugular segment was opened and the residual clot was weighed and counted for radioactivity. By comparing these results with the weight and radioactivity of the clots formed ex vivo, the percentage change in clot weight (clot accretion) and radioactivity (clot lysis) were calculated (See, FIGS. 21 and 22).

F. Coagulation Profile Of V18 And Its Fractions Compared With Low Molecular Weight Hepatin And Dermatan Sulfate In Normal and ATIII- And HCII-Deficient Plasmas Coagulation studies were performed to characterize the anticoagulant profile of V18 and three V18 fractions which were separated by gel exclusion chromatography to yield Fraction 1 (mean MW 8,000), Fraction 2 (mean MW 5,000) and Fraction 3 (mean MW 3,000). In addition, because V18 is a modified LMWH with some characteristics of Dermatan Sulfate (DS), the anticoagulant profile of V18 was compared with these two sulfated polysaccharides. Such comparisons were made using the thrombin clotting time (TCT) assay, the activated partial thromboplastin time (APTT) assay, and the factor Xa clotting time (Xa time) assay. These three assays were carried out in normal plasma, ATIII-deficient plasma and HCII-deficient plasma.

Figure 23A:
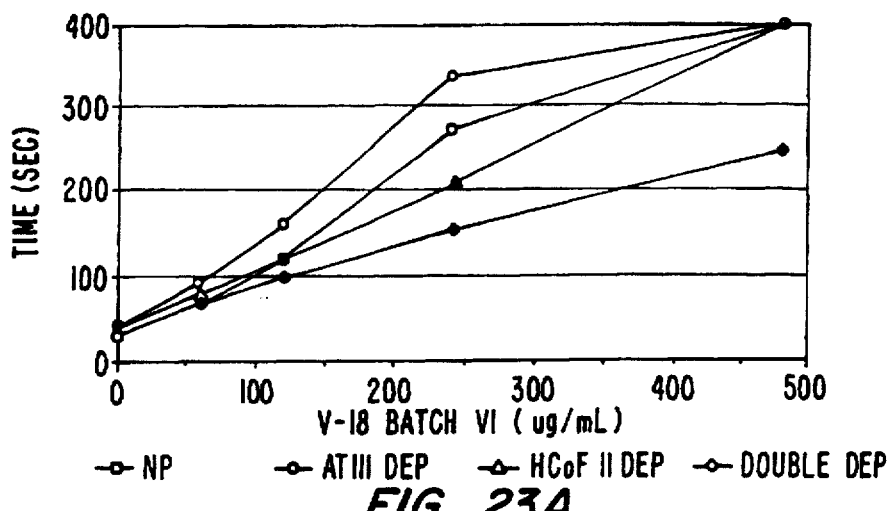
FIG. 23 illustrates the effects of V18 on the TCT (A), the APTT (B), and the factor Xa clotting time (Xa clot time) (C) in normal plasma (-+-), ATIII-deficient plasma (-■-) and HCII-deficient plasma (-⊟-).
Figure 23B:
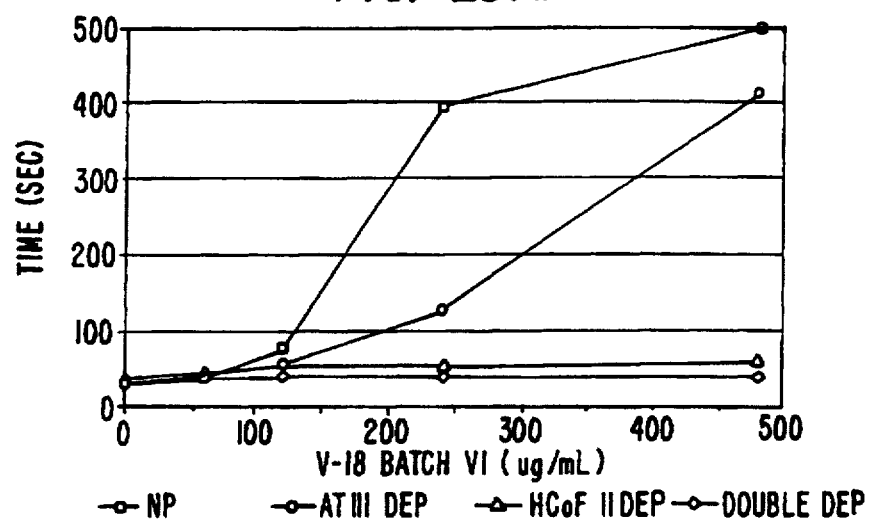
Figure 23C:
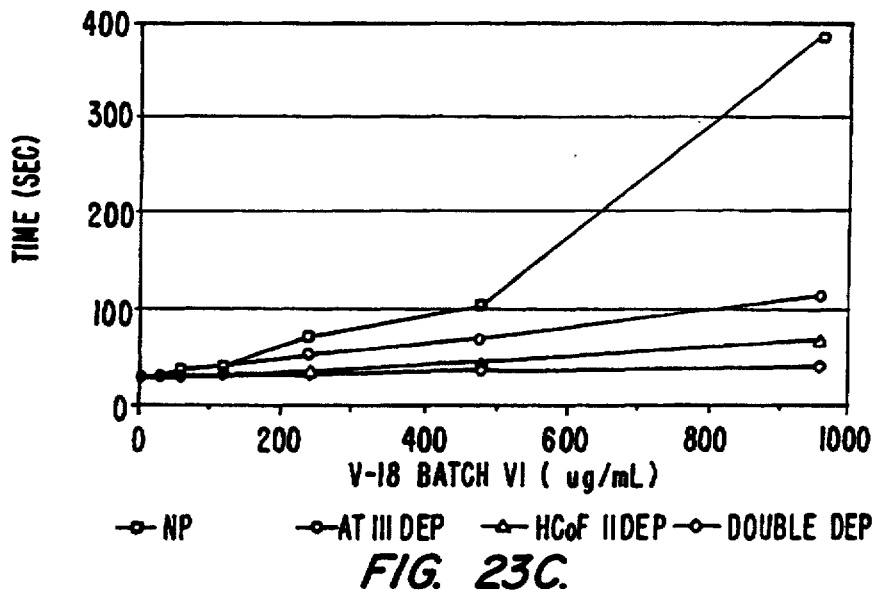

FIG. 23 illustrates the effects of V18 on the APTT (A), the TCT (B) and the factor Xa clotting time (Xa clot time) (C) in normal plasma, ATIII-deficient plasma and HCII-deficient plasma. From FIG. 23A, it is apparent that there is a dose-dependent increase in the APTT which is both ATIII- and HCII-dependent, since a similar dose-dependent prolongation is seen in normal, ATIII-depleted plasma and HCII depleted plasma. FIG. 23B illustrates that there is minimal prolongation of the TCT up to a concentration of about 120 µg/ml. Thereafter, there is a sharp increase in the TCT in the normal and ATIII-depleted plasma, but only a slight increase in the HCII-depleted plasma. Such findings indicate that V18 has weak activity against free thrombin and that this activity is largely HCII-dependent. FIG. 23C illustrates that there is a dose-dependent prolongation in the Xa clot time which is both HCII- and ATIII-dependent. These findings indicate that in addition to its activity against clot-bound thrombin, V18 has weak activity against fluid phase thrombin, which is HCII-dependent and additional anti-Xa activity which is ATIII-dependent.

Figure 24A:
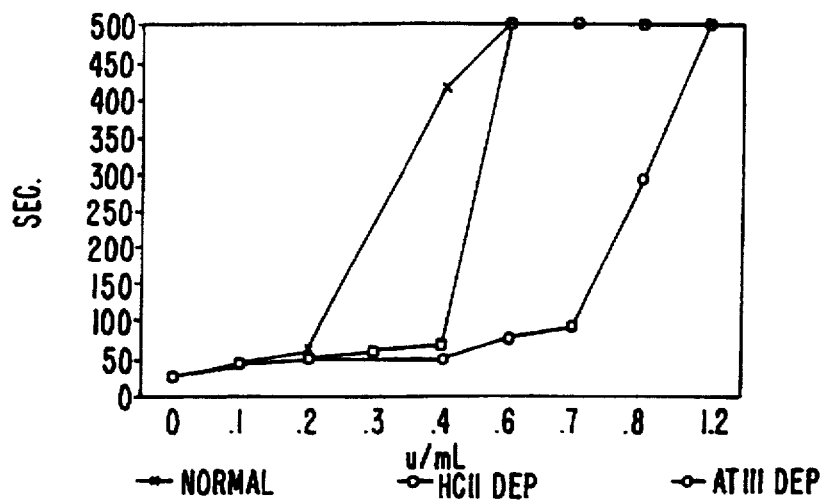
FIG. 24 illustrates the effects of LMWH on the TCT (A), the APTT (B), and the factor Xa clotting time (Xa clot time) (C) in normal plasma (-+-), ATIII-deficient plasma (-■-) and HCII-deficient plasma (-⊟-).
Figure 24B:
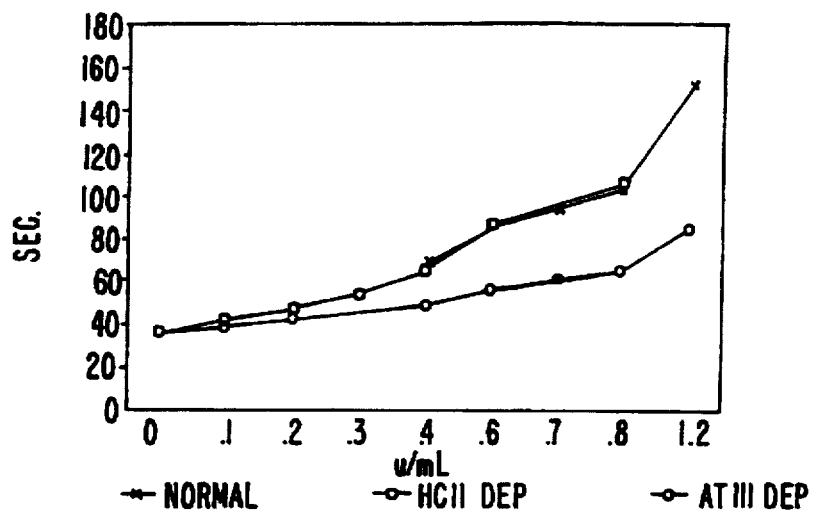
Figure 24C:
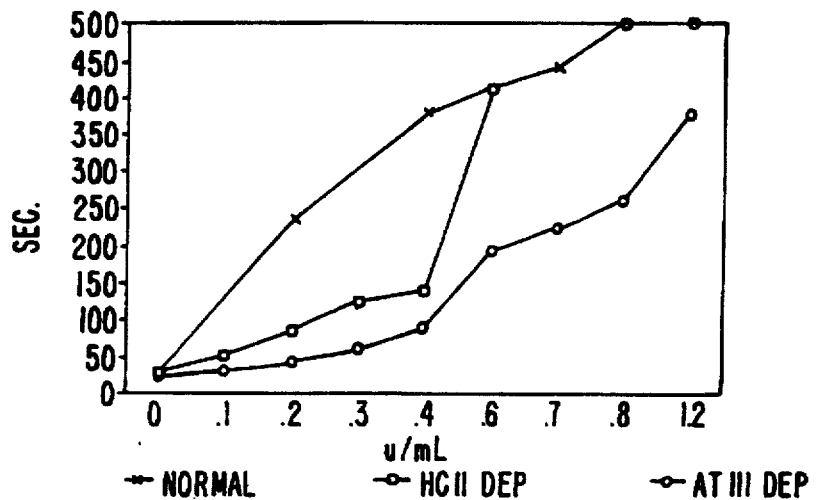
Figure 25A:
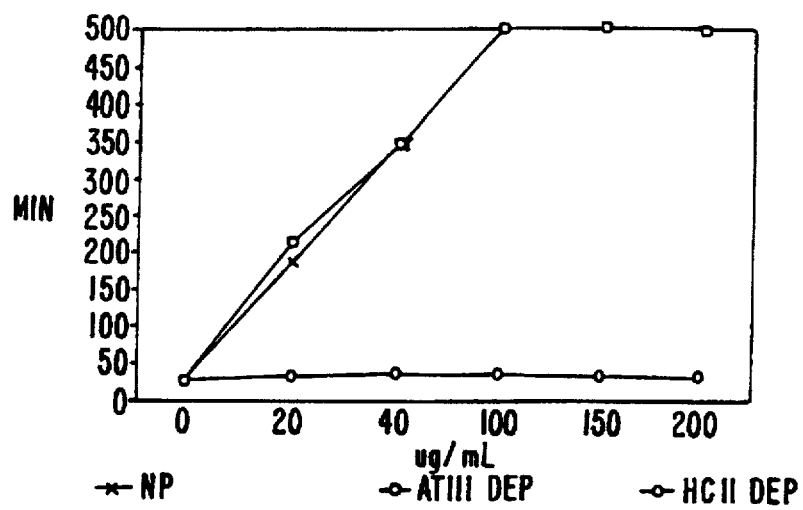
FIG. 25 illustrates the effects of Dermatan Sulfate on the TCT (A), the APTT (B), and the factor Xa clotting time (Xa clot time) (C) in normal plasma (-+-), ATIII-deficient plasma (-⊟-) and HCII-deficient plasma (-■-).
Figure 25B:
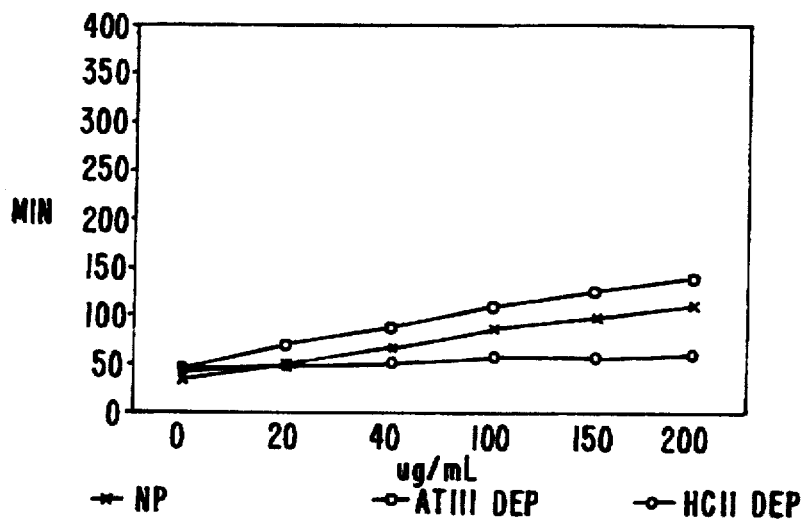
Figure 25C:
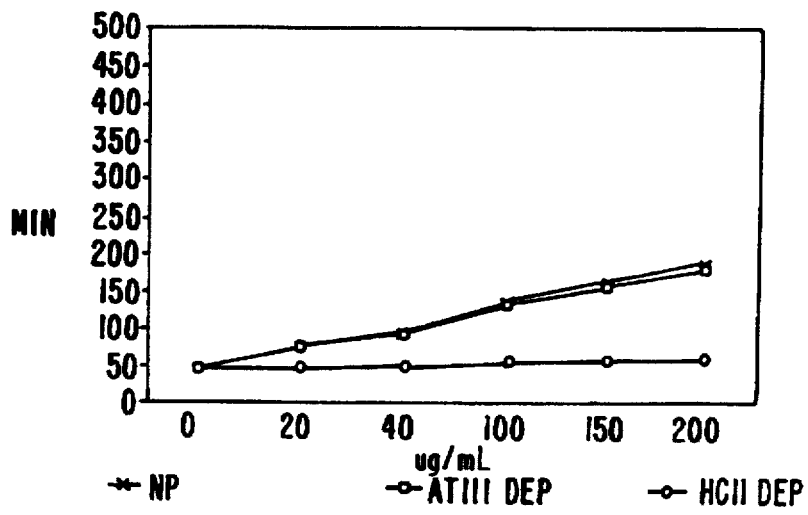

For purposes of comparison, FIGS. 24 and 25 illustrate the anticoagulant profiles of LMWH (FIG. 24) and DS (FIG. 25). In contrast to V18, the inhibitory effect of LMWH on the TCT (FIG. 24A), APTT (FIG. 24B) and Xa time (FIG. 24C) is mainly ATIII-dependent, with a minor contribution of HCII to the prolongation of the TCT and Xa time. In addition, in contrast to V18, the inhibitory effects of DS on the TCT (FIG. 25A), APTT (FIG. 25B) and Xa time (FIG. 25C) is entirely HCII-dependent.

Figure 26A:
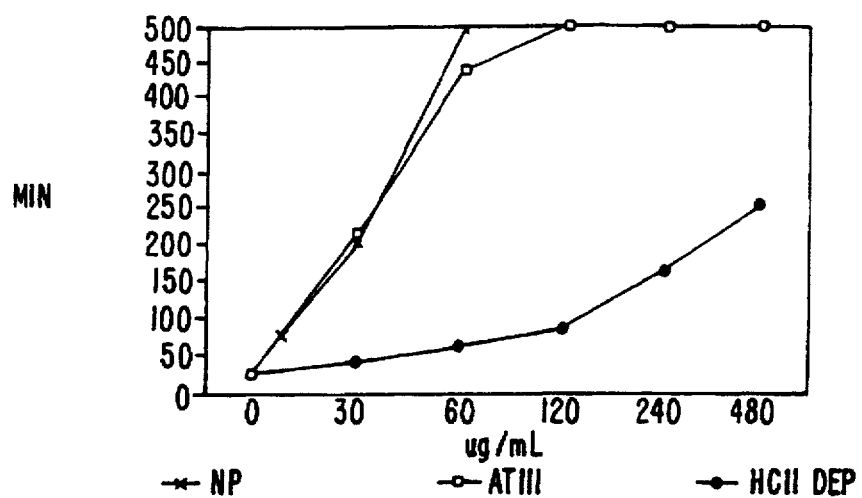
FIG. 26 illustrates the effects of Fraction 1 on the TCT (A), the APTT (B), and the factor Xa clotting time (Xa clot time) (C) in normal plasma (-+-), ATIII-deficient plasma (-⊟-) and HCII-deficient plasma (-■-).
Figure 26B:
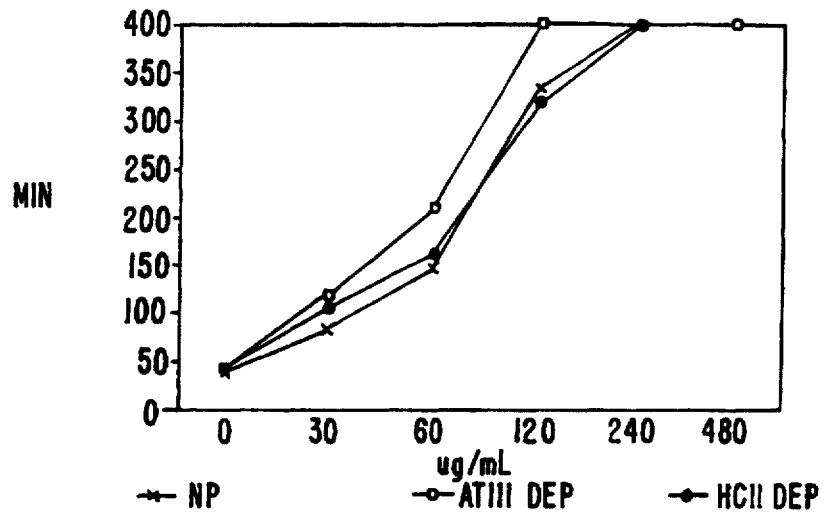
Figure 26C:
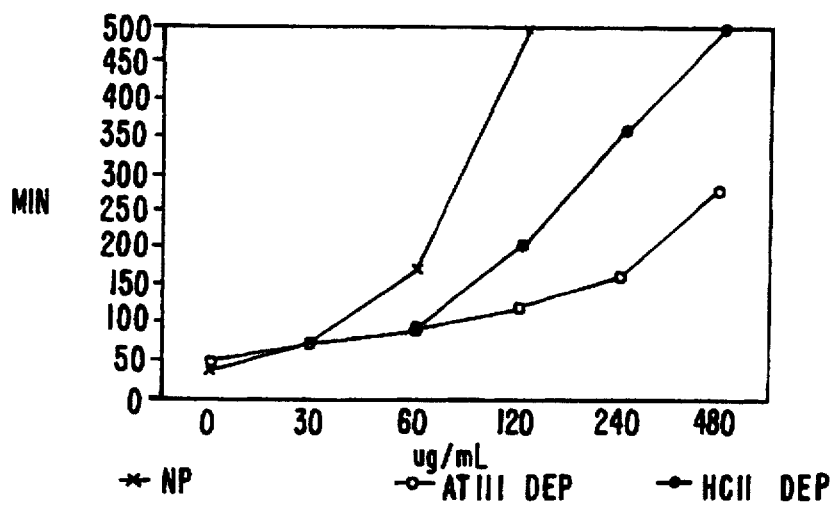
Figure 28A:
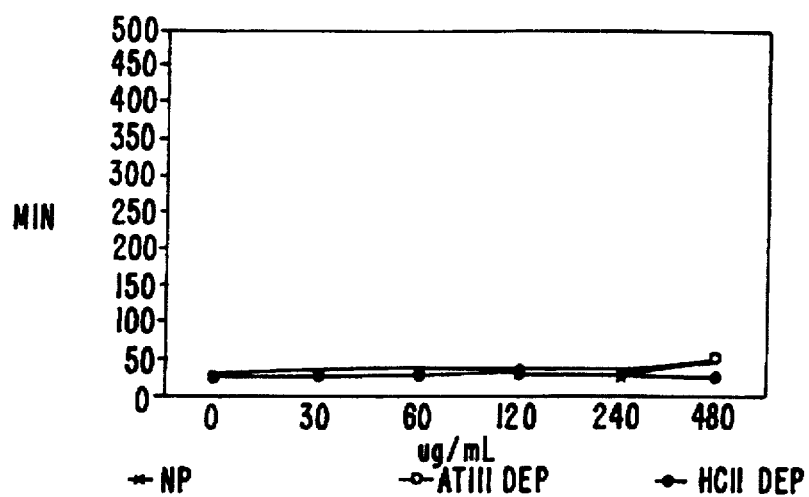
FIG. 28 illustrates the effects of Fraction 3 on the TCT (A), the APTT (B), and the factor Xa clotting time (Xa clot time) (C) in normal plasma (-+-), ATIII-deficient plasma (-⊟-) and HCII-deficient plasma (-■-).
Figure 28B:
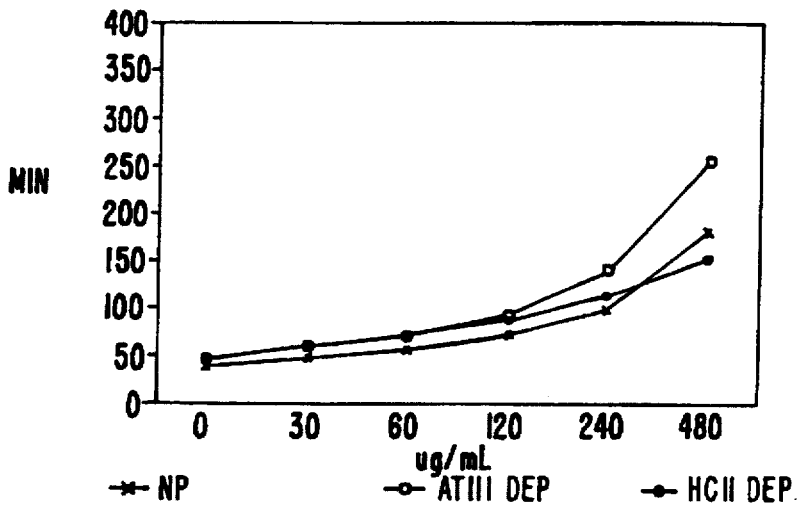
Figure 28C:
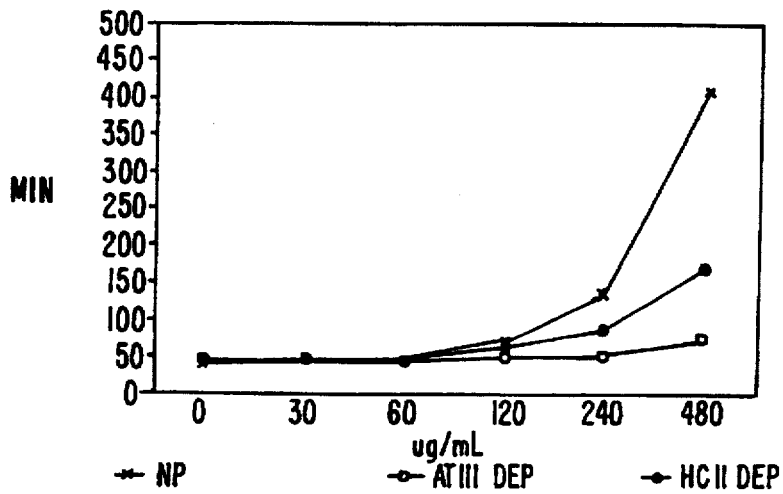

FIGS. 26, 27 and 28 illustrate the anticoagulant profiles of the three fractions of V18 which were separated by size using gel exclusion chromatography. Fraction 1 has a mean molecular weight of about 8,000, Fraction 2 has a mean molecular weight of about 5,000 and Fraction 3 has a mean molecular weight of about 3,000. The inhibitory effects of Fraction 1 on the TCT (FIG. 26A) is mainly HCII-dependent, on the APTT (FIG. 26B) both HCII- and ATIII-dependent and on Xa time (FIG. 26C) mainly ATIII-dependent. The inhibitory effects of Fraction 2 on the TCT (FIG. 27A) is HCII-dependent, on the APTT (FIG. 27B) both HCII- and ATIII-dependent and on the Xa time (FIG. 27C) mainly ATIII-dependent. In contrast to Fraction 1, Fraction 2 is much less potent against fluid phase thrombin and less potent in the APTT and Xa time assays. Fraction 3 has minimal activity in the TCT assay (FIG. 28A), and weak activity in the APTT (FIG. 28B) and Xa time (FIG. 28C) assays.

Table 6 is a summary table showing the concentrations of the various glycosaminoglycans (GAGS) required to double the APTT and TCT.

TABLE 6

| | Dosage to Double PTT & TCT ug/mL | | |
|---|---|---|---|
| | PTT x2 | TCT x2 | RATIO |
| V18 | 60 | 100 | 0.6 |
| FRACT 1 | 20 | 15 | 1.3 |
| FRACT 2 | 50 | 120 | 2.4 |
| FRACT 3 | 100 | 480 | 4.8 |
| DS | 20 | 15 | 1.3 |

Figure 29:
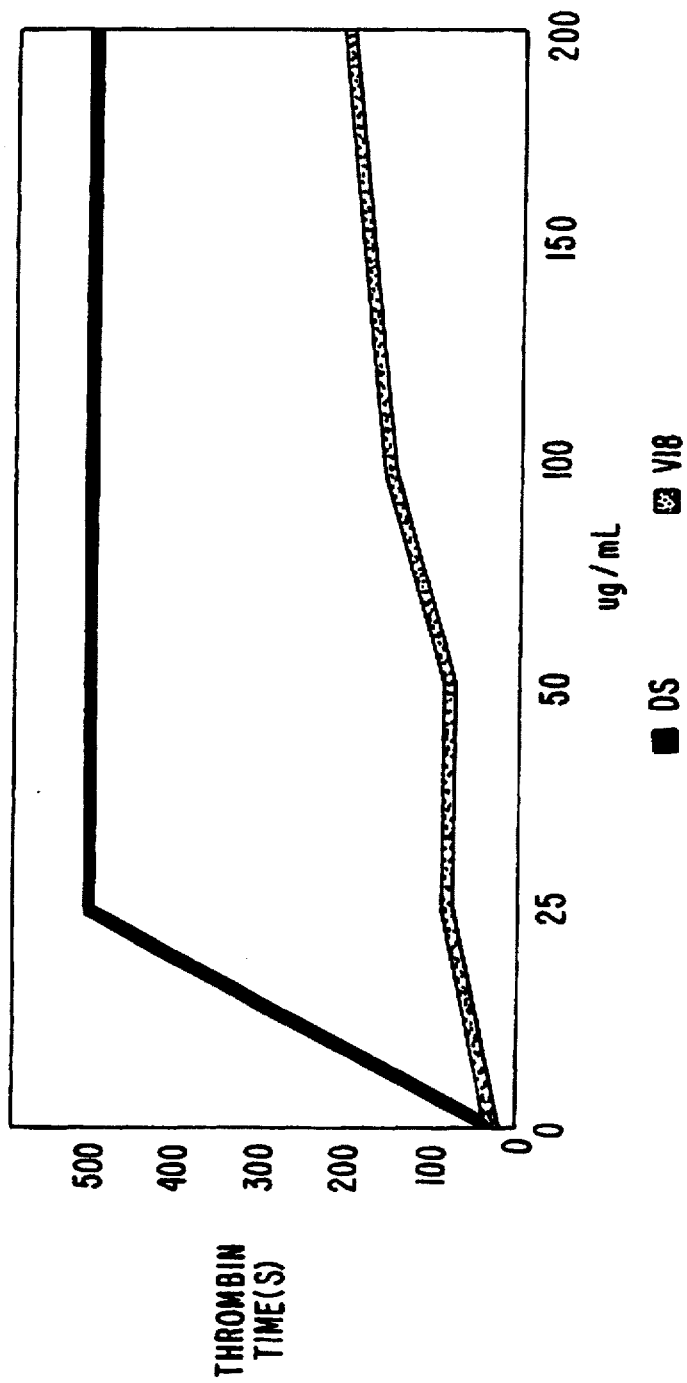
FIG. 29 illustrates the comparative additive effect of heparin (0.1 U/mL) on the prolongation of the thrombin time produced by DS and V18.

On a weight basis, DS is much more potent than V18, and DS has similar potency to Fraction 1. The fractions of V18 lose potency with reduction in molecular weight. FIG. 29 illustrates the comparative additive effect of heparin (0.1 U/mL) on the prolongation of the thrombin time produced by DS and V18.

G. Modified Whole Blood Clotting Time (WBCT) Assay For Testing Inhibition Of Free And Clot-Bound Thrombin Studies were performed to compare the effects of the various GAGS on fluid phase thrombin and clot-bound thrombin in a modified whole blood clotting time assay. Clots were prepared around polystyrene hooks by adding 250 µl $CaCl_2$ to 10 ml of platelet-poor plasma (final concentration 0.025M). The clots were allowed to age for 1 hour at 37° C. They were then removed, attached to the hooks and washed four times for 30 minutes. Control clots with PPACK-inactivated clot-bound thrombin were prepared by incubating the clots for the first 30 minute incubation with 10 µM PPACK. The whole blood clotting times were performed by adding 950 µl of human blood obtained from a normal donor to 50 µl of the anticoagulant (or buffer control). The clots (clot-bound thrombin) or PPACK clots (inactivated clot-bound thrombin) which were attached to the polystyrene hooks, or free-thrombin at a sufficient concentration to reduce the baseline clotting time to that obtained with clot-bound thrombin (free thrombin) were added to the tubes of blood which were incubating at 37° C., and the clotting time was recorded using the tilt tube method.

Figure 30:
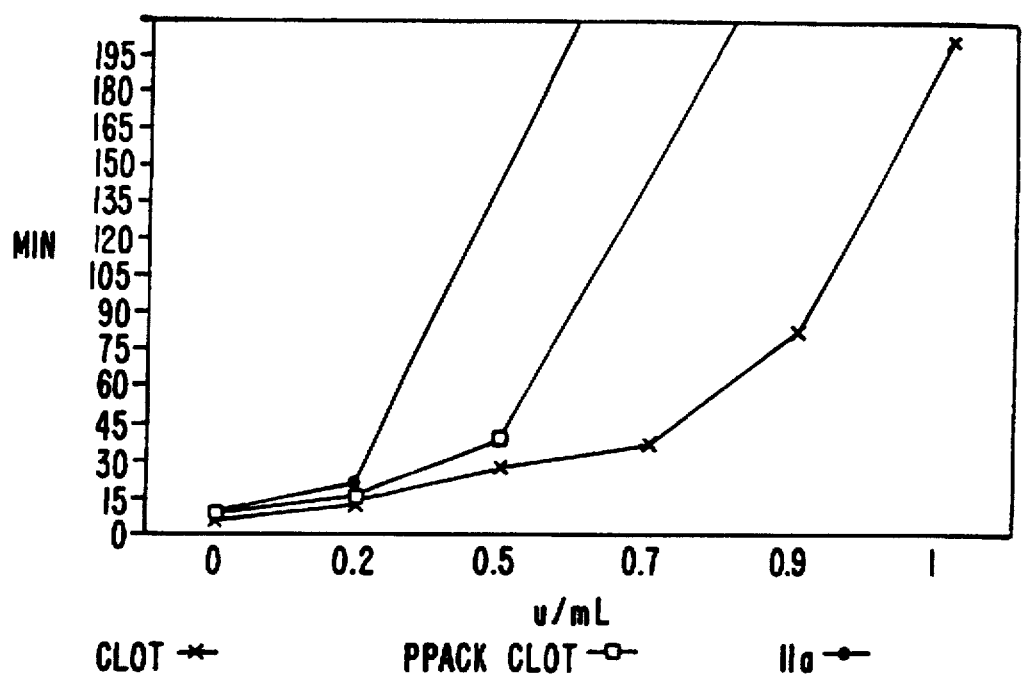
FIG. 30 illustrates the effect of increasing doses of heparin on the whole blood clotting time to which thrombin (A) (-■-), a PPACK clot (B) (-⊟-) and clot-bound thrombin (C) (-+-) is added.

FIG. 30 illustrates the effect of increasing doses of heparin on the whole blood clotting time to which thrombin (A), a PPACK clot (B) and clot-bound thrombin (C) is added. The IC 50 was 0.3 units/ml, 0.6 units/ml and 0.9 units/ml for the free thrombin, the PPACK clot and the clot-bound thrombin, respectively. Thus, the ratio for the relative sensitivity of this whole blood system to the effects of free thrombin (A) to clot-bound thrombin (C) is about 3, and the ratio for the relative sensitivity of the whole blood system to the effects of the PPACK-inactivated clot (B) to the clot-bound thrombin (C) is about 1.5.

Figure 31:
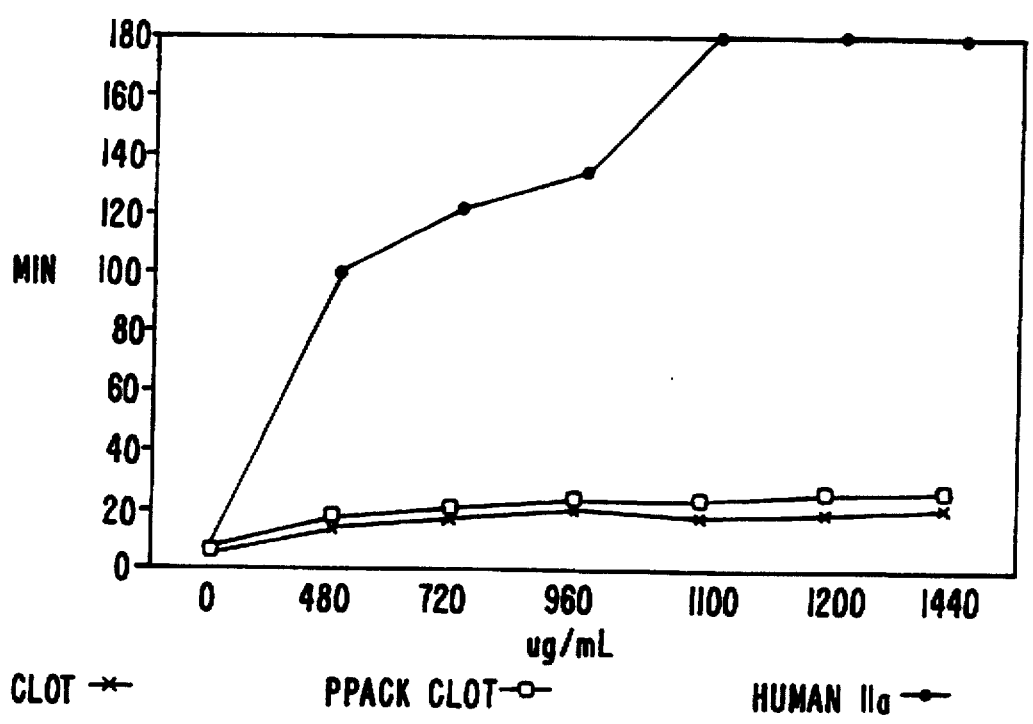
FIG. 31 illustrates the effect of increasing doses of dermatan sulfate on the whole blood clotting time to which thrombin (A) (-■-), a PPACK clot (B) (-⊟-) and clot-bound thrombin (C) (-+-) is added.

FIG. 31 illustrates the effect of increasing doses of DS on the whole blood clotting time to which thrombin (A), a PPACK clot (B) and clot-bound thrombin (C) is added. The IC 50 was 480 µg/ml for the free thrombin, and it was >1440 for both the PPACK clot and the clot-bound thrombin. Thus, the ratio for the relative sensitivity of the whole blood system to the effects of free thrombin (A) and clot-bound thrombin (C) is >3.0, and the ratio for the relative sensitivity of the whole blood system to the effects of the PPACK-inactivated clot (B) to the clot-bound thrombin (C) is >3.0.

Figure 32:
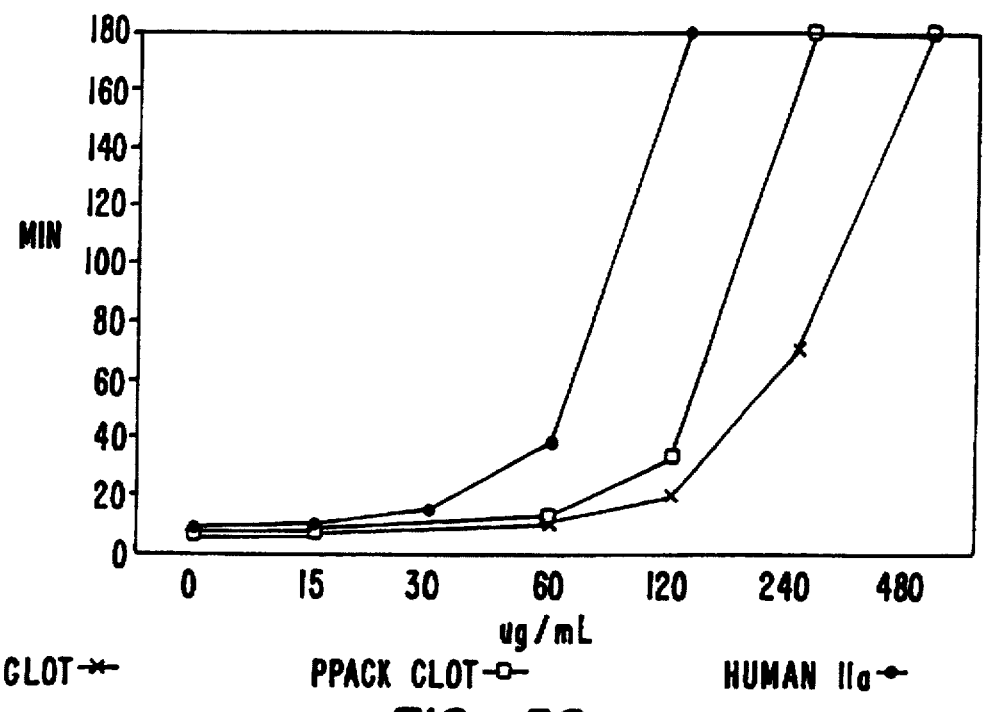
FIG. 32 illustrates the effect of increasing doses of V18 on the whole blood clotting time to which thrombin (A) (-■-), a PPACK clot (B) (-⊟-) and clot-bound thrombin (C) (-+-) is added.

FIG. 32 illustrates the effect of increasing doses of V18 on the whole blood clotting time to which thrombin (A), a PPACK clot (B) and clot-bound thrombin (C) is added. The IC 50 was 90 µg/ml, 180 µg/ml and 250 µg/ml for the free thrombin, the PPACK clot and the clot-bound thrombin, respectively. Thus, the ratio for the relative sensitivity of this whole blood system to the effects of free thrombin (A) to clot-bound thrombin (C) is about 3, and the ratio for the relative sensitivity of the whole blood system to the effects of the PPACK-inactivated clot to the clot-bound thrombin is about 1.5.

Figure 33:
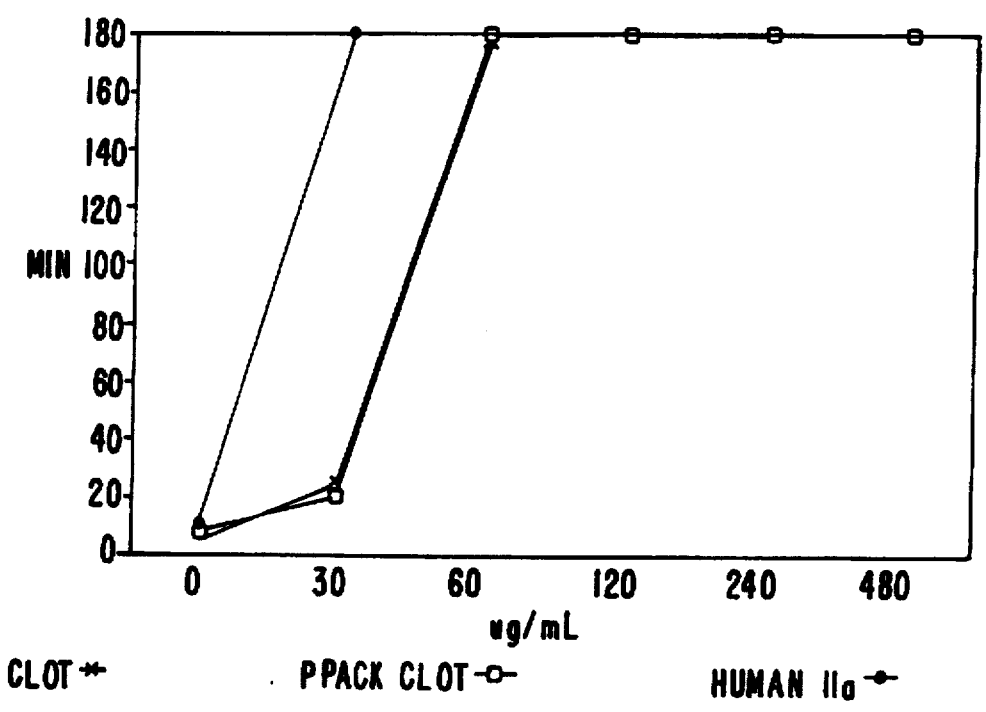
FIG. 33 illustrates the effect of increasing doses of Fraction 1 on the whole blood clotting time to which thrombin (A) (-■-), a PPACK clot (B) (-⊟-) and clot-bound thrombin (C) (-+-) is added.
Figure 34:
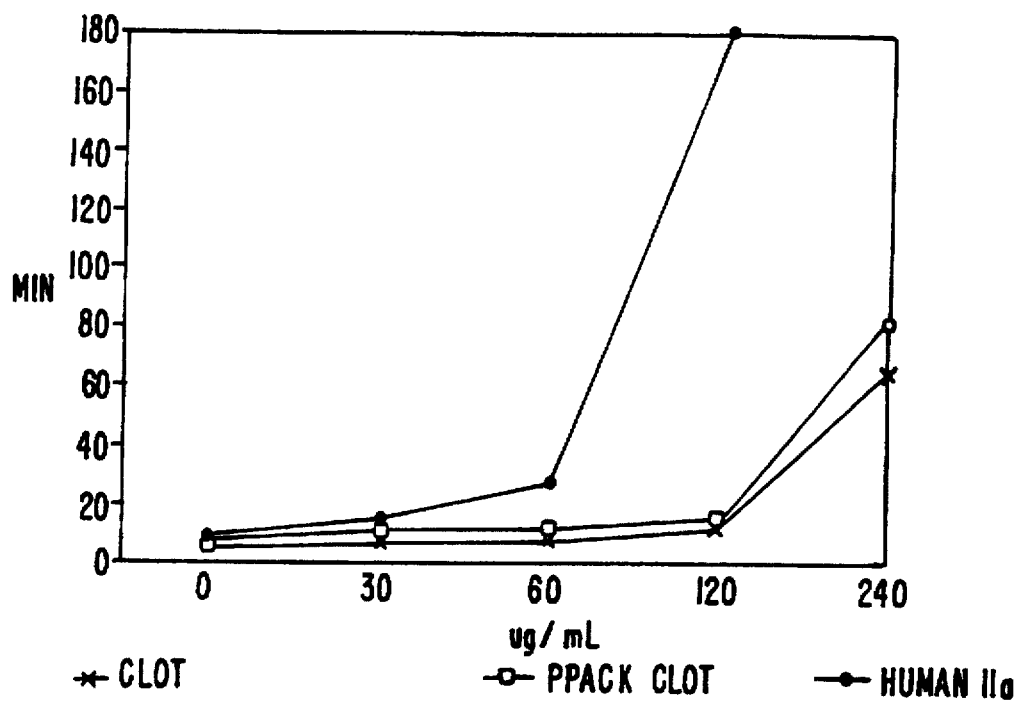
FIG. 34 illustrates the effect of increasing doses of Fraction 2 on the whole blood clotting time to which thrombin (A) (-■-), a PPACK clot (B) (-⊟-) and clot-bound thrombin (C) (-+-) is added.
Figure 35:
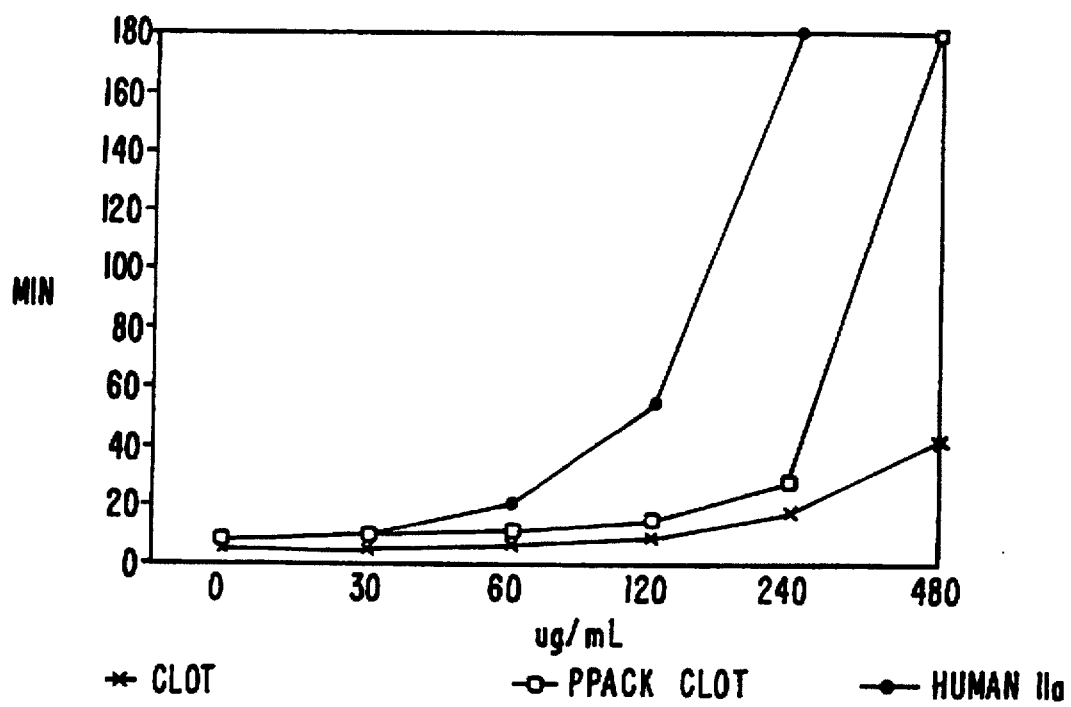
FIG. 35 illustrates the effect of increasing doses of Fraction 3 on the whole blood clotting time to which thrombin (A) (-■-), a PPACK clot (B) (-⊟-) and clot-bound thrombin (C) (-+-) is added.

FIGS. 33, 34 and 35 illustrate the effects of increasing doses of Fraction 1, 2 and 3 of V18, respectively, on the whole blood clotting time to which thrombin (A), a PPACK clot (B) and clot-bound thrombin (C) is added. For Fraction 1, the IC 50 was 22 µg/ml, 25 µg/ml and 37 µg/ml for the free thrombin, the PPACK clot, and the clot-bound thrombin, respectively. Thus, the ratio for the relative sensitivity of this whole blood system to the effects of free thrombin (A) to clot-bound thrombin (C) is about 1.7, and the ratio for the relative sensitivity of the whole blood system to the effects of the PPACK-inactivated clot (B) to the clot-bound thrombin (C) is about 1.6.

For Fraction 2, the IC 50 was 90 µg/ml, 240 µg/ml and 250 µg/ml for the free thrombin, the PPACK clot and the clot-bound thrombin, respectively. Thus, the ratio for the relative sensitivity of this whole blood system to the effects of free thrombin (A) to clot-bound thrombin (C) is about 2.7, and the ratio for the relative sensitivity of the whole blood system to the effects of the PPACK-inactivated clot (B) to the clot-bound thrombin (C) is about 1.0. For Fraction 3, the IC 50 was 150 µg/ml, 320 µg/ml and about 600 µg/ml for the free thrombin, the PPACK clot and the clot-bound thrombin, respectively. Thus, the ratio for the relative sensitivity of this whole blood system to the effects of free thrombin (A) to clot-bound thrombin (C) is about 4.0, and the ratio for the relative sensitivity of the whole blood system to the effects of the PPACK-inactivated clot (B) to the clot-bound thrombin (C) is about 1.9.

Figure 36A:
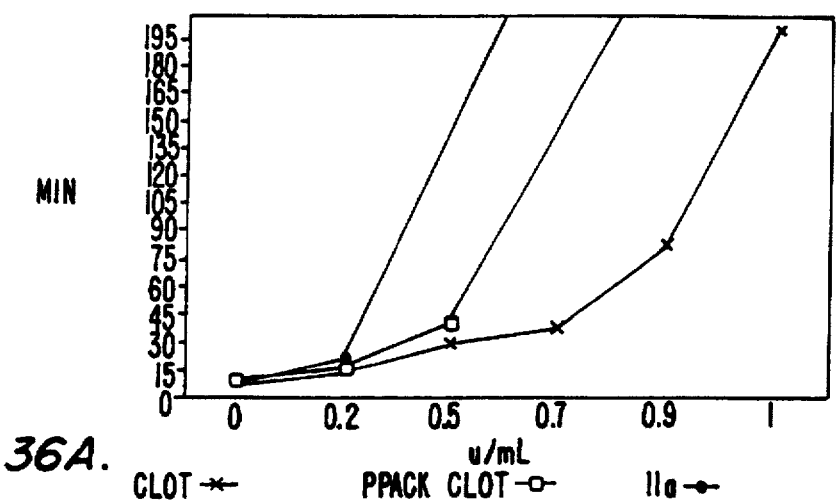
FIG. 36 compares the effects of heparin ((A), upper panel), Fraction 1 ((B), middle panel) and the combination of heparin and 10 μg/ml of Fraction 1 ((C), lower panel) on the whole blood clotting time to which thrombin (-■-), a PPACK clot (-⊟-) and clot-bound thrombin (-+-) is added.
Figure 36B:
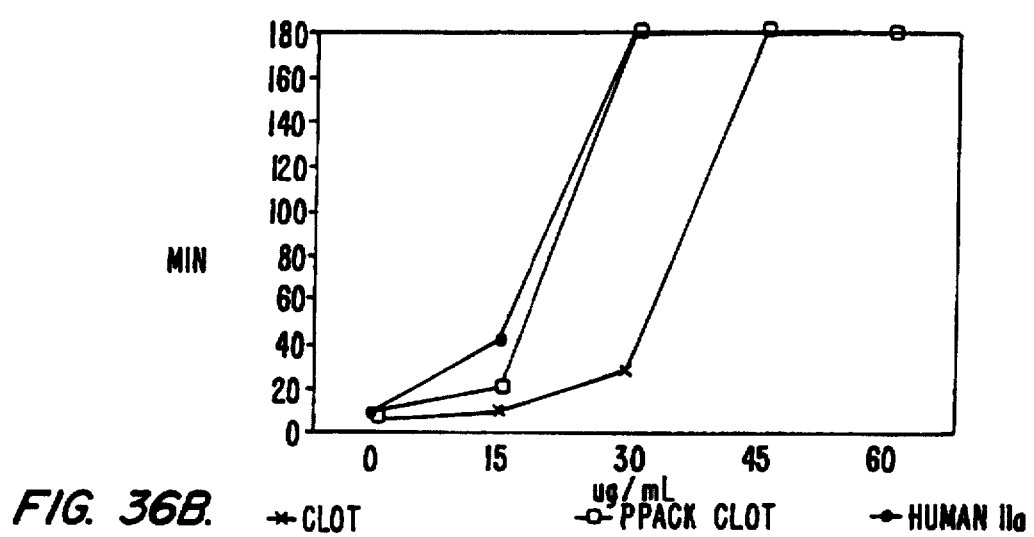
Figure 36C:
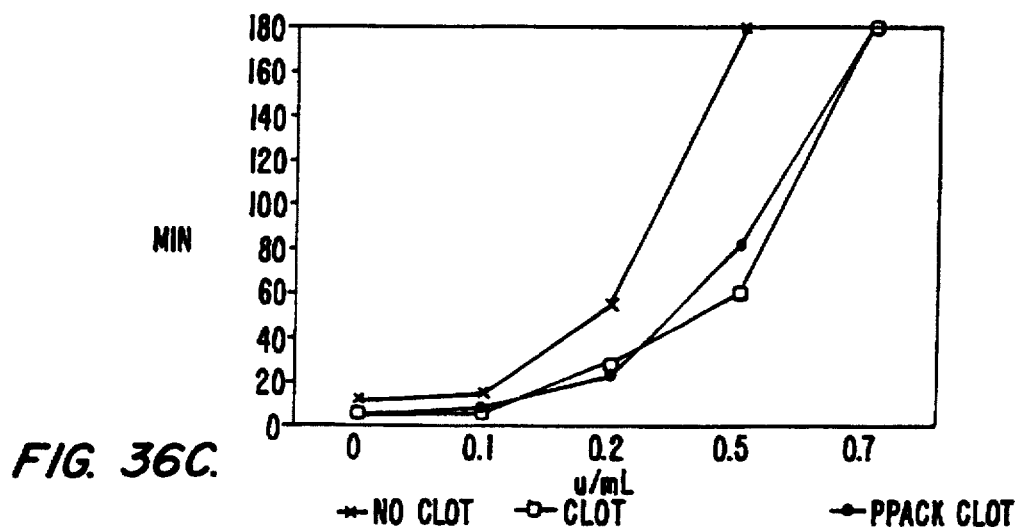

FIG. 36 compares the effects of heparin (FIG. 36A, upper panel), Fraction 1 (FIG. 36B, middle panel) and the combination of heparin and 10 μg/ml of Fraction 1 (FIG. 36C, lower panel) on the WBCT. The results for heparin and Fraction 1 have been described above and are set forth in FIG. 36 for purposes of comparison with the combination of heparin and Fraction 1. The IC 50 of the combination (FIG. 36C, lower panel) for the free thrombin was 0.3 units/ml (i.e., the same value as for heparin (FIG. 36A, upper panel). Similarly, the IC 50 for the PPACK clot is the same values as for heparin, i.e., about 0.55 units/ml. In contrast, the IC 50 for the clot-bound thrombin is the same as for the PPACK clot, i.e., about 0.55 units/ml. Thus, in contrast to heparin, the ratio for the relative sensitivity of this whole blood system to the effects of free thrombin (A) to clot-bound thrombin (C) is about 2.0, and the ratio for the relative sensitivity of the whole blood system to the effects of the PPACK-inactivated clot (B) to the clot-bound thrombin (A) is about 1.0.

Figure 37:
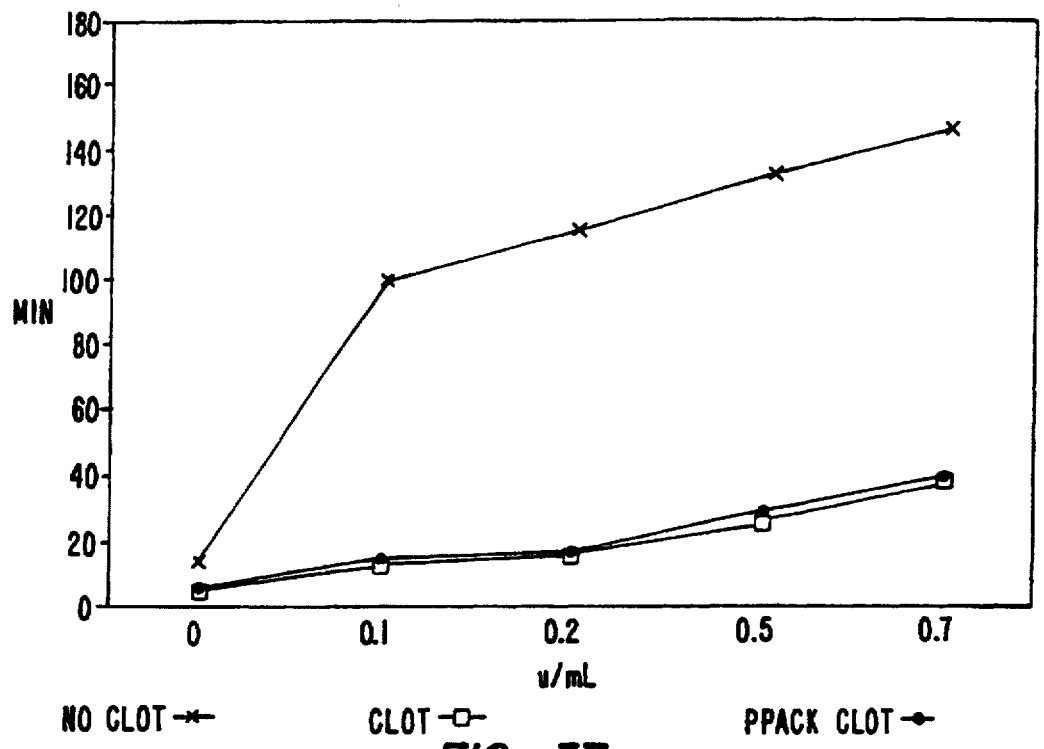
FIG. 37 illustrates the effect of increasing doses of a combination of standard heparin and dermatan sulfate (120 μg) on the whole blood clotting time to which thrombin (A) (-■-), a PPACK clot (B) (-⊟-) and clot-bound thrombin (C) (-+-) is added.
Figure 38:
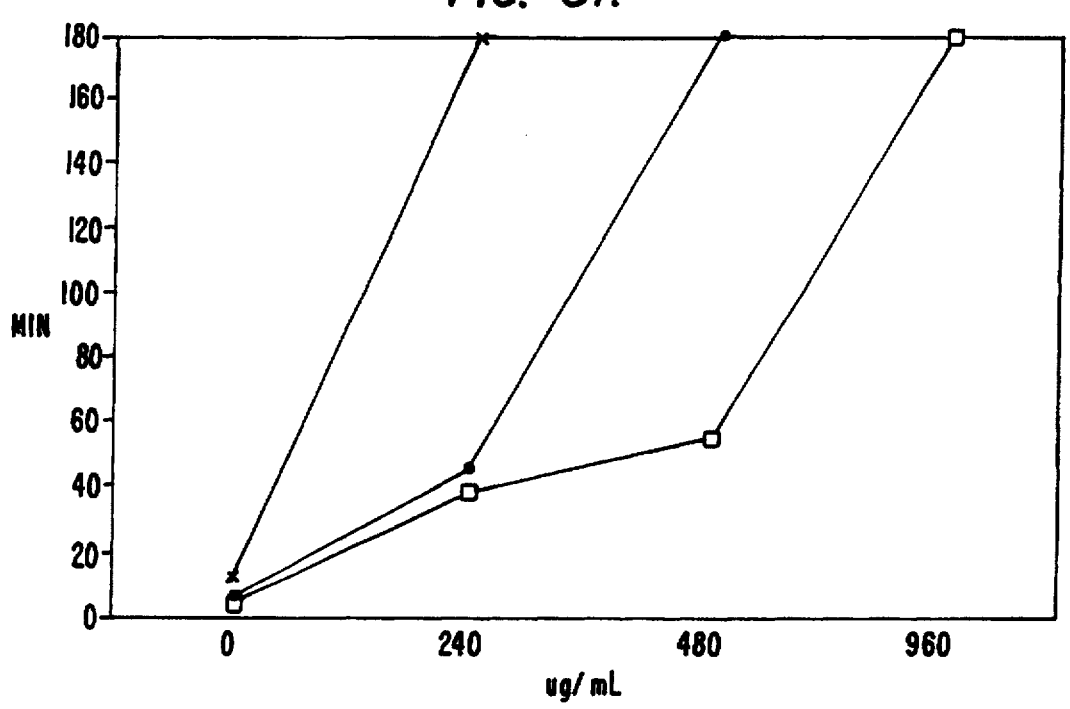
FIG. 38 illustrates the effect of increasing doses of a combination of dermatan sulfate and standard heparin (0.5 U/mL) on the whole blood clotting time to which thrombin (A) (-■-), a PPACK clot (B) (-⊟-) and clot-bound thrombin (C) (-+-) is added.

FIG. 37 illustrates the effect on the WBCT of the combination of heparin and DS. In contrast to V18, 120 μg/ml of DS did not influence the clotting time in the presence of the PPACK clot or the clot-bound thrombin. However, when increasing concentrations of DS were added to 0.5 units/ml of heparin (FIG. 38), it was possible to calculate a ratio for the relative IC 50 values. The ratio for the relative sensitivity of this whole blood system to the effects of free thrombin (A) to clot-bound thrombin (C) is about 5.0, and the ratio for the relative sensitivity of the whole blood system to the effects of the PPACK-inactivated clot (B) to the clot-bound thrombin (C) is about 2.0. Thus, the ratio for the relative sensitivity of this whole blood system to the effects of free thrombin (A) to clot-bound thrombin (C) is 1.1 and the ratio for the relative sensitivity of the whole blood system to the effects of the PPACK-inactivated clot to the clot-bound thrombin is about 1.0.

Figure 39:
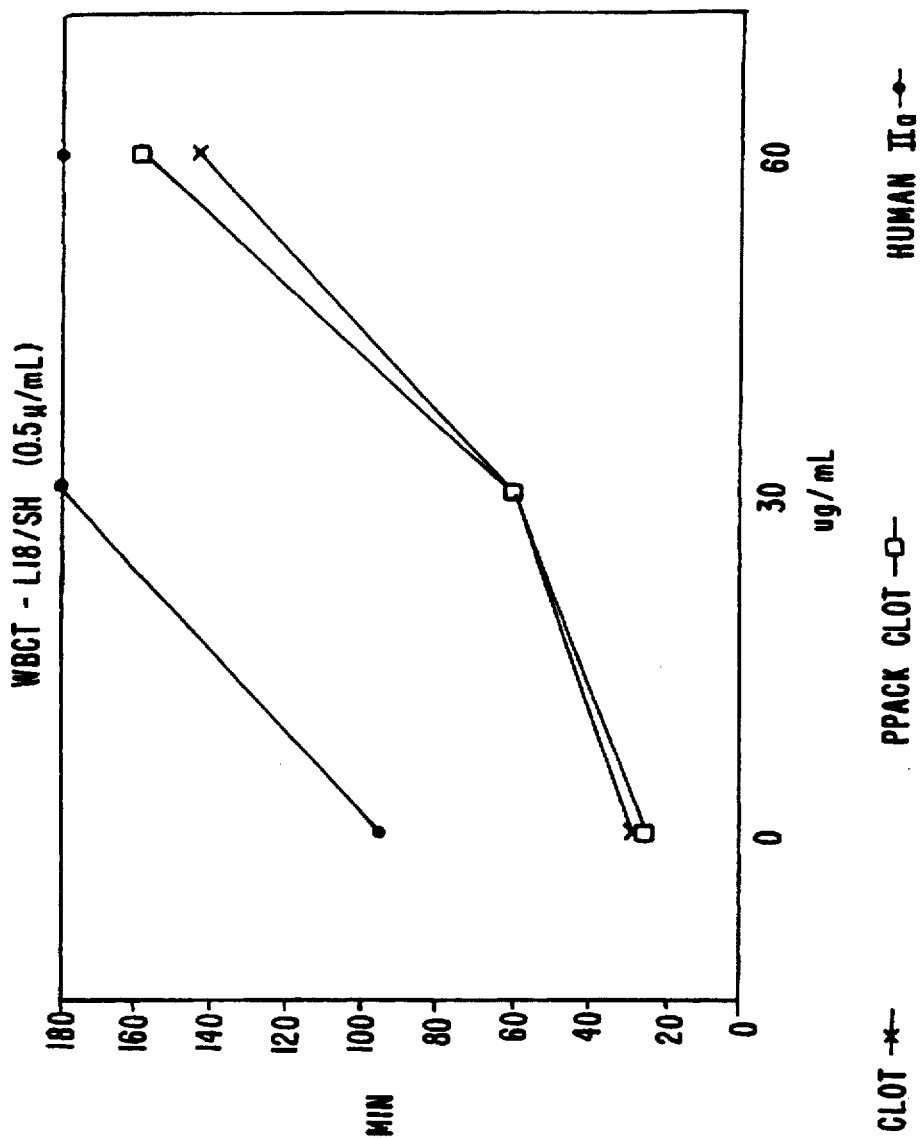
FIG. 39 illustrates the effect of increasing doses of a combination of V18 and standard heparin (SH) (0.5 U/mL) on the whole blood clotting time to which thrombin (A) (-■-), a PPACK clot (B) (-⊟-) and clot-bound thrombin (C) (-+-) is added.

FIG. 39 illustrates the effect on the WBCT of the combination of heparin and V18 on the whole blood clotting time to which thrombin (A), a PPACK clot (B) and clot-bound thrombin (C) is added. The IC 50 was 50 μg/ml, 45 μg/ml and 45 μg/ml for the free thrombin, the PPACK clot, and the clot-bound thrombin, respectively. Thus, the ratio for the relative sensitivity of this whole blood system to the effects of free thrombin (A) to clot-bound thrombin (C) is about 3, and the ratio for the relative sensitivity of the whole blood system to the effects of the PPACK-inactivated clot (B) to the clot-bound thrombin (C) is about 1.

A summary of the effects of the various GAGS on the WBCT in the presence of free thrombin, the PPACK clot and clot-bound thrombin and, in addition, the ratios of the corresponding IC 50 are set forth in Table 7.

TABLE 7

CONCENTRATIONS OF GAGS REQUIRED TO PROLONG THE WHOLE BLOOD CLOTTING TIME (IC50) IN THE ABSENCE AND PRESENCE OF A CLOT

| | Weight ug/ml | | |
|---|---|---|---|
| | Without clot | With clot | RATIO Clot/no clot |
| V18 | 90 | 150 | 1.5 |
| FRACT 1 | 45 | 45 | ~1.0 |
| FRACT 2 | 90 | 360 | 3.5 |
| FRACT 3 | 160 | 600 | 4.0 |
| SH | 2 | 6 | 3.0 |
| LMWH | 4 | 13 | 3.0 |
| DS | 480 | >1400 | >3.0 |

Moreover, a summary of the synergy between V18 and heparin against fibrin-bound thrombin is set forth in Table 8.

TABLE 8

SYNERGY BETWEEN V18 AND HEPARIN AGAINST FIBRIN-BOUND THROMBIN IN WHOLE BLOOD

| V18 ug/mL | Clotting Time |
|---|---|
| 0 | 6 |
| 60 | 14 |
| 120 | 20 |
| 240 | 75 |
| Heparin 0.5 U/mL | 30 |
| Heparin 0.5 U/mL plus V18 ug/mL 60 | 150 |

H. Clotting Prevention Studies Using A Bypass Circuit

Figure 40:
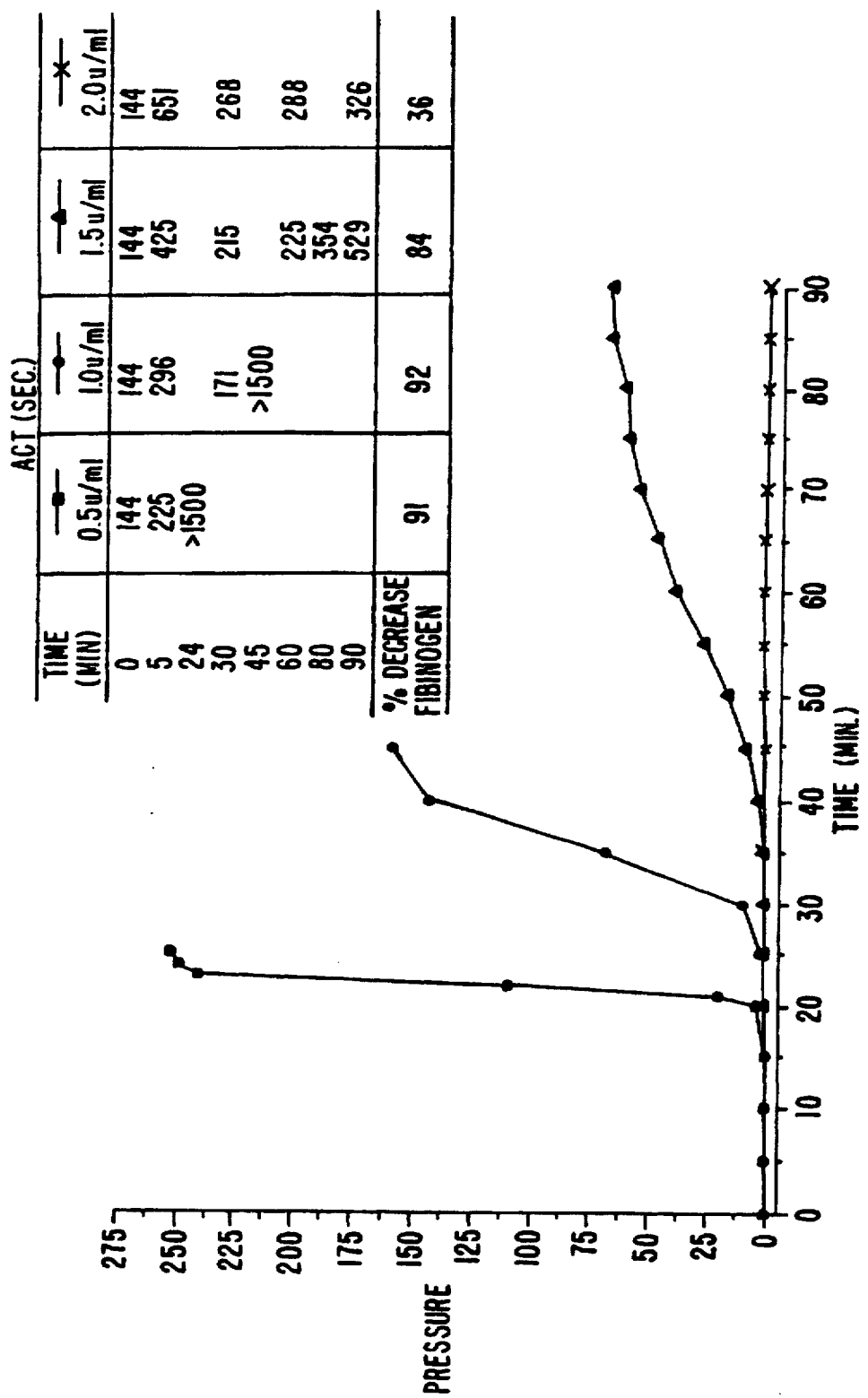
FIG. 40 illustrates the effect of heparin on preventing clotting in the bypass circuit.

FIG. 40 illustrates the effect of heparin on preventing clotting in the bypass circuit. Clotting occurred, with 84% fibrinogen consumption, at a heparin concentration of 1.5 units/ml. Clotting was partially prevented by a concentration of 2.0 units/ml, although there was still 36% fibrinogen consumption even at this concentration. V18 prevented clotting in the circuit at a concentration of 960 μg/ml when used alone and at a concentration of about 120 to 240 μg/ml when used in combination with 1.5 units/ml of heparin. Fraction 1 prevented clotting in the circuit at a concentration of about 120 μg/ml.

Figure 41:
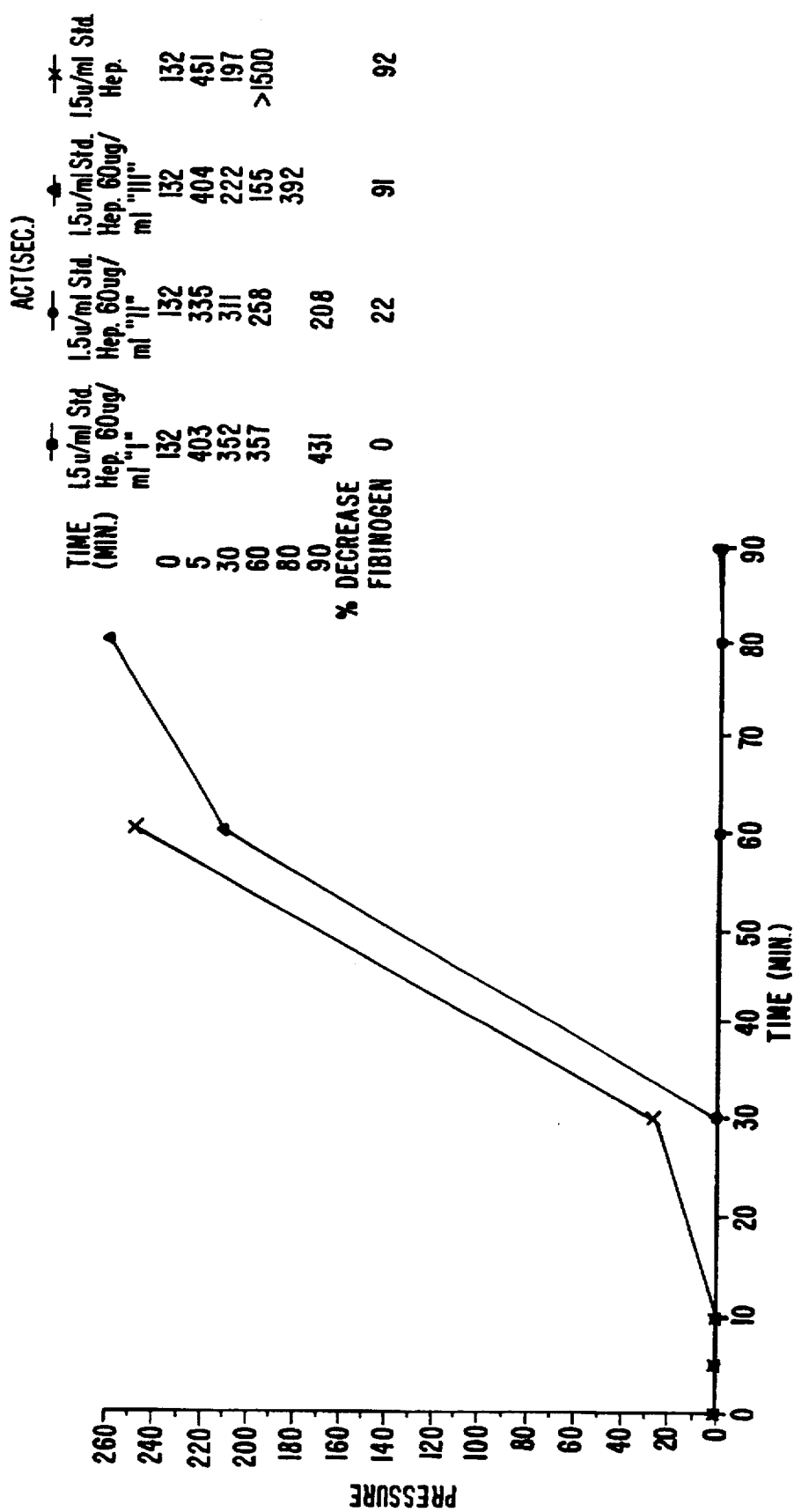
FIG. 41 compares the effectiveness of Fractions 1, 2 and 3 when combined with 1.5, units/ml of heparin in the bypass circuit FIG. 42 sets forth a summary of anti-Xa activity of inhibitors in a buffer system with and without ATIII present.
Figure 42:
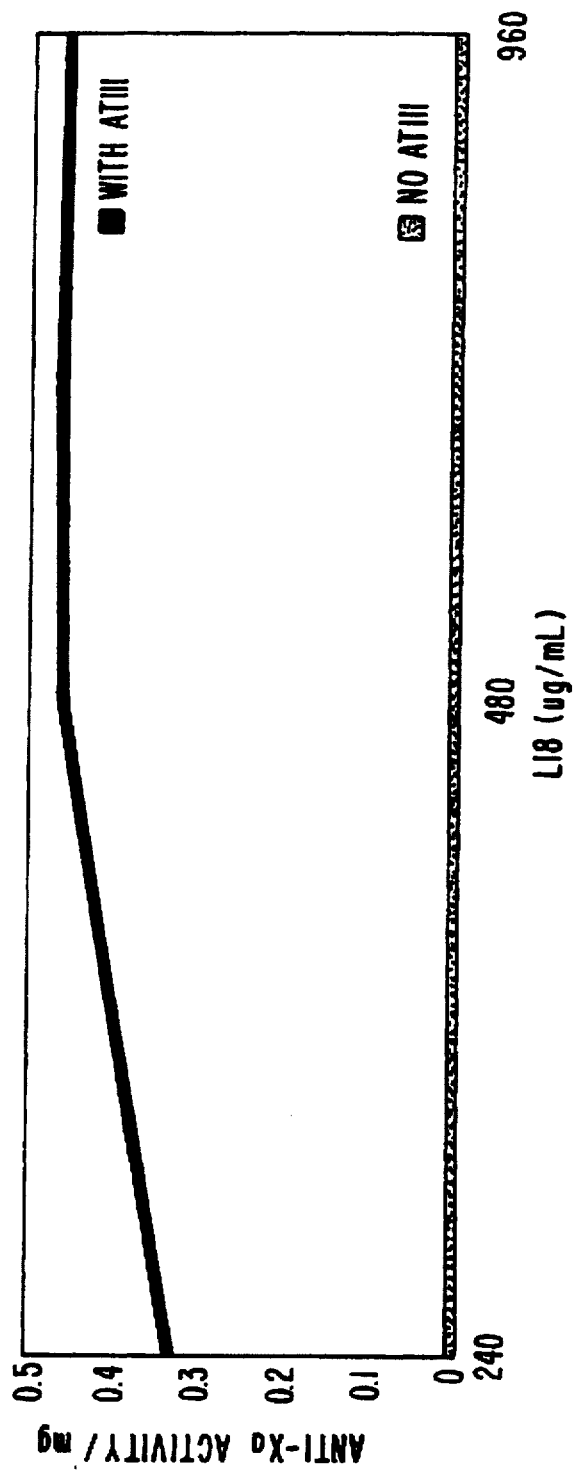

FIG. 41 illustrates the elution patterns of Fractions 1, 2 and 3 from a Sepharose G50 column. In addition, FIG. 42 compares the effectiveness of Fractions 1, 2 and 3 when combined with 1.5. units/ml of heparin. Fraction 1 prevented clotting in the circuit at a concentration of about 60 μg/ml, whereas Fraction 2 was partially effective at a concentration of about 60 μg/ml and Fraction 3 was ineffective. This experiment demonstrates that of the three fractions, Fraction 1 is most effective in the bypass circuit and Fraction 3 is the least effective. The minimum effective concentrations of the GAGS when used alone or, alternatively, in combination with 1.5 units/ml of heparin are set forth in Tables 9 and 10.

TABLE 9

COMBINATIONS EFFECTIVE IN CIRCUIT (MIN CONC)

| 1.5 U/mL | SH | + | 120 ug/mL | L18 |
| 1.5 U/mL | SH | + | 60 ug/mL | FRACT "1" |

TABLE 10

MINIMUM EFFECTIVE DOSE IN BYPASS CIRCUIT

| | Weight ug/mL |
|---|---|
| SH | 12 |
| LMWH | 80 |
| V18 | 960 |
| FRACT 1 | 240 |
| DS | >3840 |

The relative concentrations of the GAGS required to prolong the APTT and TCT, to prevent clotting of whole blood in the presence of a clot, and to prevent clotting in the bypass are shown in Table 11.

TABLE 11

CONCENTRATIONS OF GAGS REQUIRED TO PROLONG THE CLOTTING TIME

|  | TCT × 3 | APTT × 3 | Shunt | Thrombin | PPACK/ Clot | Clot |
|---|---|---|---|---|---|---|
| SH U/mL | 0.15 | 0.4 | 2.0 | 0.3 | 0.55 | 0.8 |
| LMWH U/mL | 0.25 | 0.7 | >8.0 | 0.4 | 0.9 | 1.2 |
| DS ug/mL | 15 | 150 | >3000 | 150 | >1440 | >1440 |
| V18 ug/mL | 160 | 120 | 960 | 70 | 150 | 200 |
| FRACT 1 ug/mL | 10 | 40 | 120 | 15 | 35 | 35 |
| FRACT 2 ug/mL | 150 | 110 |  | 65 | 150 | 150 |
| FRACT 3 ug/mL | >600 | 240 |  | 120 | 250 | 500 |

The IC 50 for the TCT and corresponding doses required to prevent clotting in the circuit and the relative ratios are shown in Table 12.

TABLE 12

COMPARISON OF IC50 FOR TCT AND EFFECTIVE DOSE IN BYPASS

|  | IC50 ug/mL | Bypass ug/mL Alone | Ratio | With Hep 1.5 U/mL |
|---|---|---|---|---|
| DS | 40 | >3840 | >100 |  |
| V18 | 260 | 960 | 3.7 | 120 |
| FRACT 1 | 45 | 240 | 5.3 | 60 |
| SH | 0.6 | 14 | 23 |  |
| LMWH | 2.5 | 80 | 32 |  |

I. Measurement Of Second Order Rate Constants

A summary of the fold increase in second order rate constants (K2) for ATIII-mediated catalysis of factor Xa and thrombin inhibition, and HCII-mediated thrombin inhibition at concentrations of 6, 60, and 300 μg/ml are shown in Table 13.

TABLE 13

FOLD INCREASE OF $K_2$

| GAG | Conc. ug/mL | ATIII Xa | ATIII IIa | HCII IIa |
|---|---|---|---|---|
| SH | 6 | 750 | 577 | 46 |
|  | 60 | 2165 | 2545 | 746 |
|  | 300 | 3075 | 188 | 576 |
| LMWH | 6 | 262 | 357 | 26 |
|  | 60 | 485 | 213 | 38 |
|  | 300 | 1557 | 190 | 98 |
| V18 | 6 | 19 | 100 | 300 |
|  | 60 | 68 | 61 | 600 |
|  | 300 | 260 | 61 | 600 |
| DS | [??] 6 | — | 2 | 120 |
|  | 60 | — | 10 | 1161 |
|  | 300 | — | 22 | 2120 |

The fold increase in K2 at therapeutic concentrations of these GAGS is shown in Table 14.

TABLE 14

FOLD INCREASE OF $K_2$ OF GAGS

|  | ATIII Xa | ATIII IIa | HCII IIa |
|---|---|---|---|
| SH | 750 | 577 | 46 |
| LMWH | 262 | 357 | 26 |
| DS | — | 3 | 2100 |
| V18 | 68 | 61 | 600 |
| SS-LMWH | 583 | 250 | 1200 |

At therapeutic concentrations (i.e., about 6 μg/ml), heparin (SH) and LMWH produce their anticoagulant effects by activating ATIII, with only a weak contribution from catalysis of HCII. In contrast, at therapeutic concentrations (about 60 to 300 μg/ml), V18 produces its anticoagulant effect by activating both ATIII and HCII. Moreover, at therapeutic concentrations (about 300 μg/ml), DS produces its anticoagulant effect by activating HCII. It is interesting to note that in both assays in which clotting is mediated by fibrin-bound thrombin (i.e., the whole blood clotting time with plasma clot and the bypass circuit), much higher concentrations of DS than V18 are required to prevent less clotting, yet V18 has almost 50-fold less rate enhancement on HCII-mediated thrombin inhibition. The binding affinities (Kd) of the various GAGS for thrombin (IIa), factor Xa, and ATIII are shown in Table 15

TABLE 15

INTRINSIC MEASUREMENTS OF GAGs BINDING TO SERINE PROTEASES AND THEIR INHIBITORS

| GAG | Kd nM IIa | HCII | ATIII | Xa |
|---|---|---|---|---|
| StHp | 116.6 |  | 24.7 |  |
| V18 | 1048.9 |  | 27311 |  |
| DS | 2601.4 |  | — |  |
| LMWH | 940.4 |  | 208.5 |  |

J. Experiments To Determine Whether V18 has Anticoagulation Effects Which Are Independent Of HCII Or ATIII Experiments were performed to determine whether V18 had effects on coagulation which were independent of ATIII or HCII. These experiments were designed to determine: 1) if V18 inhibited factor Xa independently of ATIII; 2) if V18 impaired fibrin polymerization; 3) if V18 inactivated factors IXa or XIa independently of ATIII; and 4) if V18 is as effective in a platelet-rich system as in a platelet-poor system.

1. ATIII-independent inhibition of factor Xa

Figure 43A:
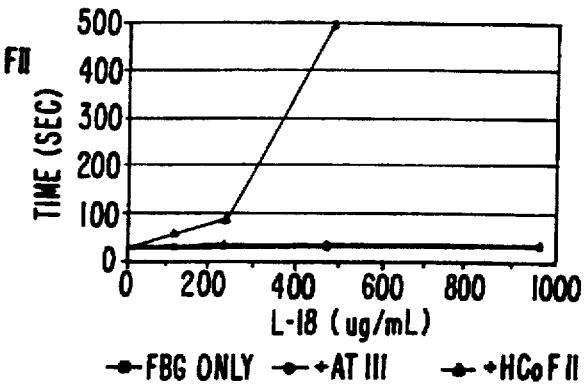
FIG. 43 illustrates the prolongation of the thrombin clotting time in a buffer system containing fibrinogen measured in the presence and absence of ATIII or HCII for various GAGs.
Figure 43B:
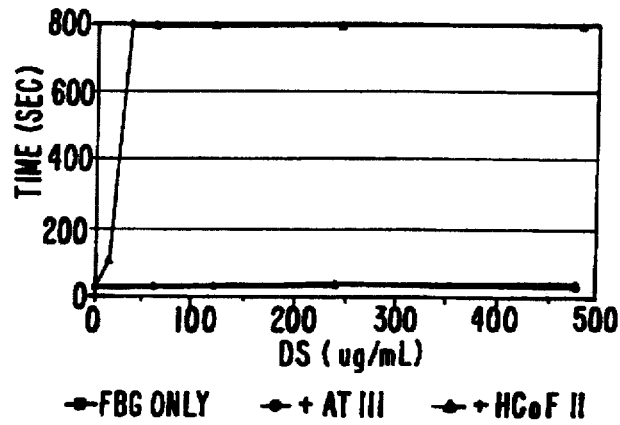
Figure 43C:
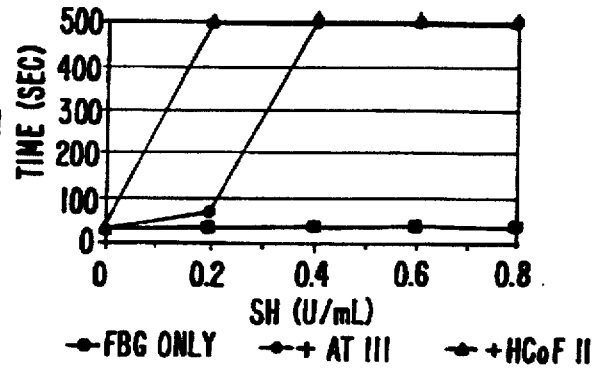
Figure 44A:
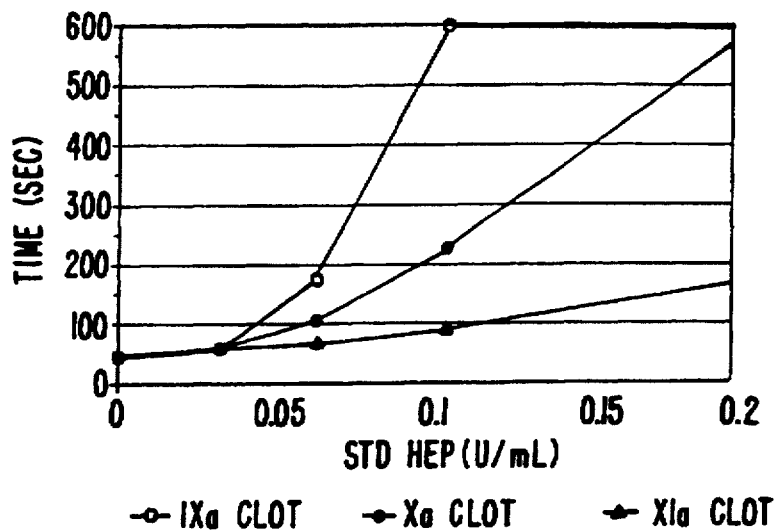
FIG. 44 illustrates the relative effects of standard heparin (A), LMWH (B), V18 (C) and Fraction 1 of V18 (C) on inactivating Xa, IXa and XIa in a plasma system to which each of these coagulation enzymes was added.
Figure 44B:
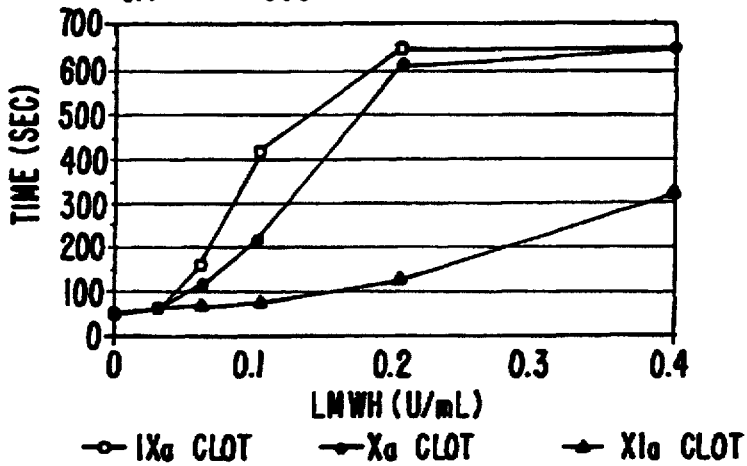
Figure 44C:
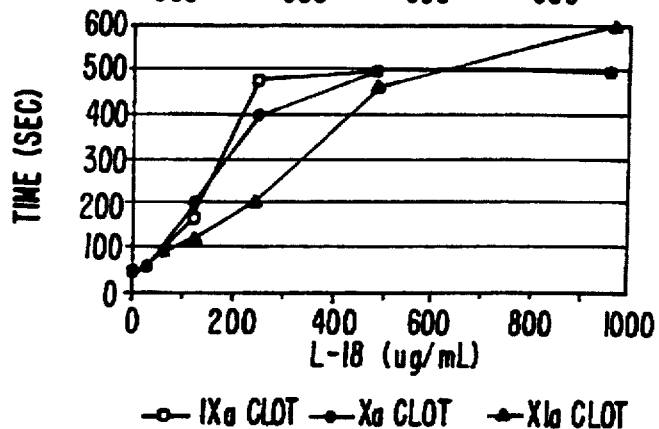
Figure 44D:
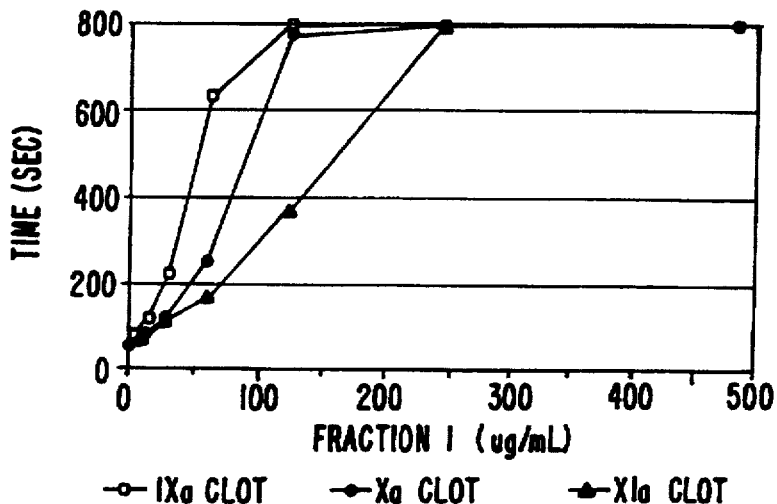

In a buffer system, the anti-factor Xa activity of V18 was measured in the presence and absence of ATIII. V18 did not inactivate factor Xa in the absence of ATIII (FIG. 43).

2. Inhibition of fibrin polymerization

To determine whether V18 was interfering with fibrin polymerization, the prolongation of the thrombin clotting time in a buffer system containing fibrinogen was measured in the presence and absence of ATIII or HCII. For comparison, experiments were performed with heparin (SH) and DS. None of these GAGS prolonged the thrombin clotting time in the absence of ATIII or HCII. The effect of V18 was HCII-dependent as was the effect of DS. On a weight basis, DS was about 20-fold more potent than V18. In contrast to V18 and DS which required HCII and not ATIII to inhibit fibrinogen clotting by thrombin. heparin acted through both co-factors, although ATIII was a more effective co-factor (FIG. 44).

3. Inactivation of IXa and XIa

These experiments were performed to determine whether V18 or Fraction 1 of V18 prolonged the APTT by inactivating IXa or XIa by mechanisms independent of ATIII or HCII. The relative effects of heparin, LMWH, V18 and Fraction 1 of V18 on inactivating Xa, IXa and XIa was studied in a plasma system to which each of these coagulation enzymes was added (FIG. 44). Each of the coagulation enzymes was added in a concentration which produced a clotting time of between 40 and 50 seconds. Heparin (FIG. 44A) prolonged the IXa clotting time more than the Xa clotting time and had relatively less effects on the XIa clotting time. In contrast, all of the other GAGS, including V18 and Fraction 1 of V18, had similar effects on the IXa and Xa clotting times. These results indicate that V18 (FIG. 44C) and Fraction 1 of V18 (FIG. 44D) do not have effects on IXa or XIa which are independent of ATIII or HCII.

K. Effect Of Platelets On The Anticoagulant Activity of V18 and Fraction 1

Figure 46:
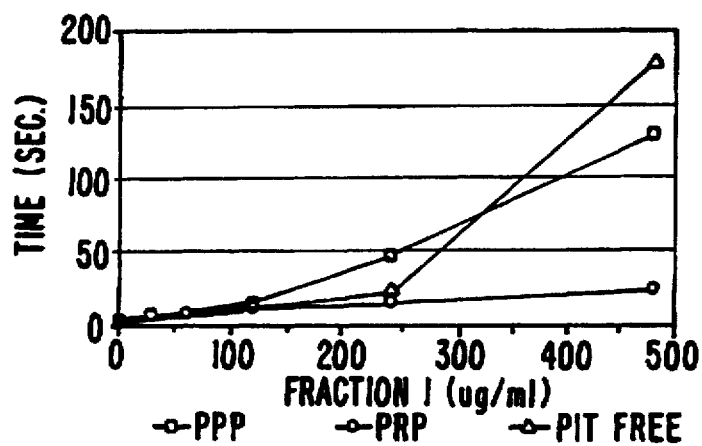
FIG. 46 illustrates the results of the recalcification times using various GAGS in platelet-rich plasma (PRP), platelet-poor plasma (PPP) and platelet-free plasma (Pit-Free).

The factor Xa clotting time was performed on plateletrich, platelet-poor and platelet-free plasma in the presence of heparin, V18, LMWH and Fraction 1 of V18. In all cases, the clotting time was shorter in platelet-rich plasma, indicating that factor Xa is protected from inactivation by these GAGS, including V18 and Fraction 1 (FIG. 45). However, the anticoagulant effects of V18 appear to be more resistant to platelets than heparin or LMWH. The results of the recalcification times with all of these GAGS was much shorter in platelet-rich than platelet-poor plasma, indicating that factor IXa in the tenase complex is protected from inactivation by these GAGS (FIG. 46).

1. V18 has Anticoagulation Effects Which Are Independent Of HCII Or ATIII

Although V18 has minimal Anti-factor Xa activity when tested in-vitro in a standard chromogenic factor Xa assay, it has appreciable anticoagulant activity when tested in HCII-depleted plasma. This is summarized in Table 16 which describes the effect of V18 and heparin on the recalcification clotting time (clotting of citrated platelet-depleted plasma by the addition of calcium and phospholipid [cephalin]). In normal plasma, V18 in a concentration of 500 µg/ml increased the recalcification time 9.6-fold. The addition of this concentration of V18 increased the recalcification time 3.6 fold in ATIII-depleted plasma (the "HCII effect") and 4.1 fold in HCII-depleted plasma (the "ATIII effect"). In addition V18 increased the recalcification time 2.9 fold in plasma depleted of both HCII and ATIII (double depleted plasma). In contrast, the effect of heparin in prolonging the recalcification time was virtually entirely ATIII-dependent. Thus, the fold increase in recalcification time with heparin was only 9.5 in normal plasma, 1.2 in ATIII-depleted plasma (the "HCII effect") 6.0 in the HCII-depleted plasma (the ATIII effect) and 1.3 in plasma depleted of both HCII and ATIII. These finding indicate that the anticoagulant effect of V18 is contributed to by both an HCII- and ATIII-mediated mechanism, and by a mechanism which is independent of both ATIII and HCII. In contrast, almost all of the anticoagulant effect of heparin is mediated by ATIII.

Figure 47:
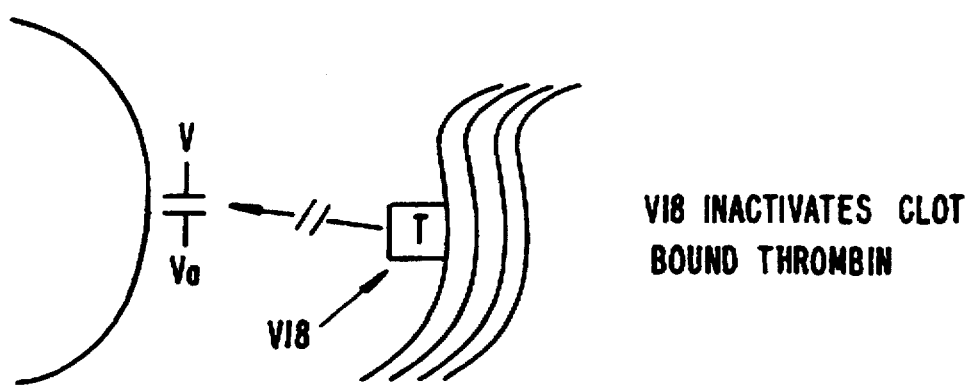
FIG. 47 illustrates the mechanism of impaired assembly.

Without intending to be restricted to a particular theory, it is thought that two interrelated mechanisms are responsible for the HCII-independent activity of V18. Both are related to the fact that V18 interferes with the assembly of factor Xa on the platelet surface. The process of blood coagulation occurs on the platelet surface as a result of the assembly of a number of the coagulation factors on the surface. Thus factor IXa complexes with factor VIIIa to form the tenace complex which activates factor X to factor Xa, and factor Xa in turn forms a complex with factor Va on the platelet surface (the "prothrombinase complex") which converts prothrombin to thrombin. Factor Va is the receptor for Factor Xa on the platelet surface. The activation of Factor V to Factor Va is mediated by thrombin surface. In the thrombus, which consists of platelet aggregates in a fibrin meshwork, the activation of factor V is mediated by thrombin which is bound to fibrin in close proximity to platelets (FIG. 47). Factor Xa is protected from inactivation by its natural inhibitor, ATIII when this clotting enzyme is bound to factor Va on the platelet surface (FIG. 48). Therefore, agents that prevent factor Xa binding to the platelet surface markedly enhance the rate activation of factor Xa by ATIII (FIG. 49).

V18 interferes with the binding of factor Xa to the platelet surface by two different but interacting mechanisms (FIG. 50). First, by inactivating fibrin-bound thrombin through an HCII-mediated mechanism, V18 impairs the activation of factor V to factor Va, thereby reducing the density of the factor Xa receptor on the platelet surface. Second, as shown, V18 competes with Factor Xa binding to a phospholipid surface ("platelet" surface). Both of these mechanisms act to inhibit the binding of factor Xa to the platelet surface, thereby rendering the factor Xa vulnerable to inactivation by even a relatively weak ATIII catalyst such as V18 (FIG. 49).

The interference with assembly exhibited by V18 is novel. The process not only targets Xa, but as shown in FIG. 49, other clotting enzymes. Other discoveries have attempted to compete with binding of Xa and IXa, by using inactive protein analogues. However, the antithrombotic mechanism described above for V18 is unique because it combines an HCII activator with selectivity to fibrin-bound thrombin with a unique process for interfering with assembly of factor Xa on the platelet surface which exposes the unprotected factor Xa to inactivation by ATIII. By combining the HCII-mediated inactivation of fibrin-bound thrombin with an ATIII mediated inhibition of thrombin generation (through inactivation of factor Xa), V18 modulates thrombogenesis by inhibiting two critical pathways (FIG. 50).

TABLE 16

| | Normal Plasma | ATIII Dep Plasma | HCII Dep Plasma | Double Dep Plasma |
|---|---|---|---|---|
| | Time in Minutes | | | |
| CONTROL | | | | |
| 1/5 Cephalin | 3.3 | 2.3 | 2.3 | 2.3 |
| | RATIOS | | | |
| V18 200 ug/mL | | | | |
| 1/5 Cephalin | 2.8 | 1.8 | 2.0 | 1.5 |
| V18 300 ug/mL | | | | |
| 1/5 Cephalin | 4.6 | 2.3 | 2.8 | 2.3 |
| V18 500 ug/mL | | | | |
| 1/5 Cephalin | 9.6 | 3.6 | 4.1 | 2.9 |
| Heparin 0.5 U/mL | | | | |
| 1/5 Cephalin | 9.5 | 1.2 | 6 | 1.3 |

M. Comparison of V18 (MW 3,000 to 8,000) and SPL (MW 1,000 to 3,000) In A Simulated Cardiopulmonary Bypass Circuit This example compares the activity of V18 with SPL, a V18-like material having a molecular weight of 1,000 to 3,000 Da, in a simulated cardiopulmonary bypass circuit. As set forth in Table 17, infra, in contrast to V18, SPL is substantially inactive.

1. Preparation of SPL, a V18-like Material Having a Molecular Weight of 1,000 to 3,000 Daltons 2 g of SPL (1,000 to 3,000 Da) product was dissolved in 50 mL of distilled water. An equal volume of 0.2M sodium metaperiodate (freshly made) was added. The solution was mixed and kept at 4° C. for 24 h. 5.0 mL of ethylene glycol was added and the solution was placed in dialysis tubing (MWCO 500) and dialyzed against several changes of distilled water for 24 h. The solution was put back into a beaker and 800 mg of potassium borohydride was added with constant stirring. The solution was kept in the dark for 2.5 h at room temperature. The pH was adjusted to 3.0 with 1N HCl and quickly readjusted to pH 7.4 with 1N NaOH. The solution was dialyzed again as previously describe and the lyophilized to yield the final product.

2. Comparison of V18 and SPL in the Simulated Cardiopulmonary Bypass Circuit

A comparison of V18 and SPL was carried in the simulated cardiopulmonary bypass circuit described above. The results obtained establish that in contrast to V18, SPL is substantially inactive (See, Table 17, infra). It is for this reason that the fraction of the heparin molecules having molecular weights below 3,000 Da are removed from V18. By removing such molecules from V18, the potency of V18 is substantially increased.

TABLE 17

| TREATMENT µg/mL | A.C.T. secs | TIME TO CIRCUIT FAILURE (min) | FIBRINOG CONSUMPT |
|---|---|---|---|
| V18 | 480 | 372 | >90 | 9 |
| V18 | 240 | 284 | >90 | 9 |
| SPL (1,000–3000) | 480 | 193 | 17 | 89 |

N. Comparison of The Efficacy and Safety of Hirudin with the Combination of V18 and Heparin In a Simulated Cardiopulmonary Bypass Circuit This example compares the efficacy and safety of hirudin with the combination of V18 and heparin in the simulated cardiopulmonary bypass circuit described above. The results obtained clearly establish that in contrast to hirudin, V18 has very good APTT's at concentrations having no bleeding problems (See, Table 18).

TABLE 18

| Treatment | ACT (secs) | Time to Treatment Failure (min) | Fibrin Deposited % |
|---|---|---|---|
| Hirudin | 340 | 30 | >90 |
| Hirudin | 480 | 60 | >90 |
| Hirudin | 610 | 75 | >90 |
| Hirudin | >1500 | >90 | 9 |
| V18 | 358 | >90 | 8 |
| V18 and heparin | 370 | >90 | 6 |
| Heparin | 360 | 35 | 91 |
| SALINE | 180 | 10 | >90 |

O. Comparative Effects Of V18+Desmin On Fluid Phase Thrombin And Clot-Bound Thrombin This example compares the effects of V18 and desmin, i.e., low molecular weight dermatan sulfate, on fluid phase thrombin and clot-bound thrombin using the previously described Hanging-Clot Assay. The results set forth in Table 19, infra, unequivocally establish that desmin is less-selective than V18 and, in addition, less potent than V18 by a factor of about 4.

TABLE 19

| | Fluid-Phase Thrombin | Clot-bound Thrombin Human Bypass Circuit |
|---|---|---|
| | TCT (IC 50) | (IC 50) |
| V18 ug/mL | 90 | 210 |
| Desmin ug/mL | 15 | 750 |
| RATIO V18 Desmin | 6:1 | 1:3.5 |

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purpose.

What is claimed is:

1. A heparin cofactor II-specific (HCII-specific) catalytic agent that inactivates clot-bound thrombin, having:

(i) a heparin cofactor II specific activity against heparin cofactor II of about 2 to about 5 units/mg in an anti-factor IIa assay;

(ii) an antithrombin III (ATIII) specific activity against factor Xa of about 0.2 to about 1.5 units/mg in an anti-factor Xa assay; and (iii) a solubility in aqueous media ranging from about 150 to about 1,000 mg/ml;

wherein:

said HCII-specific catalytic agent is a polyanionic carbohydrate having about 10 to about 24 monosaccharide units.

2. An agent of claim 1, wherein said agent has an antithrombin III affinity of less than about 3% of that of unfractionated heparin.

3. An agent of claim 1, wherein said polyanionic carbohydrate is a heparin preparation having a molecular weight of between about 3,000 and about 8,000 Daltons.

4. An agent of claim 3, wherein the heparin preparation:

(i) consists essentially of the lowest third molecular weight fraction isolated from unfractionated heparin; or (ii) is produced from unfractionated heparin by chemically lowering the molecular weight range to between about 3,000 and about 8,000 Daltons.

5. An agent of claim 3, wherein the heparin preparation:

(i) has an average molecular weight of about 8,000 Daltons;

(ii) has an average molecular weight of about 5,000 Daltons; or (iii) has an average molecular weight of about 3,000 Daltons.

6. An agent of claim 3, wherein the heparin preparation is produced from unfractionated heparin by chemically lowering the molecular weight range of between about 3,000 and about 8,000 Daltons and had its antithrombin activity reduced by treating the vicinal alcohol groups present in the heparin preparation with an oxidizing agent followed by a reducing agent and optionally wherein the oxidizing agent is selected from sodium periodate, dimethyl sulfoxide, acid anhydrides, lead tetraacetate and ascorbic acid, and the reducing agent is selected from sodium borohydride, lithium aluminum hydride, metal hydrides and hydrazine.

7. An agent of claim 3, wherein the heparin preparation consists essentially of material without affinity for ATIII, said material having been prepared by affinity purification on a solid phase to which ATIII is immobilized and the effluent retained.

8. An agent of claim 1, which has the formula (a):

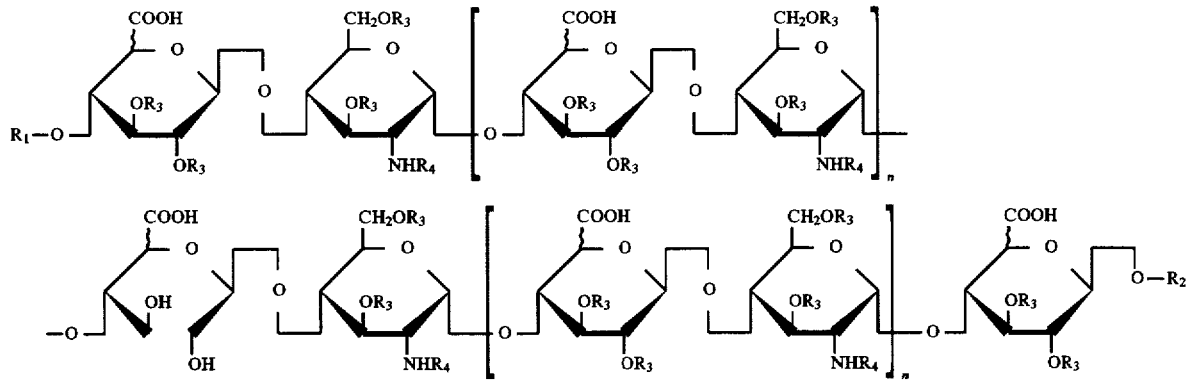

in which:

$R_1$ is a member selected from the group consisting of H, D-glucosamine acid residue, D-glucuronic acid residue and L-iduronic acid residue;

$R_2$ are members independently selected from the group consisting of H, D-glucosamine acid residue, D-glucuronic acid residue, L-iduronic acid residue, and anhydromannitol;

$R_3$ is a member selected from the group consisting of H and $SO_3^-$; and $R_4$ is a member selected from the group consisting of H, $SO_3^-$ and $CH_3CO^-$;

the n indexes are independently selected and can have values ranging from 0 to about 14;

wherein:

the HCII-specific catalytic agent has a molecular weight ranging from about 3,000 Daltons to about 8,000 Daltons; or (b) the formula:

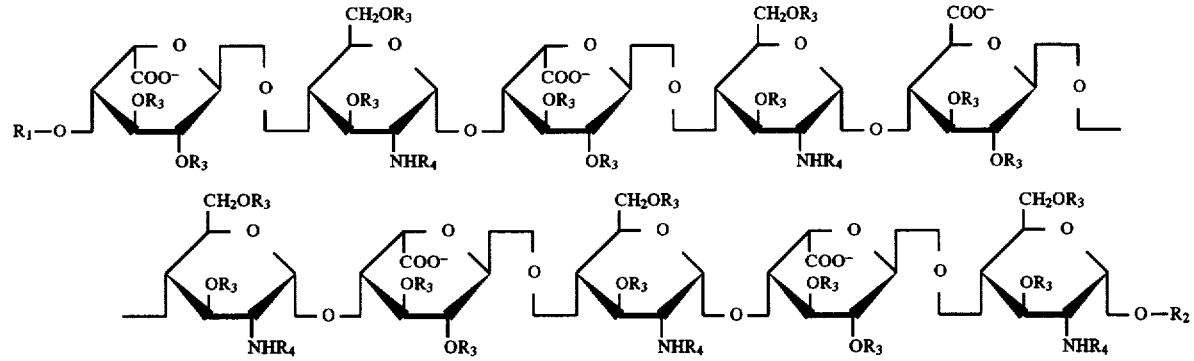

in which:

$R_1$ and $R_2$ are members independently selected from the group consisting of H, D-glucosamine acid residue, D-glucuronic acid residue and L-iduronic acid residue;

$R_3$ is a member selected from the group consisting of H and $SO_3^-$; and $R_4$ is a member selected from the group consisting of H, $SO_3^-$ and $CH_3CO^-$;

wherein:

the HCII-specific catalytic agent has a molecular weight ranging from about 3,000 Daltons to about 8,000 Daltons.

9. An agent of claim 1, having one or both of the following features: (i) a heparin cofactor II specific activity of about 3 to 4 units/mg in anti-factor IIa activity; (ii) an ATIII specific activity of about 1 unit/mg in an anti-factor Xa assay.

10. An agent of claim 1, wherein:

(i) the agent is combined with a heparin additive, or (ii) the agent is combined with a heparin additive and the weight ratio of the HCII-specific catalytic agent to the heparin additive is greater than about 2 to 1, wherein optionally the heparin additive is unfractionated heparin or is the lowest third molecular weight fraction isolated from unfractionated heparin.

11. A pharmaceutical composition for inhibiting thrombogenesis in a patient, the composition comprising:

(i) from about 90 to about 99.9 weight percent of an HCII-specific catalytic agent that inactivates fibrin-bound thrombin, the HCII-specific catalytic agent having only low affinity for antithrombin III (ATIII);

(ii) from about 0.1 to about 10 weight percent of an ATIII catalytic agent that inactivates fluid phase thrombin, wherein;
said HCII-specific catalytic agent is a polyanionic carbohydrate having about 10 to about 24 monosaccharide units and the HCII catalytic activity of said composition is about 2 to about 5 units/mg.

12. A composition of claim 11, wherein the polyanionic carbohydrate is a heparin preparation having a molecular weight of between about 3,000 and about 8,000 Daltons.

13. A composition of claim 12, wherein the ATIII catalytic agent is unfractionated heparin, or is the lowest third molecular weight fraction isolated from unfractionated heparin.

14. A product comprising:
(i) an agent that inactivates clot-bound thrombin, wherein said agent is a polyanionic carbohydrate of about 10 to about 24 monosaccharide units and having low affinity for antithrombin III (ATIII) and a heparin cofactor II specific activity against heparin cofactor II of about 2 to about 5 units/mg in an anti-factor IIa assay; and
(ii) an ATIII catalytic agent that inactivates fluid-phase thrombin as a preparation for simultaneous, separate or sequential use for inhibiting clot-bound thrombin and fluid-phase thrombin in a patient.

15. A product of claim 14, wherein the thrombin inactivator agent is
(i) an HCII-specific catalytic agent as defined in one or more of claims 1 to 8, or
(ii) a polyanionic carbohydrate as defined by the specific features recited in claim 12(i) or (ii), and additionally or alternatively has a heparin cofactor II specific activity of about 3 to about 4 units/mg in anti-factor IIa activity.

16. A product of claim 14, wherein the ATIII catalytic agent is unfractionated heparin, or is the lowest third molecular weight fraction isolated from unfractionated heparin.

17. A low molecular weight heparin preparation having:
(i) a molecular weight or between about 3,000 and about 8,000 Daltons (±1,000);
(ii) a heparin cofactor II specific activity against heparin cofactor II of about 2 to about 5 units/mg in an anti-factor IIa assay;
(iii) an antithrombin III (ATIII) specific activity against factor Xa of about 0.2 to about 1.5 units/mg in an anti-factor Xa assay;
(iv) a solubility in aqueous media ranging from about 150 to about 1,000 mg/ml; and
(v) a uronic acid residue or other native, non-reducing sugar as one end group and a 2,5-anhydromannitol non-reducing sugar as the other end group;
wherein:
said low molecular weight heparin preparation is a polyanionic carbohydrate having about 10 to about 24 monosaccharide units.

18. A polyanionic carbohydrate capable of selectively inactivating clot-bound thrombin in favor of free thrombin, that is obtained from heparin, having its non-sulfated uronic acid residues in open-ring form, and substantially free of aldehyde groups.

19. A carbohydrate of claim 18, which has a native, nonreducing sugar as one end group and a 2,5-anhydromannitol non-reducing sugar as the other end group, and/or where about 30% of the uronic acid residues are in open-ring form.

20. A product capable of selectively inhibiting clot-bound thrombin prepared by:
(i) depolymerizing unfractionated heparin using nitrous acid;
(ii) isolating and pooling the depolymerized fractions having molecular weights ranging from 3,000 (±1000) to 8,000 (±1,000) to provide a low molecular weight fraction;
(iii) cleaving the low molecular weight fraction using periodate;
(iv) reducing the cleaved fraction using sodium borohydride, wherein optionally an antithrombin III (ATIII) affinity column is used to obtain depolymerized heparin having a reduced affinity for ATIII, and the low molecular weight fraction has a specific activity of about 2 to about 5 antithrombin units/mg and less than about 1.5 antifactor Xa units/mg;
wherein:
said product is a polyanionic carbohydrate of about 10 to about 24 monosaccharide units.

21. A product produced by:
(i) depolymerizing standard unfractionated heparin by nitrous acid depolymerization;
(ii) oxidizing the depolymerized heparin with sodium periodate in an aqueous medium for 24 hour at 4° C., and stopping the oxidation reaction by the addition of excess ethylene glycol followed by dialysis against distilled water using dialysis tubing with a 500 MW cut off;
(iii) reducing the oxidized product by the addition of sodium borohydride and, after allowing the reaction mixture to stand for 25 hours at 23° C., adjusting the pH of the reaction mixture to 3.0 with HCl to destroy excess borohydride then increasing the pH to 7.0 by the addition of NaOH;
(iv) dialyzing the resultant product against distilled water; and
(v) recovering the product by lyophilization; and optionally
(vi) passing the product over an anti-thrombin III affinity column, the product obtained having the following properties;
molecular weight of from 3,000 (±1,000) to 8,000 (±1,000)
specific activity of about 2 to about 5 anti-Factor IIa units/mg
specific activity of less than about 1.5 antiThrombin IIa units/mg.

22. A pharmaceutical product comprising as active agent a catalytic agent of claim 1 and a pharmaceutically acceptable excipient, diluent or carrier, the pharmaceutical product optionally further comprising an inhibitor of fluid phase thrombin for simultaneous, separate or sequential administration with said active agent.

23. A method for inhibiting thrombus formation in a patient without inducing a clinically unsafe increase in systemic bleeding, said method comprising the step of administering to the patient a pharmacologically acceptable dose of a heparin cofactor II-specific (HCII-specific) catalytic agent that inactivates clot-bound thrombin, said HCII catalytic agent having:
(i) a heparin cofactor II specific activity against heparin cofactor II of about 2 to about 5 units/mg in an anti-factor IIa assay;
(ii) an antithrombin III (ATIII) specific activity against factor Xa of about 0.2 to about 1.5 units/mg in an anti-factor Xa assay; and
(iii) a solubility in aqueous media ranging from about 150 to about 1,000 mg/ml;
wherein:
said HCII-specific catalytic agent is a polyanionic carbohydrate of about 10 to about 24 monosaccharide units.

24. A method of claim 23, wherein said HCII-specific catalytic agent has an antithrombin III affinity of less than about 3% of that of unfractionated heparin.

25. A method of claim 24, wherein said HCII-specific catalytic agent has an anticoagulant effect which is contributed to by both an HCII- and ATIII-mediated mechanism, and by a mechanism which is independent of both HCII and ATIII.

26. A method of claim 25, wherein said polyanionic carbohydrate is a heparin preparation having a molecular weight of between about 3,000 and about 8,000 Daltons.

27. A method of claim 26, wherein said heparin preparation consists essentially of the lowest third molecular weight fraction isolated from unfractionated heparin.

28. A method of claim 26, wherein said heparin preparation is produced from unfractionated heparin by chemically lowering the molecular weight range to between about 3,000 and about 8,000 Daltons.

29. A method of claim 28, wherein said heparin preparation has an average molecular weight of about 8,000 Daltons.

30. A method of claim 28, wherein said heparin preparation has an average molecular weight of about 5,000 Daltons.

31. A method of claim 28, wherein said heparin preparation has an average molecular weight of about 3,000 Daltons.

32. A method of claim 28, wherein the antithrombin III affinity of said heparin preparation is reduced to less than about 3% of that of the unfractionated heparin.

33. A method of claim 32, wherein said reduction in the antithrombin III affinity is obtained by treating the vicinal alcohol groups present in said heparin preparation with an oxidizing agent followed by a reducing agent.

34. A method of claim 33, wherein said oxidizing agent is a member selected from the group consisting of sodium periodate, dimethyl sulfoxide, acid anhydrides, lead tetraacetate and ascorbic acid, and said reducing agent is a member selected from the group consisting of sodium borohydride, lithium aluminum hydride, metal hydrides and hydrazine.

35. A method of claim 26, wherein said heparin preparation consists essentially of material without affinity for ATIII, said material is prepared by affinity purification on a solid phase to which ATIII is immobilized and the effluent retained.

36. A method of claim 23, wherein said HCII-specific catalytic agent has the formula:

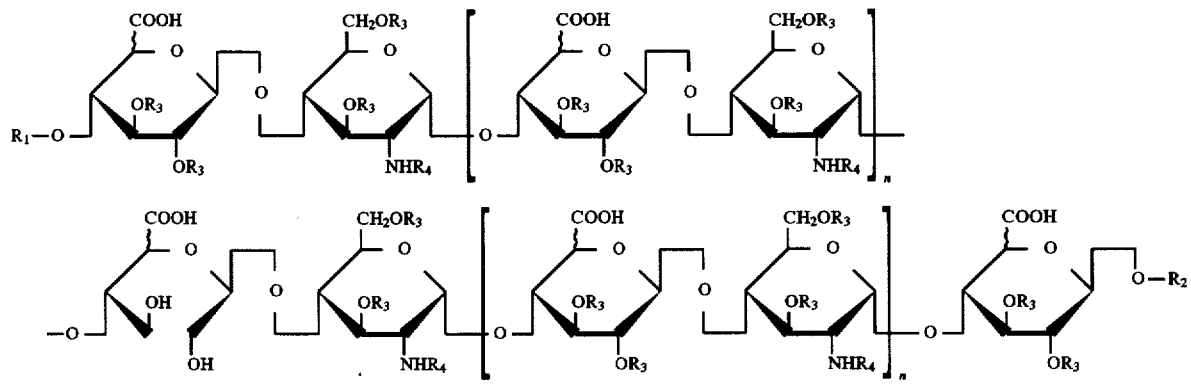

in which:

$R_1$ is a member selected from the group consisting of H, D-glucosamine acid residue, D-glucuronic acid residue and L-iduronic acid residue;

$R_2$ is a member selected from the group consisting of H, D-glucosamine acid residue, D-glucuronic acid residue, L-iduronic acid residue and anhydromannitol;

R₃ is a member selected from the group consisting of H and SO₃⁻;

R₄ is a member selected from the group consisting of H, SO₃⁻ and CH₃CO⁻; and the n indexes are independently selected and can have values ranging from 0 to about 14 wherein:

said HCII-specific catalytic agent has a molecular weight ranging from about 3,000 Daltons to about 8,000 Daltons.

37. A method of claim 23, wherein said HCII-specific catalytic agent has the formula:

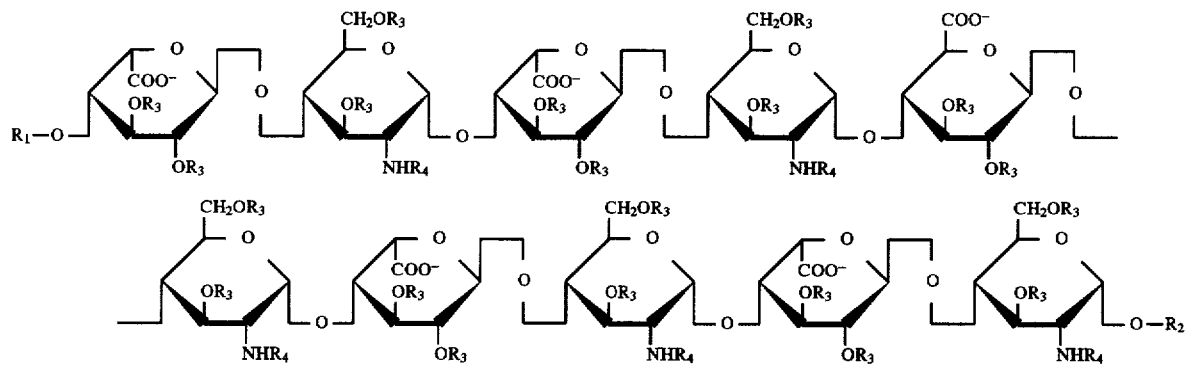

in which:

R₁ and R₂ are members independently selected from the group consisting of H, D-glucosamine acid residue, D-glucuronic acid residue and L-iduronic acid residue;

R₃ is a member selected from the group consisting of H and SO₃⁻; and

R₄ is a member selected from the group consisting of H, SO₃⁻ and CH₃CO⁻;

wherein:

said HCII-specific catalytic agent has a molecular weight ranging from about 3,000 Daltons to about 8,000 Daltons.

38. A method of claim 23, wherein said HCII-specific catalytic agent has a heparin cofactor II specific activity of about 3 to about 4 units/mg in anti-factor IIa activity.

39. A method of claim 23, wherein said HCII-specific catalytic agent has a ATIII specific activity of about 1.0 unit/mg in an anti-factor Xa assay.

40. A method of claim 23, wherein said HCII-specific catalytic agent is mixed with a heparin additive prior to patient administration.

41. A method of claim 40, wherein the weight ratio of said HCII-specific catalytic agent to said heparin additive is greater than about 2 to 1.

42. A method of claim 40, wherein said heparin additive is unfractionated heparin.

43. A method of claim 40, wherein said heparin additive is the lowest third molecular weight fraction isolated from unfractionated heparin.

44. A pharmaceutical composition for inhibiting thrombogenesis in a patient, said composition comprising:

(i) from about 90 to about 99.9 weight percent of an HCII-specific catalytic agent that inactivates fibrin-bound thrombin, said HCII-specific catalytic agent having only low affinity for antithrombin III (ATIII);

(ii) from about 0.1 to about 10 weight percent of an ATIII catalytic agent that inactivates fluid phase thrombin, wherein:

said HCII-specific catalytic agent is a polyanionic carbohydrate of about 10 to about 24 monosaccharide units and the HCII catalytic activity of said composition is about 2 to about 5 units/mg.

45. A composition of claim 44, wherein said polyanionic carbohydrate is a heparin preparation having a molecular weight of between about 3,000 and about 8,000 Daltons.

46. A composition of claim 44, wherein said ATIII catalytic agent is unfractionated heparin.

47. A composition of claim 44, wherein said ATIII catalytic agent is the lowest third molecular weight fraction isolated from unfractionated heparin.

48. A method for inhibiting clot-bound thrombin and fluid-phase thrombin in a patient without inducing a clinically unsafe increase in systemic bleeding, said method comprising the step of administering to the patient a pharmacologically acceptable dose of:

(i) an HCII-specific catalytic agent that inactivates clot-bound thrombin, said HCII-specific catalytic agent having low affinity for antithrombin III (ATIII) and a heparin cofactor II specific activity against heparin cofactor II of about 2 to about 5 units/mg in an anti-factor IIa assay; and (ii) an ATIII catalytic agent that inactivates fluid-phase thrombin;

wherein:

said HCII-specific catalytic agent is a polyanionic carbohydrate of about 10 to about 24 monosaccharide units.

49. A method of claim 48, wherein said HCII-specific catalytic agent and said ATIII catalytic agent are administered to the patient simultaneously.

50. A method of claim 48, wherein said HCII-specific catalytic agent has an anticoagulant effect which is contributed to by both an HCII- and ATIII-mediated mechanism, and by a mechanism which is independent of both HCII and ATIII.

51. A method of claim 48, wherein said polyanionic carbohydrate is a heparin preparation having a molecular weight of between about 3,000 and about 8,000 Daltons.

52. A method of claim 48, wherein said HCII-specific catalytic agent has the formula:

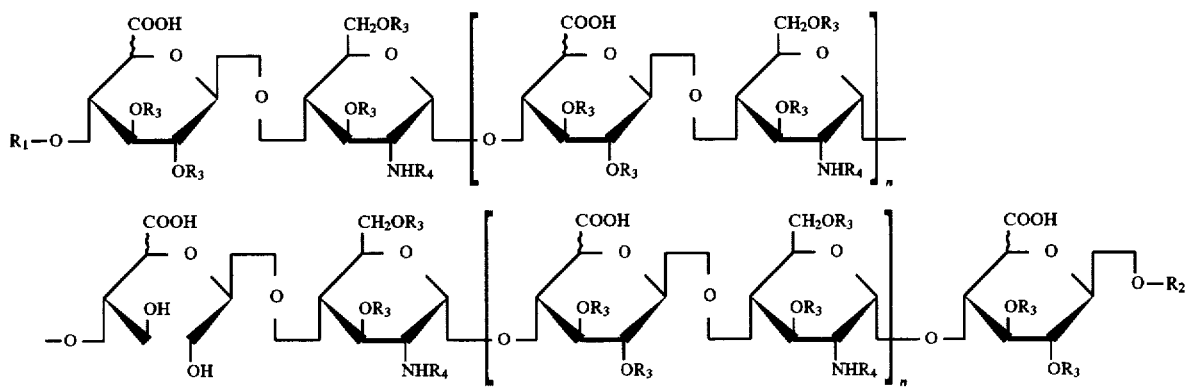

in which:

R₁ is a member selected from the group consisting of H, D-glucosamine acid residue, D-glucuronic acid residue and L-iduronic acid residue;

R₂ is a member selected from the group consisting of H, D-glucosamine acid residue, D-glucuronic acid residue, L-iduronic acid residue and anhydromannitol;

R₃ is a member selected from the group consisting of H and $SO_3^-$;

R₄ is a member selected from the group consisting of H, $SO_3^-$ and $CH_3CO^-$; and the n indexes are independently selected and can have values ranging from 0 to about 14 wherein:

said HCII-specific catalytic agent has a molecular weight ranging from about 3,000 Daltons to about 8,000 Daltons.

53. A method of claim 48, wherein said HCII-specific catalytic agent has the formula:

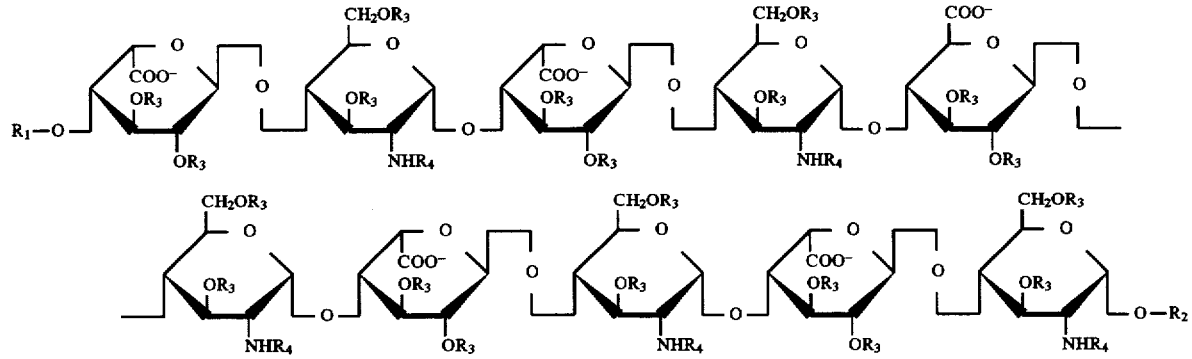

in which:

R₁ and R₂ are members independently selected from the group consisting of H, D-glucosamine acid residue, D-glucuronic acid residue and L-iduronic acid residue;

R₃ is a member selected from the group consisting of H and $SO_3^-$; and

R₄ is a member selected from the group consisting of H, $SO_3^-$ and $CH_3CO^-$;

wherein:

said HCII-specific catalytic agent has a molecular weight ranging from about 3,000 Daltons to about 8,000 Daltons.

54. A method of claim 48, wherein said HCII-specific catalytic agent has a heparin cofactor II specific activity of about 3 to about 4 units/mg in anti-factor IIa activity.

55. A method of claim 48, wherein said ATIII catalytic agent is unfractionated heparin.

56. A method of claim 48, wherein said ATIII catalytic agent is the lowest third molecular weight fraction isolated from unfractionated heparin.

* * * * *

UNITED STATES PATENT AND TRADEMARK OFFICE
CERTIFICATE OF CORRECTION

PATENT NO. : 5,763,427
DATED : June 9, 1998
INVENTOR(S) : Jeffrey I. Weitz, Jack Hirsh and Edward Young It is certified that error appears in the above-identified patent and that said Letters Patent is hereby corrected as shown below:

On the cover page, left column, the information under "Assignee" should read as follows:

[ * ]  The term of this patent shall not extend beyond the expiration date of Pat. No. 5,744,457.

Signed and Sealed this

Twenty-second Day of December, 1998

Attest:

BRUCE LEHMAN

Attesting Officer

Commissioner of Patents and Trademarks